US006945948B2

(12) United States Patent
Bainbridge et al.

(10) Patent No.: US 6,945,948 B2
(45) Date of Patent: Sep. 20, 2005

(54) EXTRA-CORPOREAL DUAL STAGE BLOOD PROCESSING METHOD AND APPARATUS

(75) Inventors: Marlene Bainbridge, Lakewood, CO (US); Muriel Keller, Thornton, CO (US); Timothy M. Gordon, Littleon, CO (US); Michael J. McAteer, Lakewood, CO (US); Scott D. Butzke, Littleton, CO (US)

(73) Assignee: Gambro, Inc., Lakewood, CO (US)

( * ) Notice: Subject to any disclaimer, the term of this patent is extended or adjusted under 35 U.S.C. 154(b) by 105 days.

(21) Appl. No.: 10/709,194

(22) Filed: Apr. 20, 2004

(65) Prior Publication Data

US 2004/0249332 A1 Dec. 9, 2004

Related U.S. Application Data

(62) Division of application No. 09/803,304, filed on Mar. 9, 2001, now Pat. No. 6,730,055.
(60) Provisional application No. 60/188,133, filed on Mar. 9, 2000.

(51) Int. Cl.[7] .............................................. A61M 37/00
(52) U.S. Cl. .................... 604/6.04; 604/6.01; 604/6.11; 210/782
(58) Field of Search ...................... 604/5.01, 6.01–6.05, 604/6.07–6.11, 6.15–6.16; 210/752, 781–2, 645, 787, 739–41; 490/437; 494/36, 37

(56) References Cited

U.S. PATENT DOCUMENTS

| | | | |
|---|---|---|---|
| 3,737,096 A | 6/1973 | Jones et al. | |
| 3,946,731 A | 3/1976 | Lichtenstein | |
| 4,010,894 A | 3/1977 | Kellogg et al. | |
| 4,094,461 A | 6/1978 | Kellogg et al. | |

(Continued)

FOREIGN PATENT DOCUMENTS

| | | |
|---|---|---|
| DE | 2636290 | 2/1978 |
| EP | 0096217 | 12/1983 |
| EP | 0165751 | 12/1985 |
| EP | 0214803 | 3/1987 |
| EP | 0233112 | 8/1987 |
| EP | WO 88/01880 | 3/1988 |
| EP | WO 88/05691 | 8/1988 |

(Continued)

OTHER PUBLICATIONS

"Red Cell Apheresis: Challenges For Donor And Blood Component Collection Management" 24th Congress International Congress Of Blood Transfusion Haemonetics Luncheon Seminar, Centre For Blood And Cancer Diseases, Berlin, Germany, Apr. 2, 1996.

(Continued)

*Primary Examiner*—Angela D. Sykes
*Assistant Examiner*—Leslie R. Deak
(74) *Attorney, Agent, or Firm*—John R. Merkling

(57) ABSTRACT

Methods and apparatus particularly involving the separation of blood into blood components and the collection of such components are disclosed. In one aspect, an extra-corporeal method for the collection of plasma and red blood cells is provided, wherein the collection of plasma and red blood cells may occur simultaneously or subsequently utilizing the same dual stage blood processing vessel. The flow of blood to the blood processing vessel and return of uncollected blood components may be provided via a single needle, wherein blood is removed from and returned to a donor/patient during alternating blood removal and blood return submodes. Platelet separation and collection options are also described. In either case, prior to red blood cell collection, a set-up phase may be carried out to set a predetermined hematocrit and AC ratio. Replacement fluid delivery may optionally also be provided either substantially continuously during any collection phase(s) and/or in a bolus mode.

28 Claims, 54 Drawing Sheets

U.S. PATENT DOCUMENTS

| | | |
|---|---|---|
| 4,114,802 A | 9/1978 | Brown |
| 4,120,448 A | 10/1978 | Cullis |
| 4,146,172 A | 3/1979 | Cullis et al. |
| 4,185,629 A | 1/1980 | Cullis et al. |
| 4,187,979 A | 2/1980 | Cullis et al. |
| 4,216,770 A | 8/1980 | Cullis et al. |
| 4,223,672 A | 9/1980 | Terman et al. |
| 4,263,808 A | 4/1981 | Bellotti et al. |
| 4,303,193 A | 12/1981 | Latham, Jr. |
| 4,370,983 A | 2/1983 | Lichtenstein |
| 4,379,452 A | 4/1983 | DeVries |
| 4,425,112 A | 1/1984 | Ito |
| 4,436,620 A | 3/1984 | Bellotti et al. |
| 4,479,760 A | 10/1984 | Bilstad et al. |
| 4,479,761 A | 10/1984 | Bilstad et al. |
| 4,526,515 A | 7/1985 | Devries |
| 4,626,243 A | 12/1986 | Singh et al. |
| 4,637,813 A | 1/1987 | Devries |
| 4,661,246 A | 4/1987 | Ash |
| 4,680,025 A | 7/1987 | Kruger et al. |
| 4,708,712 A | 11/1987 | Mulzet |
| 4,798,090 A | 1/1989 | Heath et al. |
| 4,804,363 A | 2/1989 | Valeri |
| 4,834,890 A | 5/1989 | Brown et al. |
| 4,851,126 A | 7/1989 | Schoendorfer |
| 4,897,184 A | 1/1990 | Shouldice et al. |
| 4,915,848 A | 4/1990 | Carmen et al. |
| 4,934,995 A | 6/1990 | Cullis |
| 4,968,295 A | 11/1990 | Neumann |
| 4,985,153 A | 1/1991 | Kuroda et al. |
| 5,076,911 A | 12/1991 | Brown et al. |
| 5,078,671 A | 1/1992 | Dennehey et al. |
| RE33,924 E | 5/1992 | Valeri |
| 5,118,428 A | 6/1992 | Sand et al. |
| 5,120,303 A | 6/1992 | Hombrouckx |
| 5,121,470 A | 6/1992 | Trautman |
| 5,135,667 A | 8/1992 | Schoendorfer |
| 5,154,716 A | 10/1992 | Bauman et al. |
| 5,171,456 A | 12/1992 | Hwang et al. |
| 5,174,894 A | 12/1992 | Ohsawa et al. |
| 5,178,603 A | 1/1993 | Prince |
| 5,188,583 A | 2/1993 | Guigan |
| 5,217,426 A | 6/1993 | Bacehowski et al. |
| 5,267,956 A | 12/1993 | Beuchat |
| 5,273,517 A | 12/1993 | Barone et al. |
| 5,316,667 A | 5/1994 | Brown et al. |
| 5,321,800 A | 6/1994 | Lesser |
| 5,348,533 A | 9/1994 | Papillon et al. |
| 5,360,542 A | 11/1994 | Williamson, IV et al. |
| 5,362,291 A | 11/1994 | Williamson, IV |
| 5,370,802 A | 12/1994 | Brown |
| 5,387,187 A | 2/1995 | Fell et al. |
| 5,432,054 A | 7/1995 | Saunders et al. |
| 5,441,636 A | 8/1995 | Chevallet et al. |
| 5,445,506 A | 8/1995 | Afflerbaugh et al. |
| 5,472,621 A | 12/1995 | Matkovich et al. |
| 5,494,578 A | 2/1996 | Brown et al. |
| 5,496,265 A | 3/1996 | Langley et al. |
| 5,505,685 A | 4/1996 | Antwiler |
| 5,523,004 A | 6/1996 | Tanokura et al. |
| 5,529,691 A | 6/1996 | Brown |
| 5,581,687 A | 12/1996 | Lyle et al. |
| 5,605,842 A | 2/1997 | Langley et al. |
| 5,607,579 A | 3/1997 | Latham, Jr. et al. |
| 5,614,106 A | 3/1997 | Payrat et al. |
| 5,628,915 A | 5/1997 | Brown et al. |
| 5,637,082 A | 6/1997 | Pages et al. |
| 5,653,887 A | 8/1997 | Wahl et al. |
| 5,693,232 A | 12/1997 | Brown et al. |
| 5,704,888 A | 1/1998 | Hlavinka et al. |
| 5,720,716 A * | 2/1998 | Blakeslee et al. .......... 604/4.01 |
| 5,853,382 A | 12/1998 | Kingsley et al. |
| 5,865,785 A | 2/1999 | Bischof |
| 5,941,842 A | 8/1999 | Steele et al. |
| 5,951,877 A | 9/1999 | Langley et al. |
| 5,954,971 A | 9/1999 | Pages et al. |
| 6,007,725 A | 12/1999 | Brown |
| 6,080,322 A | 6/2000 | Deniega et al. |
| 6,730,055 B2 * | 5/2004 | Bainbridge et al. ........ 604/6.04 |

FOREIGN PATENT DOCUMENTS

| | | |
|---|---|---|
| EP | 0284764 | 10/1988 |
| EP | 0303765 | 2/1989 |
| EP | WO 95/03107 | 2/1995 |
| FR | 2390173 | 4/1978 |
| GB | 2176717 A | 1/1987 |
| WO | WO 93/12888 | 7/1993 |
| WO | WO 94/11093 | 5/1994 |

OTHER PUBLICATIONS

Baxier Healthcare Corporation, *CS–3000 Plus Parameter Changes, Operator's Manual,* prior to Mar. 9, 2000, pp. 1–1–1–24, 4–1–4–3, 5–1–5–2, 8–1–8–22, 9–1–9–44, 12–12–12–36.

COBE BCT, Inc., COBE SPECTRA Apheresis System, Operator's Manual, Feb. 1991, pp. xi–xxvii, 1–1–1–53, 3A–1, 3A–8, 3A–11, 4A–1, 4A–39, 4B–1–4B–42, 9–1–9–4.

Fresenius Ag, Operating Instructions AS 104 Blood Cell Separator, 1990, pp. 0–1–05, 1–3–1–6, 1–23, 2–0–2–51, 3–1–3–14, 4–1–4–16, 7–1–7–11, 7–13.

Haemonatics Corporation, *Haemonetics Mobile Collection System Owner's Operating and Maintenance Manuel,* 1991, pp. 1–2–7–14.

Haemonetics Corporation, *MCS+ for RBC Apheresis: Two Unit Red Cells protocol,* Chapter 6, , prior to Mar. 9, 2000, pp. 6–1 through 6–32.

Mathes et al, "Improved Red Cell Quality After Erythroplasmapheresis With MCS–3P", *Journal Of Clinical Apheresis,* 9:183–188, 1994.

Terumo Medical Corporation,—"Now Make the Direct Connection for Sterile Connection", Advertisement 1995 or earlier.

Valbonesl et al., "Multicomponent collection (MCS): a new trend in transfusion medicine", *The International Journal of Artificial Organs,* vol. 17, No. 2, 1994, , pp. 66–69.

Valbonesi et al., "Single–Donor Platelet Concentrated Produced Along With Packed Red Blood Cells with the Haemonetics MCS 3: Preliminary Results", *Journal of Clinical Apheresis* 9:195–199, 1994.

\* cited by examiner

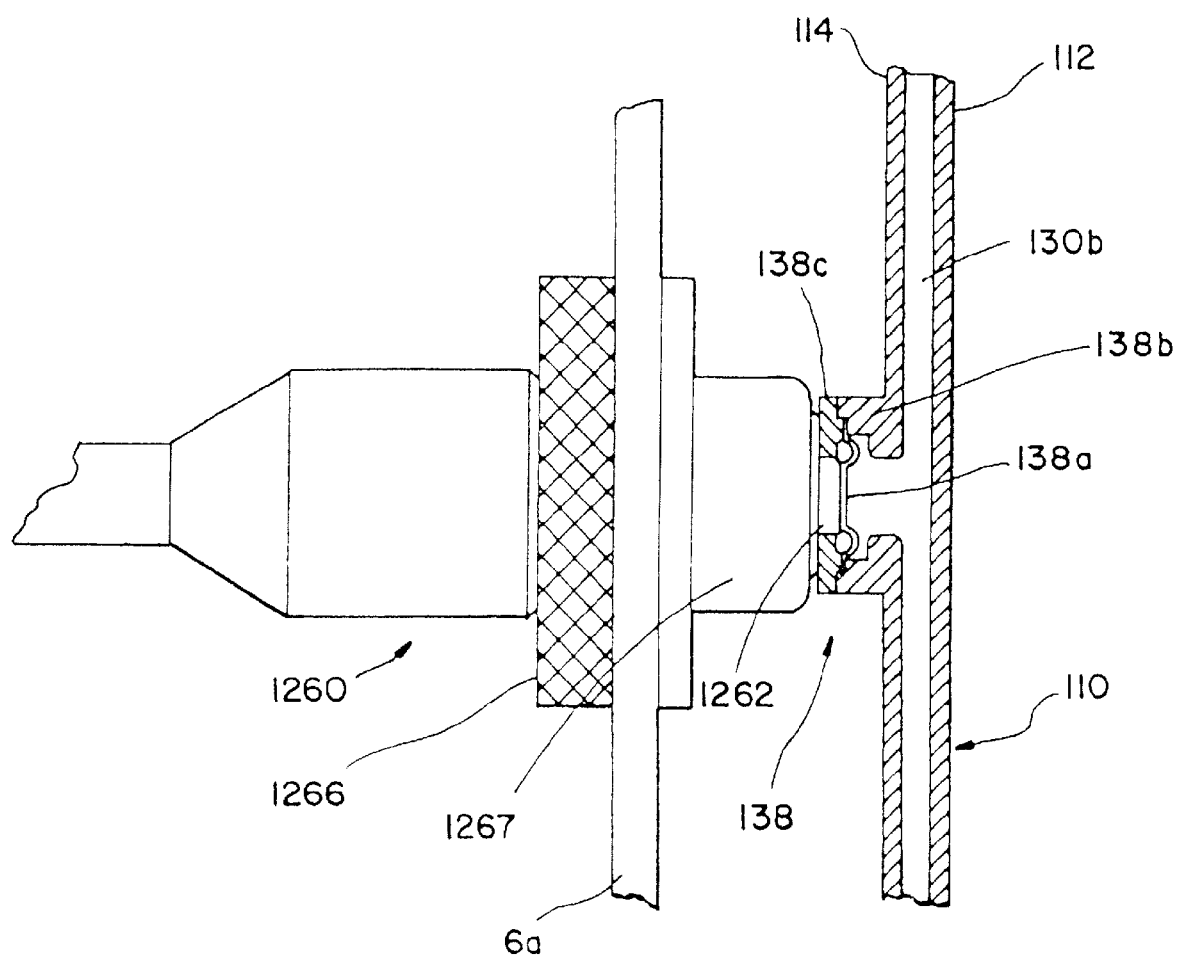

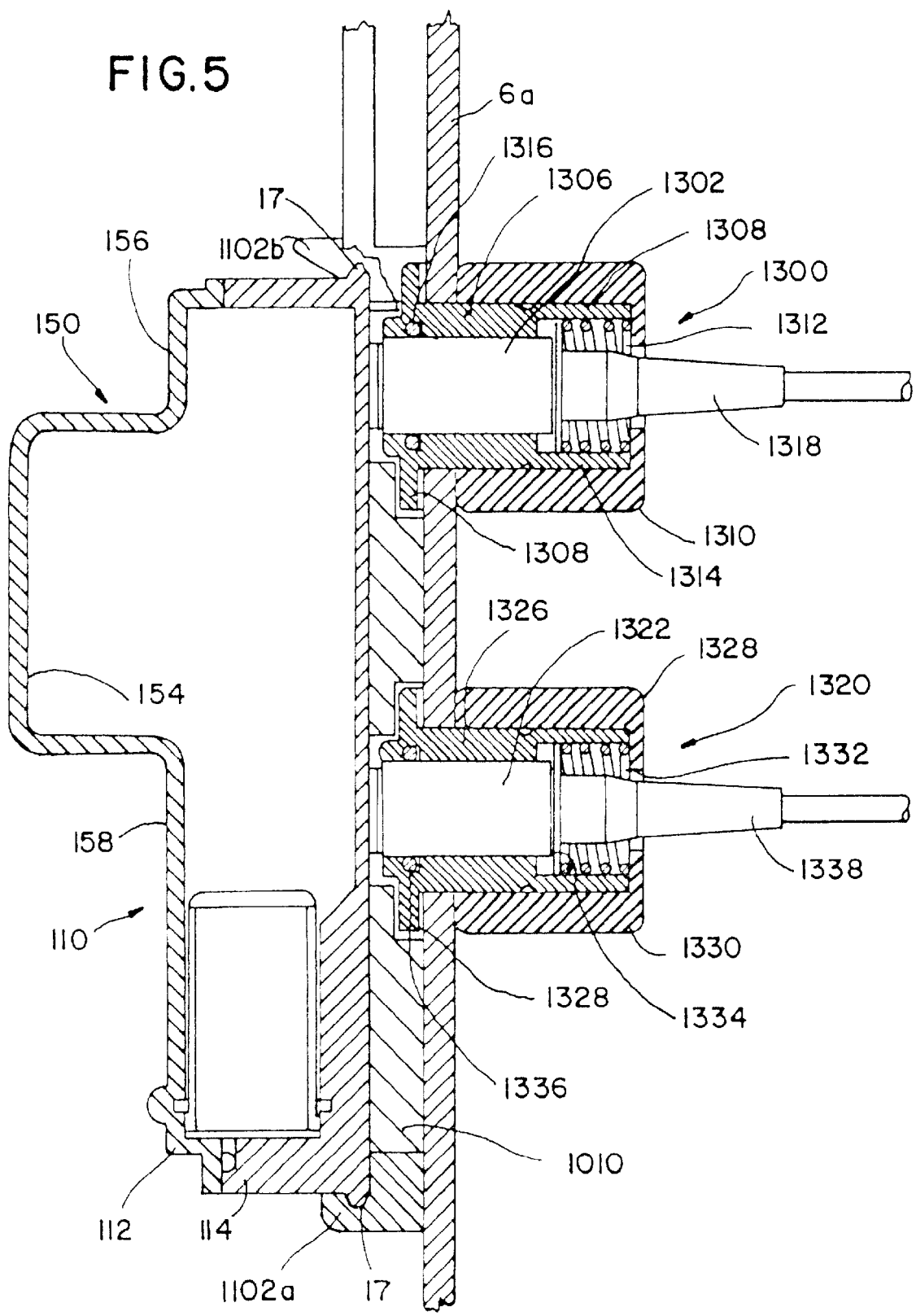

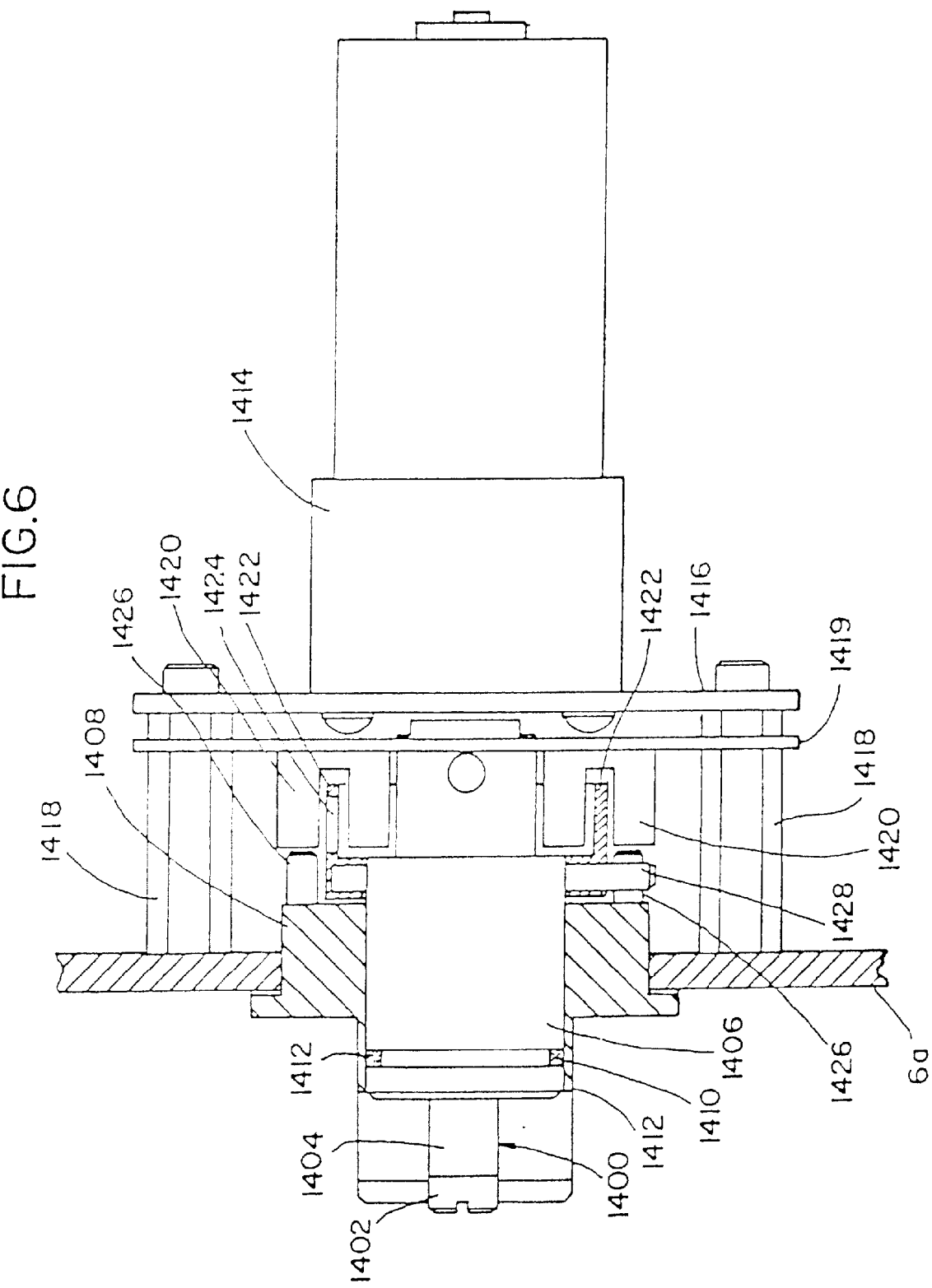

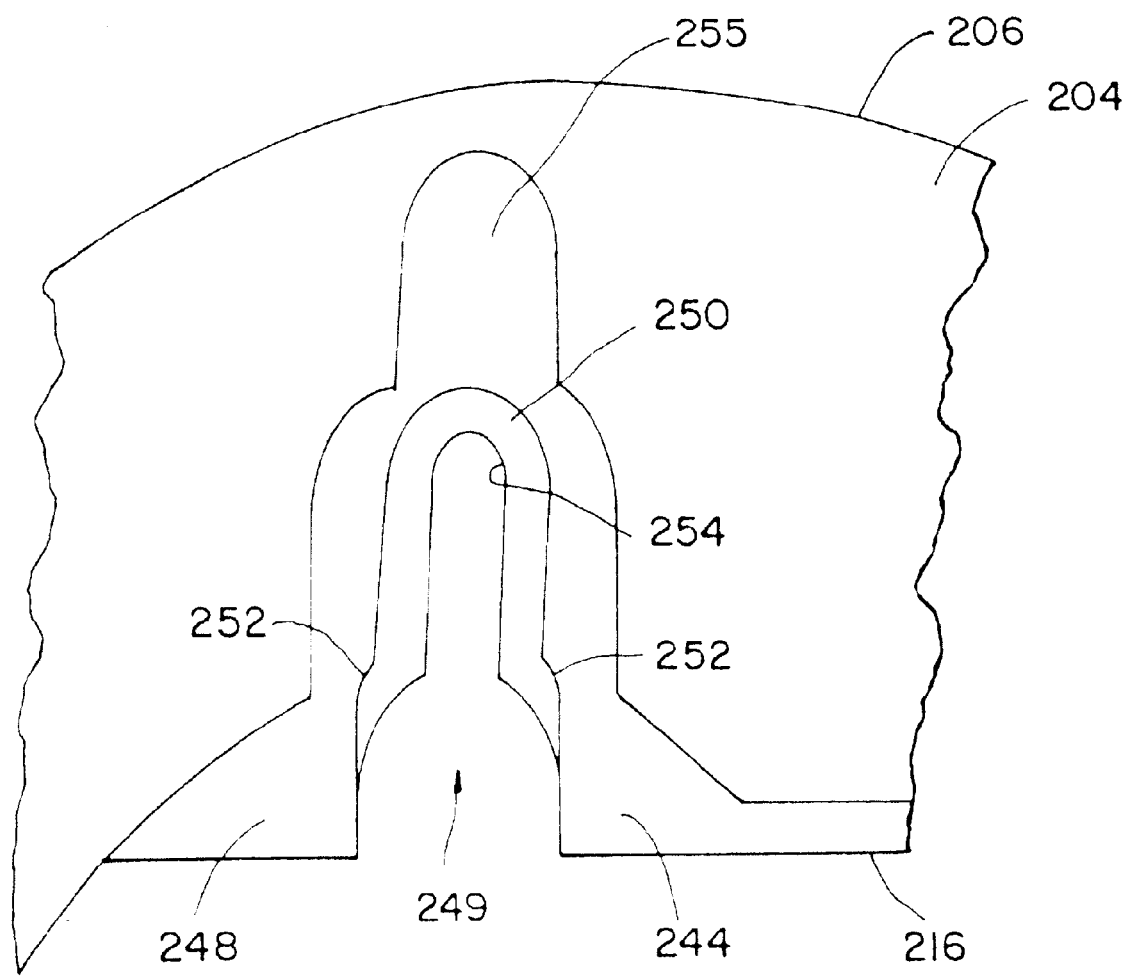

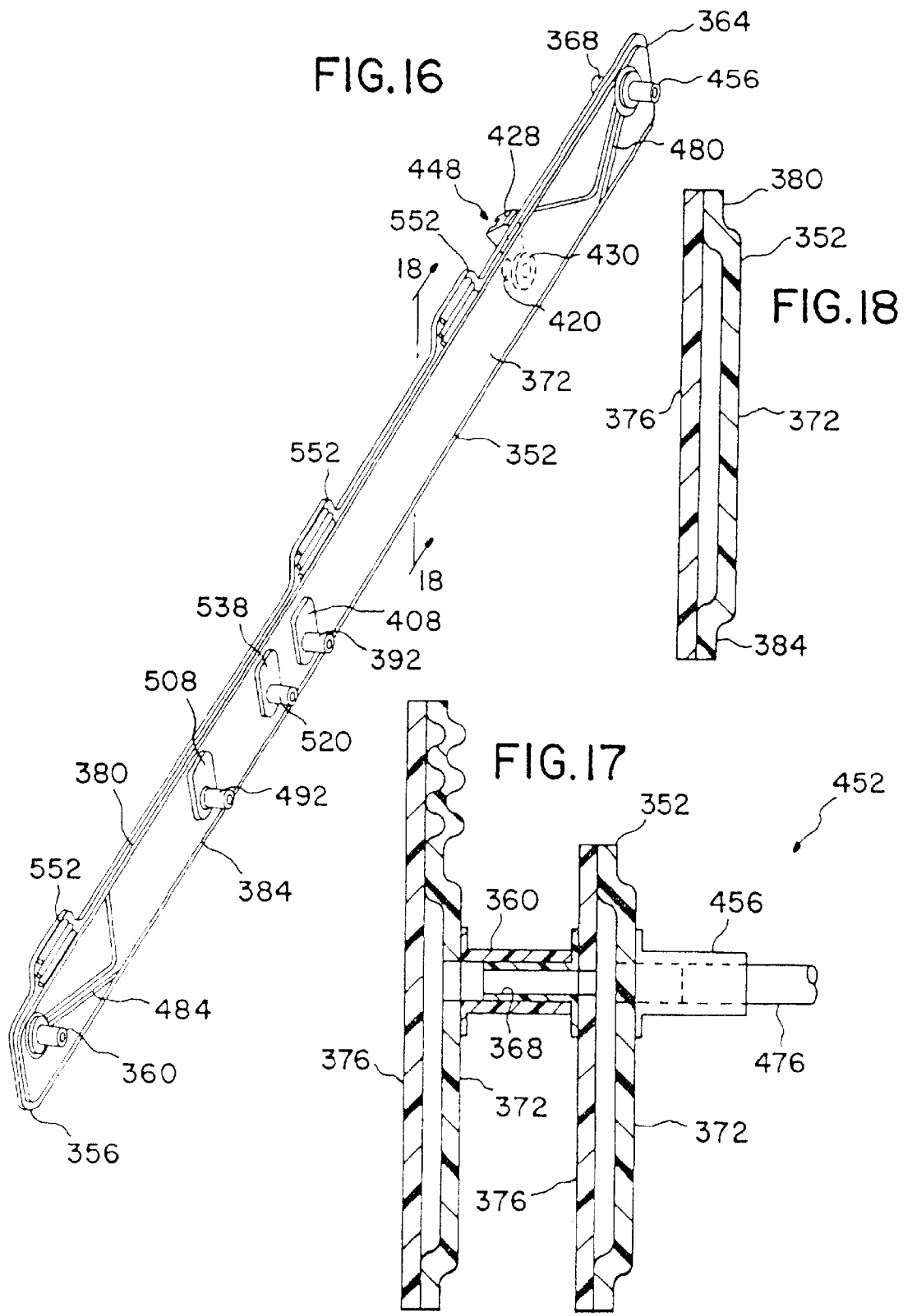

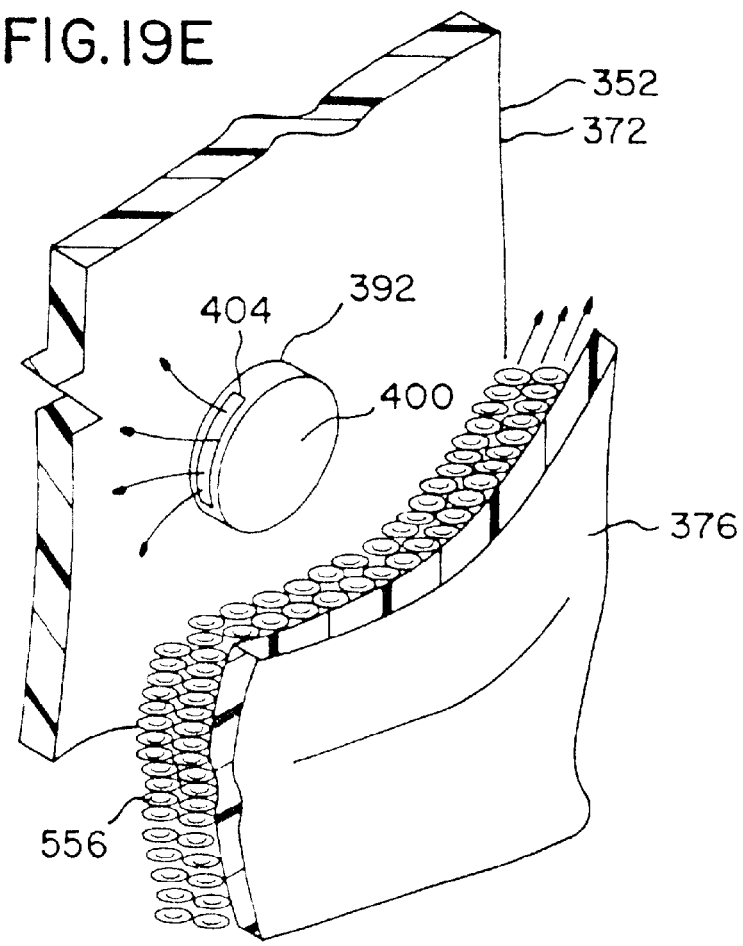
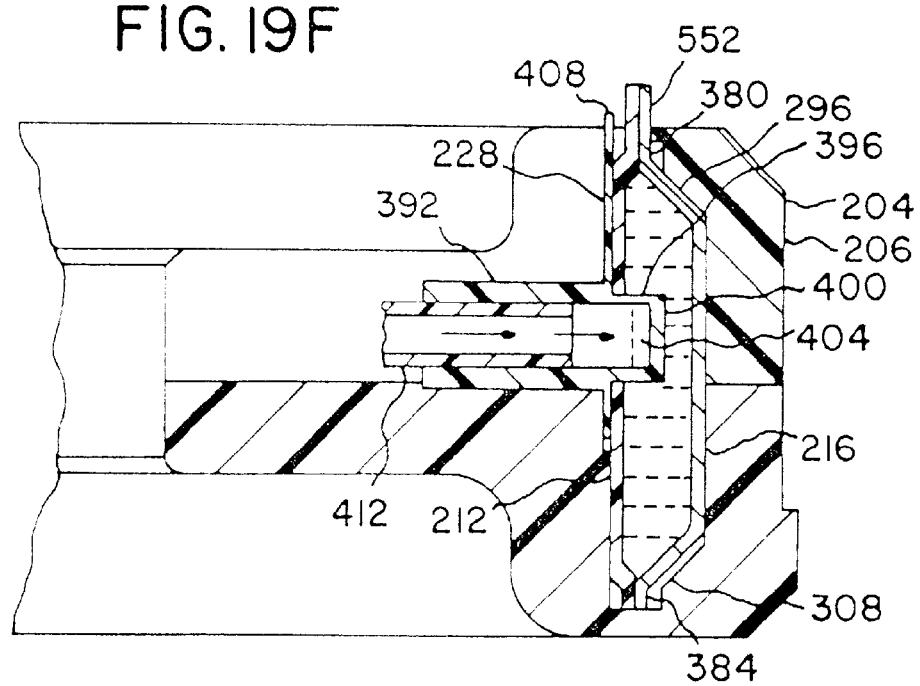

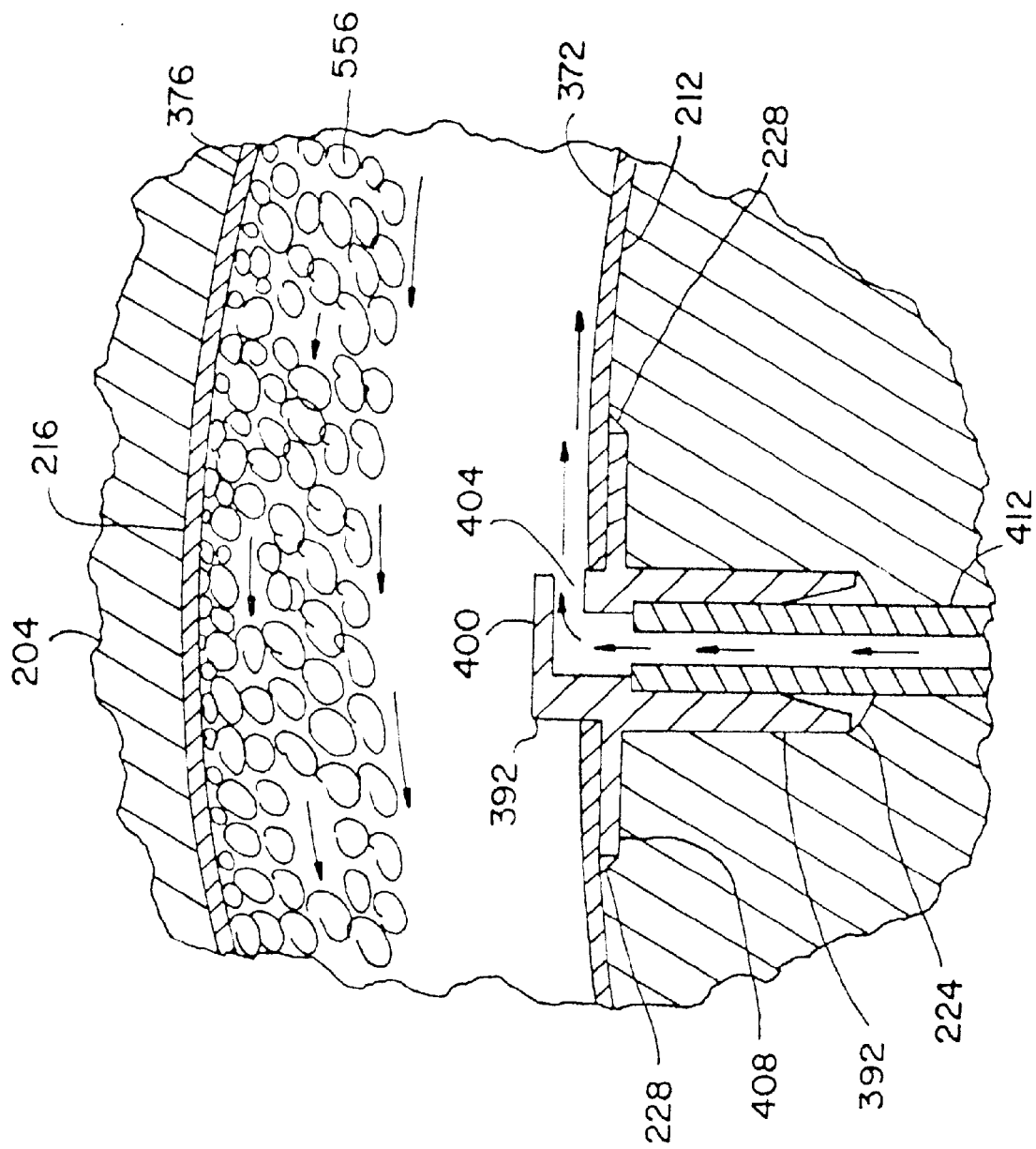

EXTRA-CORPOREAL DUAL STAGE BLOOD PROCESSING METHOD AND APPARATUS

CROSS REFERENCE TO RELATED APPLICATIONS

This case is a divisional of U.S. patent application Ser. No. 09/803,304, filed Mar. 9, 2001, now U.S. Pat. No. 6,730,055 incorporated herein by reference, which claims the benefit of U.S. Provisional Patent Application No. 60/188133 filed Mar. 9, 2000.

BACKGROUND OF INVENTION

One type of extra-corporeal blood processing is an apheresis procedure in which blood is removed from a donor or patient (hereafter, donor/patient), directed to a blood component separation device (e.g., centrifuge), and separated into various blood component types (e.g, red blood cells, white blood cells, platelets, plasma) for collection and/or therapeutic purposes. One or more of these blood component types are collected (e.g, for therapeutic transfusion purposes), while the remainder are preferably returned to the donor or donor/patient.

A number of factors may affect the commercial viability of an apheresis system. One factor relates to the operator of the system, specifically the time and/or expertise required of an individual to prepare and operate the apheresis system. For instance, reducing the time required by the operator to load and unload the disposables, as well as the complexity of these actions, can increase productivity and/or reduce the potential for operator error. Moreover, reducing the dependency of the system on the operator may lead to reductions in operator errors and/or to reductions in the credentials desired/required for the operators of these systems.

Donor-related factors may also impact the commercial viability of an apheresis system and include donor convenience and donor comfort. For instance, donors typically have a limited amount of time which may be committed to visiting a blood component collection facility for a donation. Consequently, once at the collection facility the amount of the donor's time which is actually spent collecting blood components is another factor which should be considered. This also relates to donor comfort in that many view the actual collection procedure as being somewhat discomforting in that at least one and sometimes two access needles are disposed in the donor throughout the procedure.

Performance-related factors continue to affect the commercial viability of an apheresis system. Performance may be judged in terms of the "collection efficiency" of the apheresis system, which may in turn reduce the amount of donation time and thus increase donor convenience. The "collection efficiency" of a system may of course be gauged in a variety of ways, such as by the amount of a particular blood component type which is collected in relation to the quantity of this blood component type which passes through the apheresis system. Performance may also be evaluated based upon the effect which the apheresis procedure has on the various blood component types. For instance, it is desirable to minimize the adverse effects on the blood component types as a result of the apheresis procedure (e.g., reduce platelet activation).

SUMMARY OF INVENTION

The present invention generally relates to extra-corporeal blood processing. Since each of the various aspects of the present invention may be incorporated into an apheresis system (e.g, whether for blood component collection in which "healthy" cells and/or plasma are removed from the blood or for therapeutic purposes in which "unhealthy" cells and/or plasma are removed from the blood), the present invention will be described in relation to this particular application. However, at least certain of the aspects of the present invention may be suited for other extra-corporeal blood processing applications and such are also within the scope of the present invention.

A typical apheresis system which may embody one or more aspects of the present invention would generally include a blood component separation device; for example, a membrane-based separation device and/or, a rotatable centrifuge element, such as a rotor, which provides the forces required to separate blood into its various blood component types (e.g., red blood cells, white blood cells, platelets, and/or plasma). In one preferred embodiment, the separation device includes a channel which receives a blood processing vessel. Typically, a healthy human donor or a donor/patient suffering from some type of illness (collectively referred to here as a donor/patient) is fluidly interconnected with the blood processing vessel by an extra-corporeal tubing circuit, and preferably the blood processing vessel and extra-corporeal tubing circuit collectively define a closed, sterile system. When the fluid interconnection is established, blood may be extracted from the donor/patient and directed to the blood component separation device such that at least one type of blood component may be separated and removed from the blood, either for collection or for therapy.

When the blood processing vessel is loaded into the channel, the blood processing vessel and most of the tubing lines must be primed. In this regard, an aspect of the present invention relates to priming these elements, preferably with blood. A channel associated with a channel housing, which is rotatably interconnected with a centrifuge rotor, preferably includes a first cell separation stage. The channel extends generally curvilinearly about a rotational axis of the channel housing in a first direction. The channel preferably includes, progressing in the first direction, the first cell separation stage, a red blood cell dam, a platelet and/or a plasma collection area, and an interface control region for controlling a radial position of at least one interface between red blood cells (RBCs) and an adjacent blood component type(s) (e.g., plasma and/or a buffy coat of white blood cells (WBCs), lymphocytes, and platelets). Blood introduced into the channel is separated into layers of red blood cells (and/or a buffy coat generally including white blood cells and platelets), and plasma in the first cell separation stage. Preferably, throughout an RBC/plasma apheresis procedure (e.g., a non-platelet procedure) and including the priming of the blood processing vessel, only separated plasma flows beyond the red blood cell dam where the plasma may be removed from the channel in the plasma collection area. This is provided by an interface control mechanism which is disposed in the interface control region of the channel and which maintains the position of the interface between separated red blood cells and the plasma such that this condition is maintained. Note, the buffy coat (platelets and WBCs) is also preferably kept behind the RBC dam in the RBC/plasma collection procedures. In this embodiment, the buffy coat is generally collected with the RBCs and may be either later filtered out (e.g., the WBCs by leukoreduction filtration) or left in the RBC product (the platelets).

Although the term "blood prime" may be subject to a variety of characterizations, in each case described herein, blood is the first fluid introduced into the blood processing vessel. One characterization of the blood prime is that separated plasma is provided to the interface control region before any separated red blood cells would ever flow beyond the red blood cell dam into the plasma collection area. Preferably, no RBCs ever flow over the RBC dam. Another characterization is that blood and/or blood component types occupy the entire fluid-containing volume of the blood processing vessel before any separated red blood cells would flow beyond the red blood cell dam into the plasma collection area.

A further aspect of the present invention relates to blood priming an apheresis system which includes a channel housing having a blood processing channel associated therewith, a blood processing vessel disposed in the channel and which has a blood inlet port and a red blood cell (RBC) outlet port which also acts as an interface control port. The RBC/interface control port is used to control the radial position of at least one interface between separated red blood cells and a blood component type(s), here preferably plasma, disposed adjacent the separated red blood cells.

Another aspect of the present invention relates to the RBC/control port which assists in automatically controlling (i.e., without operator action) the location of an interface between the separated red blood cells and the separated plasma relative to a red blood cell dam in the processing vessel. The red blood cell dam restricts the flow of separated red blood cells to a plasma collect port. The RBC/control port extends through the blood processing vessel and removes plasma and red blood cells as required in order to reduce the potential for red blood cells flowing "over" the red blood cell dam to the plasma collect port. The capability of "selective" removal of red blood cells from the blood processing vessel through the RBC/control port is based at least in part upon its position within the channel. That is, the automatic control provided at least in part by the control port is predicated upon the control port assuming a predetermined radial position within the channel. In order to facilitate achieving this predetermined radial position within the channel, the disposition of the control port is provided independently of the thickness of the blood processing vessel. Specifically, the position of the control port is not dependent upon the thickness of the materials which form the blood processing vessel.

Another aspect of the present invention relates to a packing factor associated with the separated blood component types in a separation stage of the blood processing vessel. The packing factor is a number which reflects the degree with which the blood component types are "packed together" in the separation stage and is dependent at least upon the rotational speed of the channel housing and the flow rate into the blood processing vessel. The packing factor may be characterized as a dimensionless "density" of sorts of the respective blood component type in the respective separation stage. One embodiment of this aspect is a method which includes the steps of rotating the channel housing, providing a flow to the blood processing vessel in the channel housing (e.g., the flow includes blood and typically anticoagulant as well), separating the blood into a plurality of blood component types, and adjusting the rotational speed of the channel housing based upon a certain change in the flow rate. Since the packing factor is dependent upon the rotational speed of the channel housing and the flow rate into the blood processing vessel, the methodology of this aspect may be used to maintain a substantially constant and predetermined packing factor. In this regard, preferably the packing factor is maintained between about 11 and about 15, and preferably about for collection of RBCs alone and preferably about 16 for collection of RBCs contemporaneously with plasma.

A further aspect of the present invention relates to the extracorporeal collection of both or either plasma and red blood cells utilizing the same blood processing vessel. More particularly, such a method includes flowing blood from a donor/patient to a blood processing vessel and separating plasma from the blood within the blood processing vessel. At least a portion of the plasma is collected in a collection reservoir that is separate from the blood processing vessel. Further, such a method may include separating red blood cells from the blood within the blood processing vessel and collecting at least a portion of the separated red blood cells within a red blood cell collection reservoir that is also separate from blood processing vessel. In one approach, the collection of plasma and red blood cells may be advantageously completed contemporaneously, although they may also be collected during separate time periods. For example, plasma collection may be completed prior to red blood cell collection. Alternatively, red blood cell collection may precede plasma collection. Note, in a continuous apheresis process, the steps of separating and collecting may be performed substantially simultaneously.

In conjunction with this aspect of the present invention, and prior to the step of collecting red blood cells, the method may further include a set-up phase during which a desired packing factor is established within the separated red blood cells in the blood processing vessel and a desired AC ratio may be established. Preferably, such a packing factor is established to be between about 11 and 21, and most preferably at about 13 for collection of RBCs alone and 16 for collection of RBCs contemporaneously with plasma. Further, it is preferable that the AC ratio be established to be between about 6 and 16, and most preferably at about 8. The method may further include removing blood from a donor/patient and returning uncollected components of the blood to the donor/patient via use of a single needle. Such removing and returning steps may be alternately and repeatedly carried out during blood processing, including during the set-up and collection phases for red blood cell collection. If the collection of plasma alone is desired, the method may further include separating plasma from the blood within the blood processing vessel and collecting at least a portion of the separated plasma in a separate plasma collection reservoir. Most preferably, plasma separation/collection may be completed contemporaneous with the separation/collection of RBCs. Alternatively or additionally, plasma separation/collection may be completed before or after the separation/collection of RBCs. The use of a replacement fluid is also contemplated during collection and/or may be used in a substantially continuous (including cycled for single needle draw/return alternating applications) or in a bolus form.

Moreover, another aspect of the present invention involves the presentation of versatility in providing virtually any option for the collection of red blood cell, plasma and/or platelet products. More specifically, the present system can be operated such at that upon input of the donor characteristics (e.g., height, weight, hematocrit and platelet pre-count) the present system will return a list optional donations this particular donor can provide. For example, with a sufficient total blood volume (calculated by the body height and weight, e.g.) and hematocrit and platelet pre-count, a donor can produce possibly several alternate and/or a plurality of products; and, the system can determine not only how many and what combinations of products this donor can donate, but also what might be preferred or prioritized by the blood center. A sufficiently large donor may produce one or more red blood cell products and one or more plasma products and/or one or more platelet products. Many variations of product combinations may now be realized. Different tubing and bag set options are also preferably presented for such alternative collection procedures.

These and other features of the present invention will be made manifest by the detailed description and the attached drawings which are intended to be read in conjunction with each other as set forth below.

BRIEF DESCRIPTION OF DRAWINGS

FIGS. 4A–4B are cross-sectional side views of first and second pressure sensing modules of the extracorporeal tubing circuit of FIGS. 2A–2D coupled with corresponding pressure sensors of the pump/valve/sensor assembly of FIGS. 1 and 3;

FIG. 5 is a cross-sectional side view of the upper and lower ultrasound sensors of the pump/valve/sensor assembly of FIG. 3 coupled with a reservoir of the cassette assembly of the extracorporeal tubing circuit of FIGS. 2A–2D;

FIG. 6 is a cross-sectional side view of a platelet divert or replacement fluid introduction valve subassembly of the pump/valve/sensor assembly of FIG. 3;

FIG. 11B is a lateral cutaway view, looking upwardly of the platelet collect well region of the channel housing of FIG. 8A;

FIG. 16 is an isometric view of the blood processing vessel of the channel assembly of FIG. 8A in a disassembled state;

FIG. 17 is a cross-sectional view of the blood processing vessel at the interconnection;

FIG. 18 is cross-sectional view of the blood processing vessel taken along lines 18—18 in FIG. 16;

FIG. 19E is a cutaway, isometric view of blood being introduced into the blood processing vessel of FIG. 8A during an apheresis procedure;

FIG. 19F is a cross-sectional view of blood being introduced into the blood processing vessel and channel of FIG. 8A during an apheresis procedure;

FIG. 19G is a cross-sectional view, looking downwardly, of blood being introduced into the blood processing vessel and channel of FIG. 8A during an apheresis procedure;

DETAILED DESCRIPTION

The present invention will be described in relation to the accompanying drawings which assist in illustrating the pertinent features hereof. Generally, all preferred aspects of the present invention relate to improvements in a blood apheresis system, both procedural and structural. However, certain of these improvements may be applicable to other extracorporeal blood processing applications and such are within the scope of the present invention as well.

Figure 1:
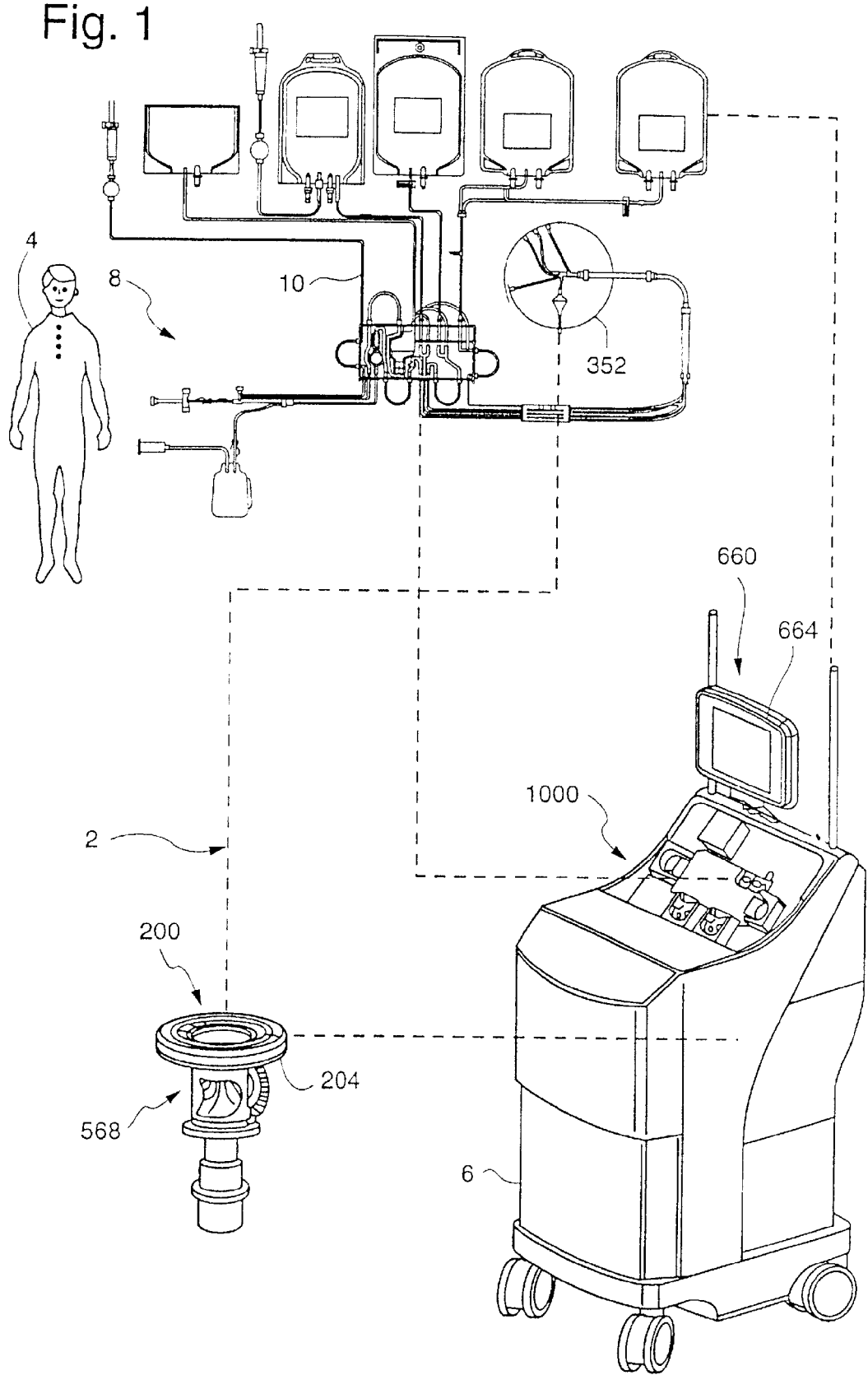
FIG. 1 is an isometric view of one embodiment of an apheresis system according to the present invention.

A preferred blood apheresis system 2 is illustrated in FIG. 1 and preferably provides for a continuous blood component separation process. Generally, whole blood is withdrawn from a donor/patient 4 and is provided to a blood component separation device 6 where the blood is separated into the various component types and at least one of these separated blood component types is collected by and/or removed from the device 6. These collected blood components may then be provided for subsequent use by another such as by transfusion and/or may be removed in favor of the delivery or infusion of replacement fluid(s) for therapeutic or non-therapeutic purposes, or may undergo a therapeutic treatment and be returned to the donor/patient 4.

In the blood apheresis system 2, blood is withdrawn from the donor/patient 4 and directed through a disposable set 8 which includes an extracorporeal tubing circuit 10 and a blood processing vessel 352 and which defines a completely closed and sterile system. The disposable set 8 is mounted on the blood component separation device 6 which includes a pump/valve/sensor assembly 1000 for interfacing with the extracorporeal tubing circuit 10, and a channel assembly 200 for interfacing with the disposable blood processing vessel 352.

The channel assembly 200 includes a channel housing 204 which is rotatably interconnected with a rotatable centrifuge rotor assembly 568 which provides the centrifugal forces required to separate blood into its various blood component types by centrifugation. The blood processing vessel 352 is interfitted with the channel housing Blood thus flows from the donor/patient 4, through the extracorporeal tubing circuit 10, and into the rotating blood processing vessel 352. The blood within the blood processing vessel 352 is separated into various blood component types and at least one of these blood component types (e.g., plasma, red blood cells) may preferably be continually removed from the blood processing vessel 352. Blood components which are not being collected for transfusion to a distinct recipient, or for therapeutic exchange or treatment (e.g., red blood cells, white blood cells, plasma, as described hereinbelow) are also removed from the blood processing vessel 352 and returned to the donor/patient 4 via the extracorporeal tubing circuit 10. A continuous process here preferably includes at least a continuously spinning/rotating vessel 352, and may also include continuous inflow of blood and/or outflow of separated products.

Operation of the blood component separation device 6 is preferably controlled by one or more processors included therein, and may advantageously comprise a plurality of embedded processors. Such processors may be like those used in personal computers or the like, and/or preferably accommodate interface capabilities with ever-increasing computer user facilities (e.g., CD ROM, modem, audio, networking and other capabilities). Relatedly, in order to assist the operator of the apheresis system with various aspects of its operation, the blood component separation device 6 preferably includes a graphical interface 660 preferably with a touch screen input/output device 664.

Disposable Set: Extracorporeal Tubing Circuit

Figure 2A:
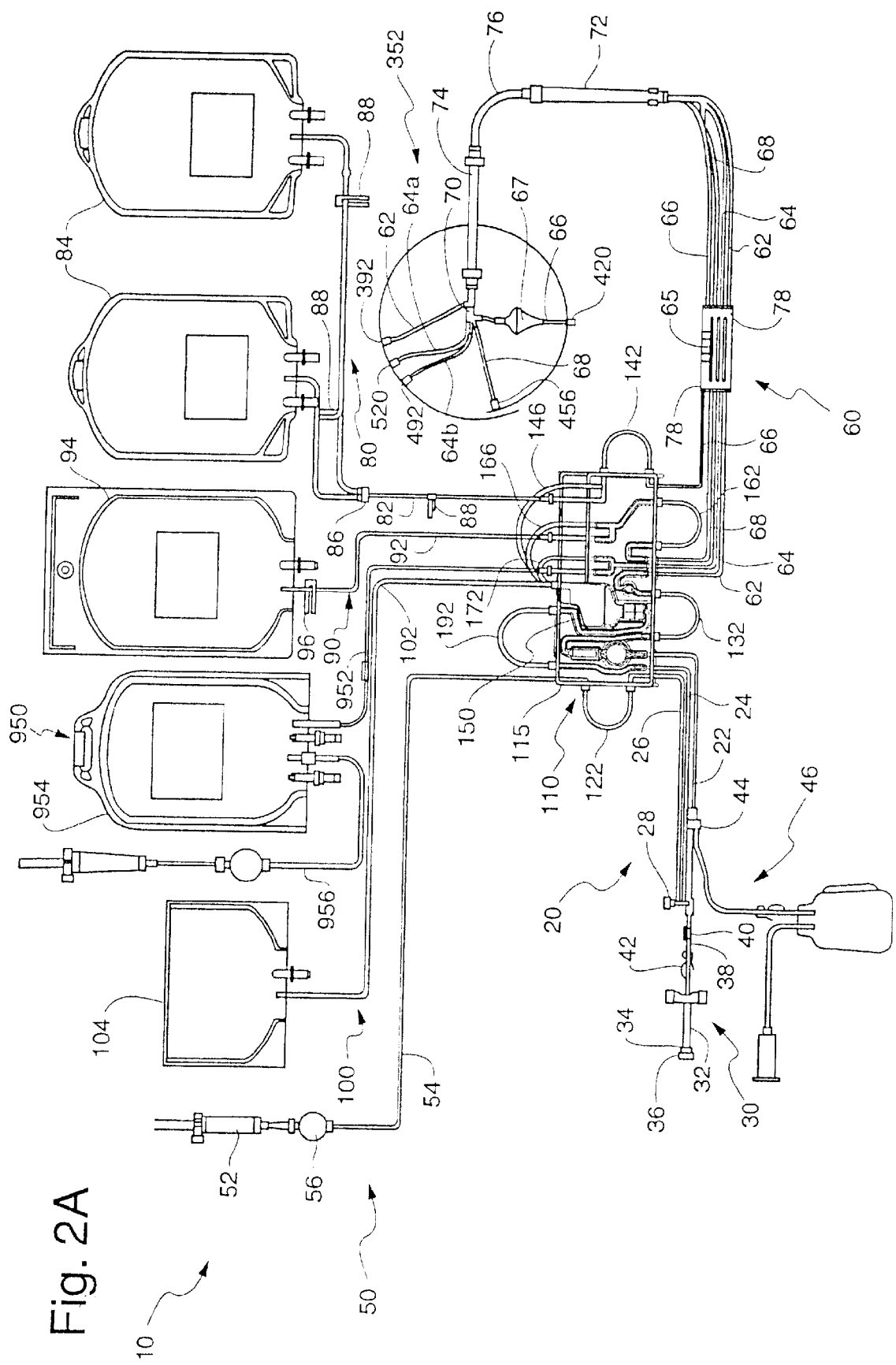
FIGS. 2A–2B illustrate an alternative extracorporeal tubing circuit and cassette assembly thereof for use in the system of FIG. 1.
Figure 2B:
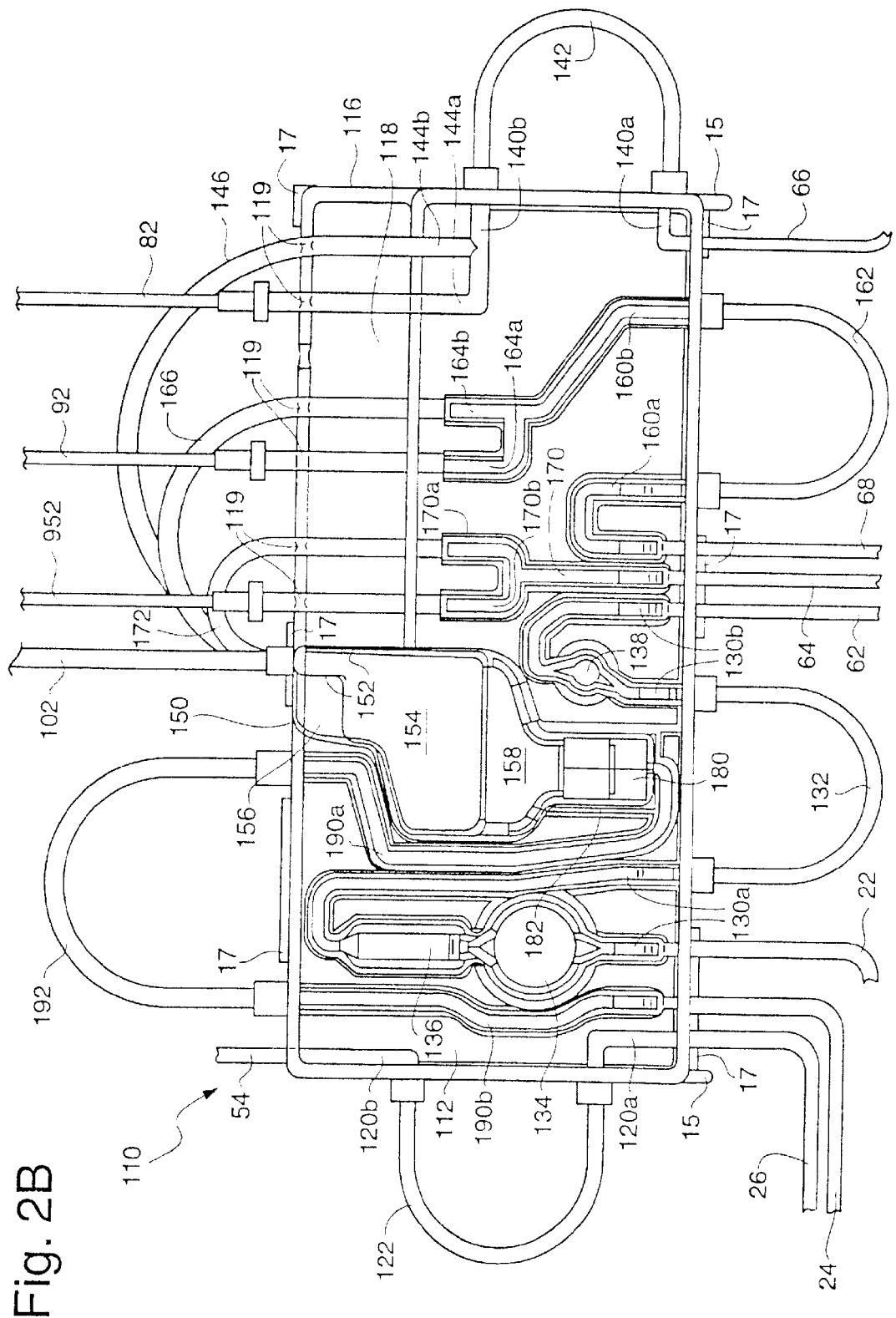

As illustrated in the alternative embodiments shown in FIGS. 2A–2D, a blood-primable extracorporeal tubing circuit 10 preferably includes a cassette assembly 110 and a number of tubing assemblies 20, 50, 60, 80, 90, 100, 950 and/or 960 interconnected therewith. Generally, blood removal/return tubing assembly 20 provides a single needle interface between a donor/patient 4 and cassette assembly 110, and blood inlet/blood component tubing subassembly 60 provides the interface between cassette assembly 110 and blood processing vessel 352. As shown in the embodiment of FIGS. 2A–2B, an anticoagulant tubing assembly 50, platelet collection tubing assembly 80, plasma collection tubing assembly 90, red blood cell collection assembly 950 and vent bag tubing subassembly 100 may be interconnected with cassette assembly 110. As shown alternatively in the embodiment of FIGS. 2C and 2D, a variation of RBC assembly 950 may be included, as well as a replacement fluid assembly 960 substituted generally in place of the platelet assembly 80 of the embodiment of FIGS. 2A and 2B. As will be appreciated, the extracorporeal tubing circuit 10 and blood processing vessel 352/352a are interconnected to combinatively yield a closed disposable assembly 8 for a single use. Note that differences between the two primary alternative tubing sets disclosed herein will be addressed as they arise in the course of the following description. Similarities, on the other hand, are numerous and are not uniformly described as such hereinbelow.

The blood removal/return tubing assembly 20 includes a needle subassembly 30 interconnected with blood removal tubing 22, blood return tubing 24 and anticoagulant tubing 26 via a common manifold 28. The needle subassembly 30 includes a needle 32 having a protective needle sleeve 34 and needle cap 36, and interconnect tubing 38 between needle 32 and manifold needle subassembly 30 preferably further includes a D sleeve 40 and tubing clamp positioned about the interconnect tubing 38. Blood removal tubing 22 may be provided with a Y-connector 44 interconnected with a blood sampling subassembly 46.

Pump/Valve/Sensor Assembly

Figure 3:
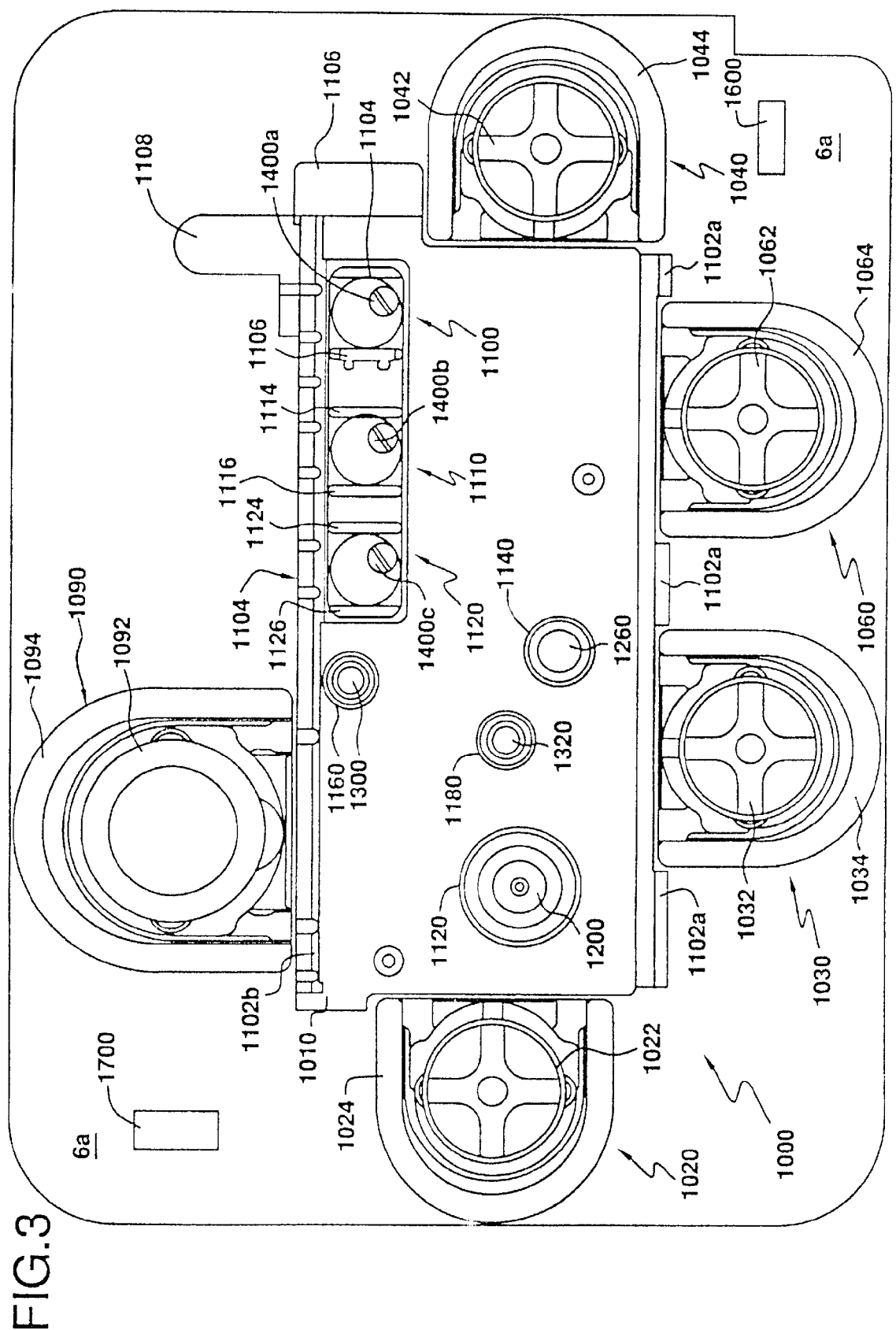
FIG. 3 is a front view of a pump/valve/sensor assembly for the system of FIG. 1.

As noted, cassette assembly 110 is mounted upon and operatively interfaces with the pump/valve/sensor assembly 1000 of blood component separation device 6 during use. The pump/valve/sensor assembly 1000 is angled upward at about 45 degrees (see FIG. 1) and as illustrated in FIG. 3 includes a cassette mounting plate 1010, and a number of peristaltic pump assemblies, flow divert valve assemblies, pressure sensors and ultrasonic level sensors interconnected to face plate 6a of blood collection device 6 for pumping, controlling and monitoring the flow of blood/blood components or replacement fluid(s) through extracorporeal tubing circuit 10 during use.

More particularly, anticoagulant pump assembly 1020 is provided to receive anticoagulant tubing loop 122, blood inlet pump assembly 1030 is provided to receive blood inlet tubing loop 132, platelet or replacement fluid inlet pump assembly 1040 is provided to receive platelet or replacement fluid tubing loop 142, plasma pump assembly is provided to receive plasma tubing loop 162, and blood return or replacement fluid delivery pump assembly 1090 is provided to receive blood return or replacement fluid delivery tubing loop 192. Each of the peristaltic pump assemblies 1030, 1040, 1060, and 1090 includes a rotor 1022, 1032, 1042, 1062 and 1092, and raceway 1024, 1034, 1044, 1064, and 1094 between which the corresponding tubing loop is positioned to control the passage and flow rate of the corresponding fluid.

Platelet divert or replacement fluid valve assembly 1100 is provided to receive platelet collector tubing 82 and platelet return tubing or replacement fluid loop 146, plasma divert valve assembly 1110 is provided to receive plasma collector tubing 92 and plasma return tubing loop 166, and RBC/plasma divert valve assembly 1120 is provided to receive RBC/plasma return tubing loop 172 and RBC/plasma collector tubing 952. As noted above, each pair of tubings for collection or return or replacement of separated blood components is disposed in a predetermined spaced relationship within window 118 of cassette assembly 110, thereby facilitating loading relative to the corresponding divert value assemblies. As will be further described, platelet divert or replacement fluid valve assembly 1100, plasma divert valve assembly 1110 and RBC/plasma divert valve assembly 1120 each preferably include a rotary occluding member 1400a, 1400b and 1400c that is selectively positionable between stationary occluding walls 1104 and 1106, 1114 and 1116, and 1124 and 1126, respectively, for diverting fluid flow through one tubing of the corresponding pairs of tubings.

Pressure sensors 1200 and 1260 (See also FIGS. 4A and 4B) are provided within pump/valve/sensor assembly 1000 to operatively engage the first and second pressure sensing modules 134 and 138 of cassette assembly 110 through openings 1120 and 1140 of cassette mounting plate 1010. Similarly, ultrasonic level sensors 1300 and 1320 (see also FIG. 5) are provided to operatively engage the blood return reservoir 150 cassette assembly 110 through openings 1160 and 1180 of cassette mounting plate 1010.

Figure 4A:
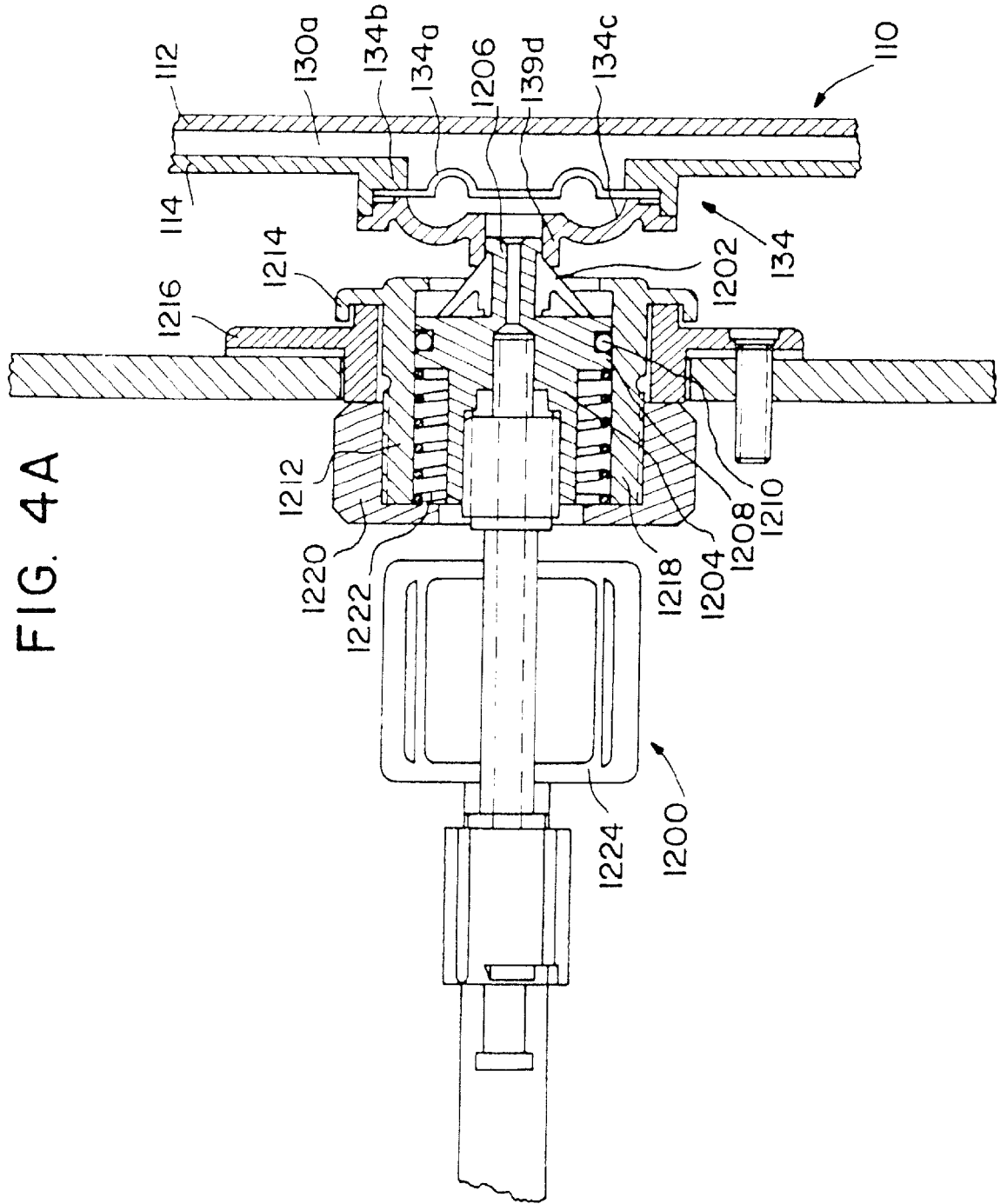

As shown in FIGS. 4A and 4B, the first and second pressure sensing modules 134, 138 of cassette assembly 110 each comprise a circular diaphragm 134a, 138a positioned on a raised cylindrical seat 134b, 138b formed into the back plate 114 of cassette assembly 110 with a ring-shaped, plastic diaphragm retainer 134c, 138c hot-welded to the raised cylindrical seats 134b, 138b to establish a seal therebetween. This arrangement allows the diaphragms 134a, 138a to be directly responsive to the fluid pressures within the first and second integral blood inlet passageways 130a, 130b, respectively, and pressure sensors 1200, 1260 to directly access the diaphragms 134a, 138a through the ring-shaped retainers 134c, 138c. By monitoring the diaphragms 134a, 138a, the pressure sensors 1200, 1260 can monitor the fluid pressure within the first and second integral blood inlet passageways 130a, 130b. In this regard, it should also be noted that since first integral blood inlet passageway 130a is in direct fluid communication with blood removal tubing 22, and since blood removal tubing 22 and blood return tubing 24 are fluidly interconnected via the common manifold 28, the first pressure sensing module 134 will be responsive to and first pressure sensor 1200 will actually sense the substantially common pressure in both the blood removal tubing 22 and blood return tubing 24 during operation.

With further regard to the first pressure sensing module 134 and first pressure sensor 1200 FIG. 4A illustrates an alternative air coupling arrangement that allows for the sensing of positive and negative pressure changes (i.e., causing outward and inward flexure of diaphragm 134a). To achieve an air seal between the first pressure sensor 1200 and first pressure sensing module 134, the sensor 1200 includes a resilient (e.g., rubber), cone-shaped engaging member 1202. The engaging member 1202 is attached to an air channel member 1204 having a nipple-end 1206 that is received by beveled cylindrical extension 134d of retainer 134c. Air channel member 1204 further includes an outer, annular projecting channel portion 1208 that contains an O-ring 1210 for sealed sliding engagement of the air channel member 1204 within housing 1212. As illustrated, housing 1212 includes ears 1214 which interface with a floating positioning member 1216 secured to the face plate 6a of blood component separation device 6. As shown, a slight clearance is provided in such interface so as to permit slight lateral movement of the engaging member 1202 and air channel member 1204 during loading of the cassette assembly 110. A threaded end 1218 of housing 1212 extends through the face plate 6a of blood component separation device 6 and receives nut 1220 thereupon, while leaving a slight clearance between the nut 1220 and face plate 6a. A spring 1222 is positioned within the housing 1212 and acts upon the annular channel portion 1208 of the air channel member 1204 to provide a spring-loaded interface between the first pressure sensor 1200 and first pressure sensing module 134. Pressure sensing transducer 1224 engages air channel member 1204 to sense positive and negative pressure changes within sensing module 134 and provide an output signal in response thereto during use. As will be further described, the output signal of pressure transducer 1224 can be employed to control the operation of blood inlet pump 1030 and blood return pump 1090 during operation.

With regard to the second pressure sensing module 138 and the second pressure sensor 1260 FIG. 4B illustrates a direct contact coupling approach that allows for sensing of positive pressure changes (i.e., causing outward flexure of diaphragm 138a). Such contact coupling facilitates loading since the precise position of the diaphragm 138a relative to the second pressure sensor 1260 is not critical. As shown, second pressure sensor 1260 includes a projecting end portion 1262 that is received by the ring retainer of sensing module 138 to directly contact diaphragm 138a. Pressure transducer 1264 is mounted relative to the face plate 6a of the blood component separation device 6 via a ring 1266 that threadingly engages a portion of pressure transducer 1264 extending through the face plate 6a. Pressure transducer 1264 provides an output signal responsive to positive pressure changes acting upon diaphragm 138a.

As shown in FIG. 5, when cassette assembly 110 is mounted on pump/valve/sensor assembly 1000, the ultrasonic level sensors 1300 and 1320 will be positioned to monitor the fluid level in the blood return or replacement fluid reservoir 150. More particularly, upper ultrasonic level sensor 1300 will be positioned in contact with the reduced top section 156 of blood return or replacement fluid reservoir 150 and lower ultrasonic level sensor 1320 will be positioned in contact with the reduced bottom section 158 of blood return or replacement fluid reservoir 150.

Ultrasonic sensors 1300, 1320 each comprise pulse/echo transducers 1302, 1322 having a contact surface (e.g., urethane) 1304, 1324 that facilitates divert dry coupling (i.e., without a gel or other like coupling medium) with the blood return or replacement fluid reservoir 150. By way of example, ultrasonic sensors may comprise model Z-11405 transducers offered by Zevex Inc. of 5175 Greenpine Drive, Salt Lake City, Utah. Pulse/echo transducers 1302, 1322 are disposed within housings 1306, 1326 for interconnection with face plate 6a of the blood component separation device 6. Housings 1326 include a flange 1308, 1328 for engaging the front of face plate 6a, and further include a threaded end 1328 that extends through the face plate 6a to receive corresponding retaining nuts 1310, 1330. A slight clearance is provided for between flanges 1308, 1328 and face plate 6a. Springs 1312, 1332 are positioned within housings 1306, 1326 to act upon the corresponding pulse/echo transducers 1302, 1332 via E-clips 1314, 1334 disposed therebetween. Such spring loading of pulse/echo transducers 1332 yields a predetermined desired loading pressure for pulse/echo transducers 1302, 1332 relative to reservoir 150 during operation (e.g., at least about 5 O-rings 1316, 1336 are provided intermediate pulse/echo transducers 1302, 1322 and housings 1306, 1326 to provide a sliding seal therebetween. Cables 1318, 1338 are interconnected to transducers 1302, 1322 to provide pulsing signals and return detected echo signals.

By gauging the presence and timing of return ultrasonic echo pulses each of the sensors 1320 can be employed to monitor the presence or absence of fluid within their corresponding echo regions within the blood return reservoir 150, and permit blood component separation device 6 to provide pump control signals in response thereto. More particularly, when return blood or replacement fluid accumulates up into the echo region of upper level sensor 1300 during blood processing, ultrasonic pulses emitted by upper level sensor 1300 will readily pass through the return blood or replacement fluid and reflect off of the opposing reservoir outside sidewall/air interface to yield echo pulses having a predetermined minimum strength that are detected by upper sensor 1300 within a predetermined time period after transmission. When such echo pulses are received, upper sensor 1300 provides a signal that is used by blood component separation device 6 to initiate operation of blood return or replacement fluid delivery pump 1090 so as to remove accumulated return blood or replacement fluid from the blood return or replacement fluid reservoir 150 and transfer the same to the donor/patient 4.

When blood return or replacement fluid delivery pump 1090 has removed return blood or replacement fluid from the reservoir 150 down into the lower echo region, ultrasonic pulses emitted by lower level sensor 1320 will not be reflected at the opposing reservoir outside sidewall/air interface to yield echo pulses having a predetermined minimum strength for detection by lower level sensor 1320 within a predetermined time period after transmission. When this occurs, lower level sensor 1320 will fail to provide corresponding signals to blood component separation device 6, and blood component separation device 6 will automatically stop blood return/replacement fluid delivery pump 1090 to stop further removal of return blood/replacement fluid from the blood return/replacement fluid reservoir 150, and return blood/replacement fluid will again begin accumulating in reservoir 150. Thus, in the blood processing mode, blood component separation device 6 will not initiate operation of blood return/replacement fluid delivery pump 1090 unless and until it receives signals from upper ultrasonic sensor(the provisions of such signals indicating the presence of return blood or replacement fluid in the upper echo region), and will thereafter automatically stop operation of blood return/replacement fluid delivery pump 1090 if it fails to receive signals from ultrasonic sensor 1320 (the failure to receive such signals indicating the absence of return blood or replacement fluid in the lower echo region).

In a preferable initial blood prime mode, whole blood may be introduced to reservoir 150 from a donor/patient 4 through blood return/replacement fluid delivery tubing 24 integral passageways 190a, 190b, and tubing loop 192 via reverse operation of blood return/replacement fluid delivery pump 1090. When such whole blood accumulates up into the echo region of lower level sensor 1320, ultrasonic pulses emitted by lower level sensor 1320 will pass through the blood and reflect off of the opposing reservoir outside sidewall/air interface to yield echo pulses having a predetermined minimum strength that are detected by lower level sensor 1320 within a predetermined time period after transmission. When such echo pulses are received in the blood prime mode, lower level sensor 1320 provides a signal that is used by blood component separation device 6 to turn off blood return/replacement fluid delivery pump 1090 and end the blood prime mode (at least insofar as the priming of the return/replacement tubing 24 and reservoir 150 is concerned). Blood component separation device 6 may then initiate the blood processing mode.

It is contemplated that ultrasonic sensors 1300, 1320 can be utilized for indicating and/or confirming the desired mounting relationship of cassette member 115 on cassette mounting plate 1010 for blood processing operations. For such purposes, if the desired mounting has been achieved, the sensors 1300, 1320 should be coupled to reservoir 150 so that ultrasonic pulses reflect off the interface between the inside surface of the back sidewall of reservoir 150 (i.e., the sidewall contacted by the sensors 1300, 1320) and contained air within reservoir 150, and be received with a predetermined minimum strength within a predetermined time period after transmission. If such echo pulses are received with respect to both ultrasonic sensors 1300, 1320, the desired loading relationship will be indicated and/or confirmed. Further, it is noted that ultrasonic sensors 1320 may be employable to sense echo pulses from the interfaces between fluid contained within the reservoir 150 and the inside surface of the outer sidewall of reservoir 150 in the upper and lower echo regions of the reservoir during operation. If such echo pulses are detectible within corresponding, predetermined time windows, corresponding signals provided by ultrasonic sensors 1300, 1320 can provide a further input for blood component separation device 6 to control operation of blood return/replacement fluid delivery pump 1090.

It should be noted that in the illustrated arrangement, the upper and lower ultrasonic sensors 1300 and 1320 advantageously operate via coupling with reduced cross-sectional portions 156 and 158 of reservoir 150. The reduced upper and lower reservoir portions 154, 158, accommodate reliable detection of echo pulses when fluid is present in the upper and lower echo regions, and the enlarged mid-portion 158 provides satisfactory return blood/replacement fluid holding capabilities.

FIG. 6 shows the preferred components of each of the platelet divert/replacement fluid valve subassembly 1100, plasma divert valve subassembly 1110 and RBC/plasma divert valve subassembly 1120. Each subassembly includes a rotary occluder member 1400 having a headed shaft member 1402 and barrel sleeve 1404 positioned thereupon and rotatable relative thereto. The subassembly further comprises a main valve shaft 1406 positioned within a valve body 1408 that is secured to face plate 6*a* of blood component separation device 6. An O-ring 1410 is provided in a recess on the main valve shaft 1406 to provide a sliding seal between main valve shaft 1406 and extensions 1412 of main valve body 1408. The main valve shaft 1406 is driven by a motor 1414 mounted on mount plate 1416 that in turn is mounted to and set off from face plate 6*a* by standoff legs 1418.

For positioning rotary occluder member 1400 for occlusion relative to one of the co-acting walls (e.g., 1104 or 1106 of the platelet divert/replacement fluid valve sub see FIG. 3) or for loading/removal of the cassette assembly 110 on the blood component separation device 6, each divert valve subassembly comprises three optical through-beam sensors 1420 (two shown) interconnected to standoff legs 1418 via support layer 1419, and an optical interrupter member 1422 interconnected to the main valve shaft Each through-beam sensor 1420 is of a U-shape configuration with a radiation source and radiation receiver disposed on opposing legs. The optical interrupter member 1422 has an inverted cup configuration with its sidewalls interposed and rotatable between the opposing legs of sensors 1420. The optical interrupter member 1422 includes a single window 1424 therethrough. As will be appreciated, the position of the rotary occluder member 1400 relative to the window 1424 of the optical interrupter 1422 is known, such that when the optical window 1424 passes between the opposing radiation source/receiver for a given optical sensor 1420, the optical sensor 1420 will provide a signal in response to the through-beam (indicating the position of the rotary occluder member 1400), and the signal is employed to control the operation of motor 1414 to dispose rotary occluder member 1400 in the desired position. To provide/route such signals, the support layer 1419 may advantageously comprise a printed circuit board. Optical sensors 1420 are preferably positioned slightly "upstream" of predetermined stop regions for occlusion or cassette loading so that motor 1414 will be able to dynamically slow down and position rotary occluder member 1400 within such regions as desired. To insure the desired positioning for occlusion, however, stops 1426 are provided on main valve shaft 1406 to co-act with cross-pin 1428 interconnected to main valve shaft 1406 to insure stop positioning of rotary occluder member 1400 relative to the desired occluding wall.

Each of the occluding walls 1104 and 1106, 1114 and 1116, and 1124 and 1126, are provided with arcuate recesses (not shown) for receiving the rotatable barrel sleeve of rotary occluder members 1400*a*, 1400*b* and 1400*c*. By way of example, such arcuate recesses may have an arc length of 20 degrees and provide a tolerance range for positioning the rotary occluder members 1400*a*, 1400*b*, 1400*c* to achieve the desired tubing occlusion. As illustrated in FIG. 3, occluding wall 1106 may be provided with a resilient pad to best accommodate the use of thin-walled PVC tubing for platelet collector tubing 82. Further, and as noted above, thin-walled PVC tubing may be employed for plasma collector tubing 92 and RBC/plasma collector tubing 952, and corresponding resilient pads (not shown) may be provided on occluding walls 1114 and 1124. In this regard, given the relatively high-spring rate of thin-walled PVC tubing, the use of resilient pads in connection therewith increases the wearability of the thin-walled PVC tubing.

In order to establish an initial predetermined set position of the cassette assembly 110 relative to the pump/valve/sensor assembly 1000, the cassette assembly 110 includes downwardly extending corner positioning tabs 15 and top and bottom edge lips 17 110 that engage corresponding lower channel projections 1102*a* on cassette mounting plate 1010 and upper channel projections 1102*b* on a pivotable spring-loaded interlock member 1104 that extends across the top edge of cassette mounting plate 1010. The interlock member 1104 is spring-loaded to positively engage cassette assembly 110 upon loading via a spring positioned within housing 1106, and is provided with a tab 1108 for pivotable movement during cassette loading against the spring loading pressure. Preferably, interlock member 1104 is disposed relative to the raceway 1094 of return/replacement fluid delivery pump assembly 1090, such that when cassette assembly 110 is fully loaded for operation on blood component separation device 6, raceway 1094 will physically restrict interlock member 1104 from being pivoted, thereby advantageously restricting removal and/or movement of cassette assembly 110 during use.

Figure 7:
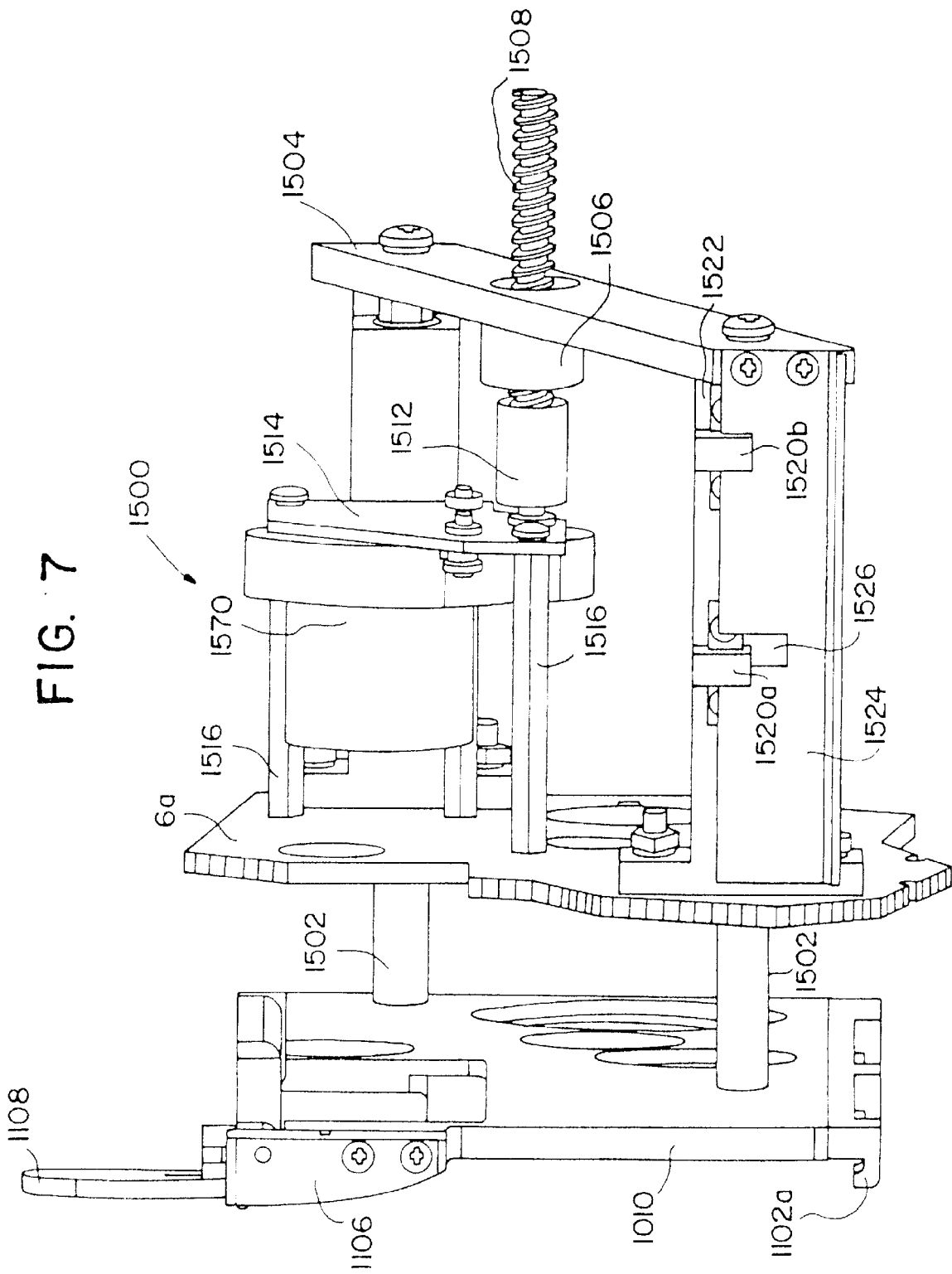
FIG. 7 illustrates a loading assembly for a cassette mounting plate of the pump/valve/sensor assembly of FIG. 3.

After cassette assembly 110 has been secured on the cassette mounting plate 1010, a loading assembly 1500 retracts the cassette mounting plate 1010 towards face plate 6*a* of the blood component separation device 6 to establish the above-noted, fully-loaded pump, valve and sensor relationships. As illustrated in FIG. 7, loading assembly 1500 includes two posts 1502 upon which cassette mounting plate 1010 is supportably interconnected. The posts 1502 extend through the face plate 6*a* of blood collection device 6 and are interconnected to a cross-connect member 1504. A drive nut 1506 is secured to cross-connect member 1504 and engages a drive screw 1508. The drive screw 1508 is in turn rotatably interconnected to a drive motor 1510 via coupling 1512, the drive 1510 being mounted on a platform 1514 which is supportively interconnected to face plate 6a via standoff legs 1516. The drive motor 1510 operates to turn drive screw 1508 so as to cause cross-connect member 1504 and posts 1502 to selectively move cassette mounting plate 1010 perpendicularly towards face plate 6a during loading procedures and perpendicularly away from face plate 6a for unloading of the cassette assembly 110.

To establish the desired position of cassette mounting plate 1010, U-shaped optical through-beam sensors 1520a and 1520b are mounted on post bearing holders 1522 and an optical occluder member 1524 having a window 1526 is interconnected to the cross-connect member 1504. Each of the U-shaped optical sensors 1520a, 1520b includes a radiation source and radiation receiver positioned on opposing extending legs, and the optical occluder member 1524 extends between such legs. Since the relative positions between cassette mounting plate 1010 and optical sensors 1520a, 1520b are known, by detecting the passage of radiation through window 1526 using optical sensors 1520, and providing a signal responsive thereto, the position of cassette mounting plate 1010 for loading and unloading can be automatically established. For example, when a through-beam is received by optical sensor 1520b, a signal will be provided to stop motor 1510 in a position wherein cassette assembly 110 will be fully loaded on the pump/valve/sensor assembly 1000 for operation.

To confirm such loaded condition, first and second pressure sensors 1200 and 1260 and upper and lower ultrasonic sensors 1300 and 1320 may be employed. For example, predetermined minimum pressure values can be established and actual pressures measured for each of the first and second pressure sensors 1200 and 1260 to confirm the desired loading of cassette assembly 110. Further, and of particular interest, ultrasonic sensors 1300 and 1320 can be advantageously employed to confirm the desired loading, since upon proper coupling to reservoir 150 echo pulses should be reflected off of the internal sidewall/air interface with a predetermined minimum strength within a predetermined time period as noted above.

It should be noted that drive motor 1510 preferably includes a number of reduction gears with the last gear being operatively associated with a slip clutch plate to limit the maximum amount of force that may be applied by cassette mounting plate 1010 (e.g., to an object between cassette mounting plate 1010 and face plate 6a). Relatedly, it is preferable to include control capabilities wherein during a load cycle if the window 1526 of optical occluder 1524 has not moved from its position within the first optical pass through sensor 1520a to a position within the second optical pass through sensor 1520b within a predetermined time period, drive motor 1510 will automatically either stop or reverse operations.

To summarize the loading process, loading assembly 1500 initially disposes cassette mounting plate 1010 in an extended position. With the cassette mounting plate 1010 in such extended position, interlock member 1104 is pivoted away from cassette mounting plate 1010 and cassette assembly 110 is positioned on cassette mounting plate 1010 with bottom edge lips 17 of cassette assembly 110 being received by lower channel projections 1102a of cassette mounting plate 1010 and, upon return pivotal movement of interlock member 1104, top edge lips 17 of cassette assembly 110 being engaged by upper channel projections 1102b on interlock member 1104. Loading assembly 1500 is then operated to retract cassette mounting plate 1010 from its extended position to a retracted position, wherein tubing loops 132, 162, 142, 192 of cassette assembly 110 are automatically positioned within the corresponding peristaltic pump assemblies 1020, 1030, 1060, 1040 and 1090. For such purposes, the rotors of each of the peristaltic pump assemblies are also operated to achieve loaded positioning of the corresponding tubing loops. Further, it should be noted that for loading purposes, the rotary occluder members 1400a, 1400b and 1400c of the divert valve assemblies 1100, 1110 and 1120 are each positioned in an intermediate position so as to permit the corresponding sets of tubing to be positioned on each side thereof.

Upon retraction of the cassette mounting plate 1010, spring-loaded, ultrasonic sensors 1300 and 1320 will automatically be coupled to reservoir 150 and first and second pressure sensors 1200 and 1260 will automatically couple to first and second pressure sensing modules 134 and 138 of cassette assembly 110. In this fully-loaded, retracted position, the cassette assembly 110 will be restricted from movement or removal by the above-noted physical restriction to pivotal movement of interlock member 1104 provided by raceway 1094 of return pump assembly 1090.

It is also noted that during loading of cassette assembly 110 on the blood component separation device 6, cuvette 65 (whether disposed in cassette 110 or in line tubing line 66 or 68) is positioned within an RBC spillover detector 1600 (e.g., an optical sensor for detecting the presence of any red blood cells in the separated platelet or plasma fluid stream and providing a signal response thereto) provided on the face plate 6a. Detector 1600 may also be used for set identification as described hereinabove. Similarly, a portion of anticoagulant tubing 54 is positioned within an AC sensor 1700, e.g., an ultrasonic sensor for confirming the presence of anticoagulant and providing a signal in the absence thereof) also provided in face plate 6a.

To unload cassette assembly 110 after use, the occluding members 1400a, 1400b and 1400c f each divert value assembly are again positioned in an intermediate position between the corresponding occluding walls and loading assembly 1500 is operated to move cassette mounting plate 1010 from its retracted position to its extended position. Contemporaneously, the rotors of the various peristaltic pump assemblies are operated to permit the corresponding tubing loops to exit the same. In the extended position, the interlock member 1104 is pivoted out of engagement with cassette assembly 110 and cassette assembly 110 is removed and disposed of.

Operation of Extracorporeal Tubing Circuit and Pump/Valve/Sensor Assembly

In an initial blood prime mode of operation, blood return/replacement fluid delivery pump 1090 is operated in reverse as mentioned above, to transfer whole blood from the donor/patient 4 through blood removal/return tubing assembly 20, integral blood return passageway 190, blood return/replacement fluid delivery tubing loop 192 and into reservoir 150. Contemporaneously with and/or prior to the reverse operation of blood return/replacement fluid delivery pump 1090, anticoagulant peristaltic pump 1020 is operated to prime and otherwise provide anticoagulant from anticoagulant tubing assembly 50, through anticoagulant integral passageway 120, and into blood removal tubing 22 and blood return tubing 24 via manifold 28. When lower level ultrasonic sensors 1320 senses the presence of the whole blood in reservoir 150 a signal is provided and blood component separation devices 6 tops blood return/replacement fluid delivery peristaltic pump 1090. As will be further discussed, during the blood prime mode blood inlet pump 1030 is also operated to transfer blood into blood inlet integral passageway through blood inlet tubing loop 132 and into blood inlet/blood component tubing assembly 60 to prime the blood processing vessel 352.

During the blood prime mode, vent bag assembly 100 receives air from reservoir 150. Relatedly, the occluding members 1400a, 1400b, 1400c of divert assemblies 1100, 1110, 1120 are each preferably positioned to divert flow to the reservoir 150. It should also be noted that to facilitate blood priming, the cassette assembly 110 is angled upward at about 45 degrees in its loaded position, and the integral passageways of cassette member 115 are disposed so that all blood and blood component and replacement fluid inlet paths provide for a bottom-to-top blood flow.

In the blood processing mode, the blood inlet peristaltic pump 1030, platelet/replacement fluid inlet peristaltic pump 1040 and plasma peristaltic pump 1060 are operated generally continuously (except as described hereinbelow in further detail, e.g., when operating with replacement fluids, at least the blood inlet pump 1030 is stopped during delivery of replacement fluids to the donor/patient 4), and the occluding members 1400a, 1400b, 1400c are positioned for collection or return of corresponding blood components, as desired. During a blood removal submode, blood return/replacement fluid delivery peristaltic pump 1090 is not operated so that whole blood will pass into blood removal/return tubing assembly 20 and transferred to processing vessel 352 via the cassette assembly 110 and blood inlet/blood component tubing assembly 60. In the blood removal submode, uncollected blood components are transferred from the processing vessel 352 to cassette assembly 110, and uncollected components are passed into and accumulate in reservoir 150 up to a predetermined level at which upper level ultrasonic sensor 1300 provides signals used by blood component separation device 6 to end the blood removal submode and initiate a blood return or replacement fluid delivery submode. More particularly, a blood return or replacement fluid delivery submode is initiated by forward operation of blood return/replacement fluid delivery peristaltic pump 1090. In this regard, it should be appreciated that in the blood return or replacement fluid delivery submode the volume transfer rate of return blood or replacement fluid through blood return/replacement fluid tubing loop 192 utilizing blood return/replacement fluid delivery peristaltic pump 1090 is established by blood component separation device 6, according to a predetermined protocol, to be greater than the volume transfer rate through blood inlet tubing loop 132 utilizing blood inlet peristaltic pump 1030 (again, in certain red blood cell collection protocols and/or, if using replacement fluid delivery, the blood inlet pump 1030 is stopped when return/delivery pump 1090 is operating). As such, the accumulated blood or replacement fluid in reservoir 150 is transferred into the blood return/replacement fluid delivery tubing of blood removal/return tubing assembly 20 and back into the donor/patient 4. During the blood processing mode, when the accumulated return blood or replacement fluid in reservoir 150 is removed down to a predetermined level, lower level ultrasonic sensor 1320 will fail to provide signals to blood component separation device 6, whereupon blood component separation device 6 will automatically stop blood return/replacement delivery peristaltic pump 1090 to end the blood return/replacement delivery submode. This automatically serves to reinitiate the blood removal submode since blood inlet peristaltic pump 1030 continuously operates (or restarts as described herein in replacement delivery use).

During the blood processing mode, pressure sensor 1200 senses negative/positive pressure changes within the blood removal tubing 22 blood return/replacement delivery tubing 26, via first integral blood inlet passageway 130a. Such monitored pressure changes are communicated to blood component separation device 6 which in turn controls blood inlet pump 1030 and return pump 1090 so as to maintain fluid pressures within predetermined ranges during the blood removal and the blood return submodes. Specifically during the blood removal submode, if a negative pressure is sensed that exceeds (i.e., is less than) a predetermined negative limit value, then blood component separation device 6 will slow down operation of blood inlet pump 1030 until the sensed negative pressure is back within an acceptable range. During the blood return/replacement delivery submode, if a positive pressure is sensed that exceeds (i.e., is greater than) a predetermined positive limit value, then blood component separation device 6 will preferably slow down operation of blood return/replacement delivery pump 1090 until the sensed positive pressure is back within an acceptable range.

Pressure sensor 1260 monitors the positive pressure within the second integral blood inlet passageway 130b and blood inlet tubing 62. If such sensed positive pressure exceeds a predetermined maximum value, blood component separation device 6 will initiate appropriate responsive action, including, for example, slowing or stoppage of the centrifuge and peristaltic pumps.

During the blood processing mode, blood component separation device 6 controls the operation of anticoagulant pump 1020 according to a predetermined protocol and responsive to signals provided by AC sensor 1700 (e.g., indicating a depleted anticoagulant source). Also, blood component separation device 6 also controls the operation of divert assemblies 1110, 1120 according to predetermined instructions and further pursuant to any detect signals provided by RBC spillover detector 1600. In the latter regard, if an RBC spillover in the separated platelet or plasma stream is detected, blood component separation device 6 will automatically cause occluder member 1400a to divert the separated platelet or plasma stream to the return reservoir 150 until the RBC spillover has cleared, thereby keeping red blood cells from undesirably passing into the corresponding platelet or plasma collector tubing assembly 80 or 90. Similarly, if a spillover detector is used with the replacement fluid line and anything other than a replacement fluid is detected (in the embodiment of FIGS. 2c–2d) then the device 6 will take appropriate action, such as halting the procedure (even before it starts, e.g.) and prompting for a change in tubing set or fluid connection, In normal operation, whole blood will pass through needle assembly 30, blood removal tubing 22, cassette assembly 110 and blood inlet tubing 62 to processing vessel 352. As will be further described in detail, the whole blood will then be separated into blood components in vessel 352. In the embodiment of FIGS. 2A–2B, a platelet stream will pass out of port 420 of the vessel, through platelet tubing 66, back through cassette assembly 110, and will then be either collected in platelet collector assembly 80 or diverted to reservoir 150. Similarly, separated plasma will exit vessel 352 through port to plasma tubing 68 back through cassette assembly 110, and will then either be collected in plasma tubing assembly 90 or diverted to reservoir 150. Further, red blood cells (and potentially white blood cells) may pass through ports 492 and 520 of vessel 352 through RBC/plasma tubing 64, through cassette assembly 110 and into reservoir 150. Alternatively, during RBC collection procedures as described below, separated RBCs will be delivered to RBC/plasma collector tubing assembly 950 for collection. Also, alternatively, according to the embodiment of FIGS. 2C–2D, during product collection, replacement fluid will be passed through inlet tubing line 962, cassette 110 and into the reservoir 150, and only RBCs and plasma will be passed out of vessel 352 through corresponding ports 520 and 456 for collection and/or return as described in more detail below.

As noted above, when uncollected platelets, plasma, and RBC/plasma (and potentially white blood cells) and/or replacement fluid(s) have accumulated in reservoir 150 up to upper ultrasonic level sensor 1300, operation of return/delivery peristaltic pump 1090 will be initiated to remove the noted blood or replacement components from reservoir 150 and transfer the same back to the donor/patient 4 via the return/delivery tubing 24 and needle assembly 20. When the fluid level in the reservoir 150 drops down to the level of the lower ultrasonic level sensor 1320, the return/delivery peristaltic pump 1090 will automatically turn off reinitiating the blood removal submode (including restarting the blood inlet pump 1030, if necessary). The cycle between blood removal and blood return/replacement delivery submodes will then continue until a predetermined amount of platelets, RBCs or other collected blood components have been harvested.

In one embodiment, reservoir 150 and upper and lower ultrasonic sensors 1300 and 1320 are provided so that, during the blood processing mode, approximately 50 milliliters of return blood/replacement fluid will be removed from reservoir 150 during each blood return/replacement delivery submode and accumulated during each blood removal submode. Relatedly, in such embodiment, lower and upper level triggering by ultrasonic sensors 1300 and 1320 occurs at fluid volumes of about 15 milliliters and 65 milliliters, respectively, within reservoir 150. For such embodiment, it is also believed desirable to provide for a volume transfer operating rate range of about 30 to 300 milliliters/minute through blood return/replacement delivery tubing loop 192 utilizing return/delivery pump 1090, and a volume transfer operating rate range of either zero or about 20 to 140 milliliters/minute through blood inlet tubing loop 132 utilizing blood inlet pump 1030. Additionally, for such embodiment a negative pressure limit of about –250 mmHg and positive pressure limit of about 350 mmHg is believed appropriate for controlling the speed of inlet pump 1030 and return/delivery pump 1090, respectively, in response to the pressures sensed in first pressure sensing module 134. A positive pressure limit of about 1350 mmHg within second sensing module 138 is believed appropriate for triggering slow-down or stoppage of the centrifuge and pumps.

Channel Housing

The channel assembly 200 is illustrated in FIGS. 8A–23B and includes a channel housing 204 which is disposed on the rotatable centrifuge rotor assembly 568 (FIGS. 1 and 24) and which receives a disposable blood processing vessel 352 or 352a. Referring more specifically to FIGS. 8–15, the channel housing 204 has a generally cylindrically-shaped perimeter 206 with a diameter of preferably no more than about 10 inches to achieve a desired size for the blood component separation device 6 (e.g., to enhance its portability). An opening 328 extends longitudinally through the channel housing 204 and contains an axis 324 about which the channel housing 204 rotates. The channel housing 204 may be formed from materials such as delrin, polycarbonate, or cast aluminum and may include various cut-outs or additions to achieve weight reductions and/or rotational balance.

Figure 15:
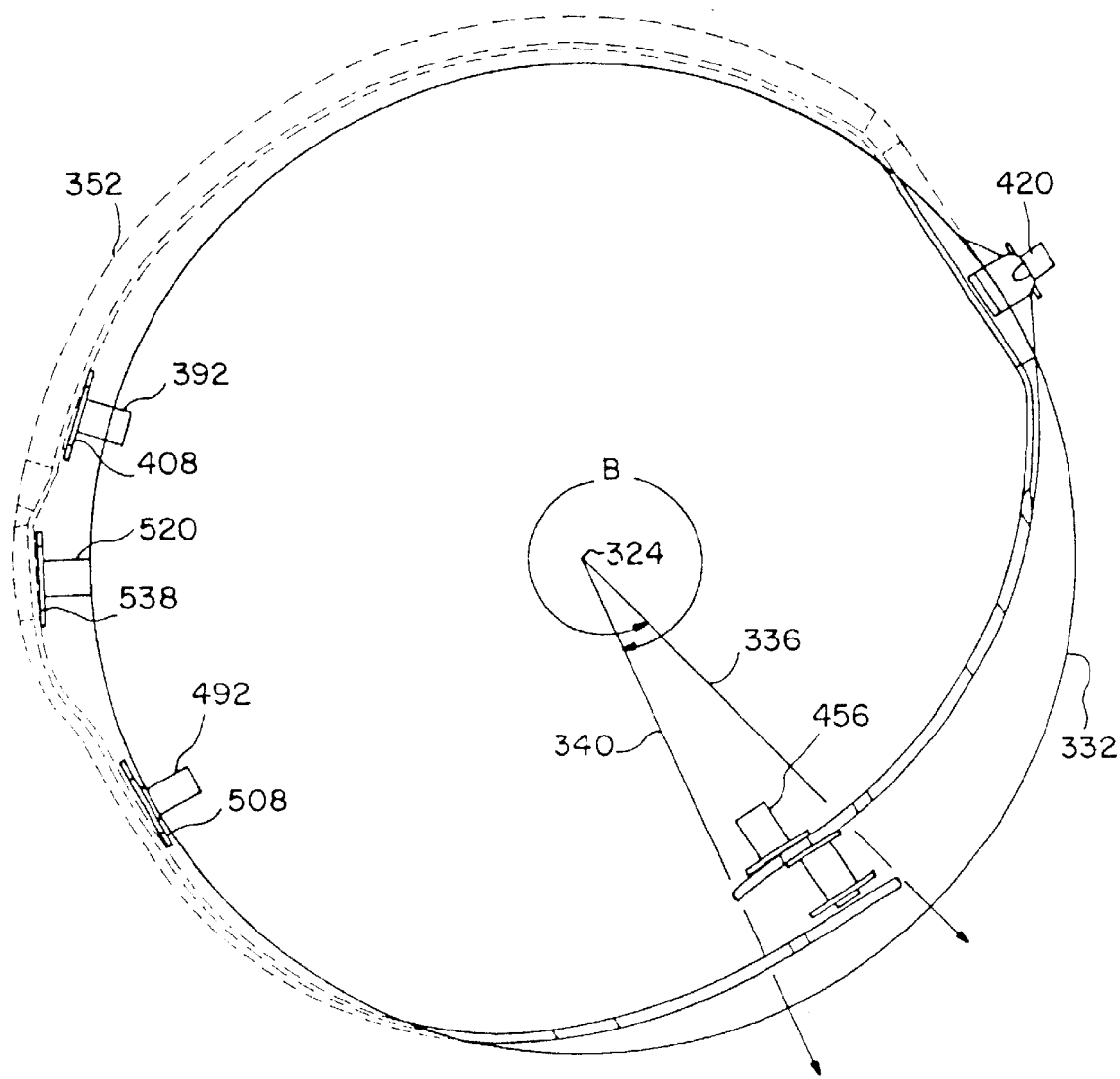
FIG. 15 is a top view of the channel of FIG. 8A illustrating a ratio of the plasma volume to the red blood cell volume.

The primary function of the channel housing 204 is to provide a mounting for the blood processing vessel 352 or 352a such that the blood may be separated into the blood component types in a desired manner. In this regard, the channel housing 204 includes a generally concave channel 208 in which the blood processing vessel 352 or 352a is positioned. The channel 208 is principally defined by an inner channel wall 212, an outer channel wall 216 which is radially spaced from the inner channel wall 212, and a channel base 220 which is positioned therebetween. The channel 208 also extends from a first end 284 generally curvilinearly about a rotational axis 324 of the channel housing 204 to a second end 288 which overlaps with the first end 284 such that a continuous flow path is provided about the rotational axis 324. That is, the angular disposition between the first end of 284 the channel 208 and the second end 288 of the channel 208 is greater than 360 degrees and up to about 390 degrees, and in the illustrated embodiment is about 380 degrees. Referring to FIG. 15, this angular disposition is measured by the angle B (beta), along a constant radius arc, between a first reference ray 336 which extends from the rotational axisto 324 the first end 284, and a second reference ray 340 which extends from the rotational axis 324 to the second end 288 of the channel 208.

The blood processing channel vessel 352 or 352a is disposed within the channel 208. Generally, the channel 208 desirably allows blood to be provided to the blood processing vessel 352/352a during rotation of the channel housing 204, to be separated into its various blood component types by centrifugation, and to have various blood component types removed from the blood processing vessel 352/352a during rotation of the channel housing F 204. or instance, the channel 208 is configured to allow for the use of high packing factors (e.g., generally a value reflective of how "tightly packed" the red blood cells and other blood component types are during centrifugation and as will be discussed in more detail below). Moreover, the channel 208 also desirably interacts with the blood processing vessel 352/352a ring centrifugation (e.g., by retaining the blood processing vessel 352/352a in the channel 208 and by maintaining a desired contour of the blood processing vessel I 352/352a. n addition, the channel 208 allows for a blood priming of the blood processing vessel 352/352a (i.e., using blood as the first liquid which is provided to the blood processing vessel 352/352a in an apheresis procedure).

The above-identified attributes of the channel 208 are provided primarily by its configuration. In this regard, the channel housing 204 includes a blood inlet slot 224 which is generally concave and which intersects the channel 208 at its inner channel wall 212 in substantially perpendicular fashion (e.g., the blood inlet slot 224 interfaces with the inner channel wall 212). A blood inlet port assembly 388 to the interior of the blood processing vessel 352/352a is disposed in this blood inlet slot 224 such that blood from the donor/patient 4 may be provided to the blood processing vessel 352/352a when in the channel 208. In order to retain a substantially continuous surface along the inner channel wall 212 during an apheresis procedure and with the blood processing vessel 352/352a being pressurized, namely by reducing the potential for the blood inlet port assembly 388 deflecting radially inwardly within the blood inlet slot 224, a recess 228 is disposed on the inner channel wall 212 and contains the end of the blood inlet slot 224 (e.g., FIG. 14A). This recess 228 receives a shield 408 which is disposed about the blood inlet port assembly 388 on the exterior surface of the blood processing vessel 352/352a as will be discussed in more detail below.

Figure 8A:
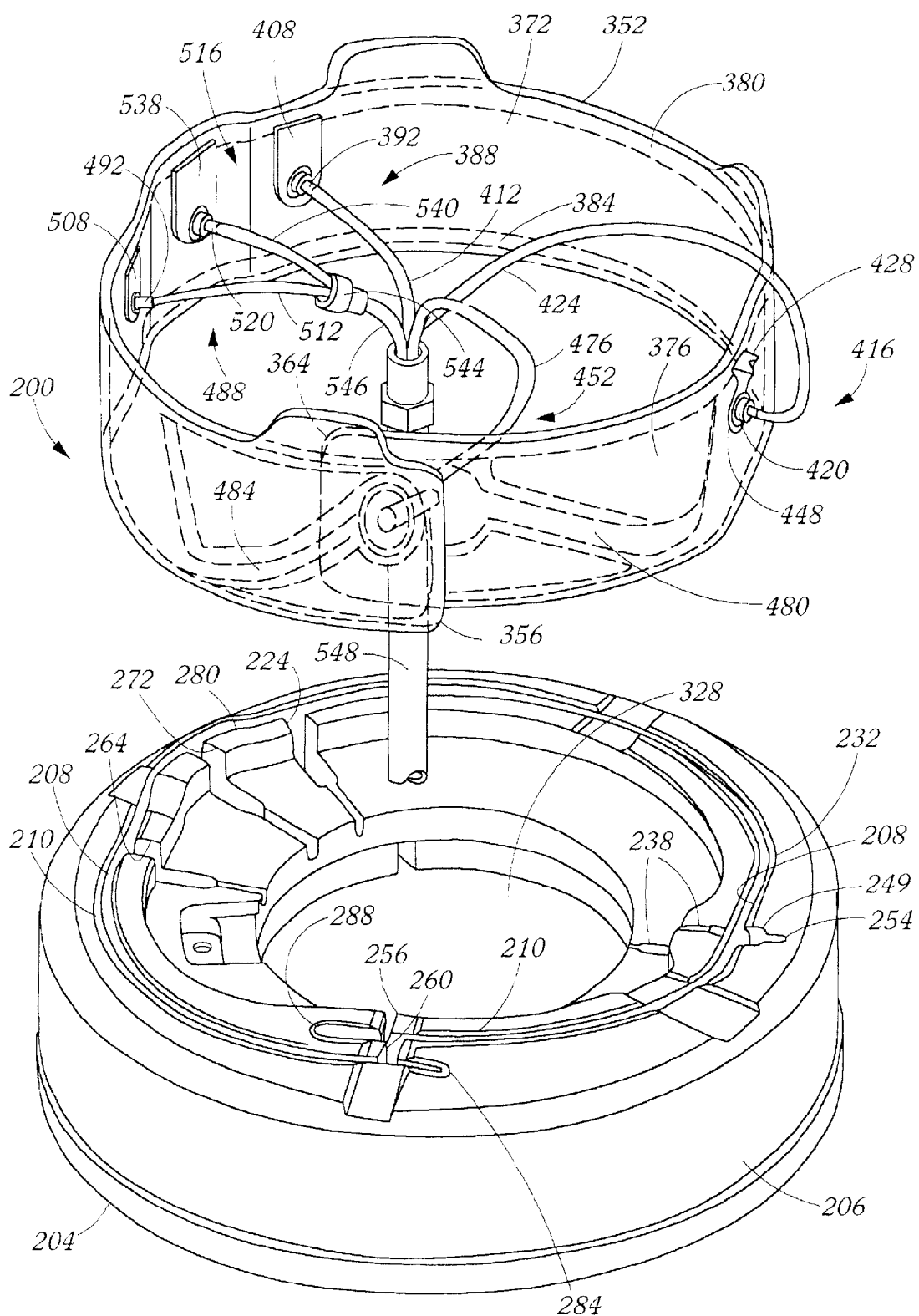
FIG. 8A is an exploded, isometric view of the channel assembly from the system of FIG. 1 together with a vessel such as that shown in FIGS. 2A–2B.
Figure 8B:
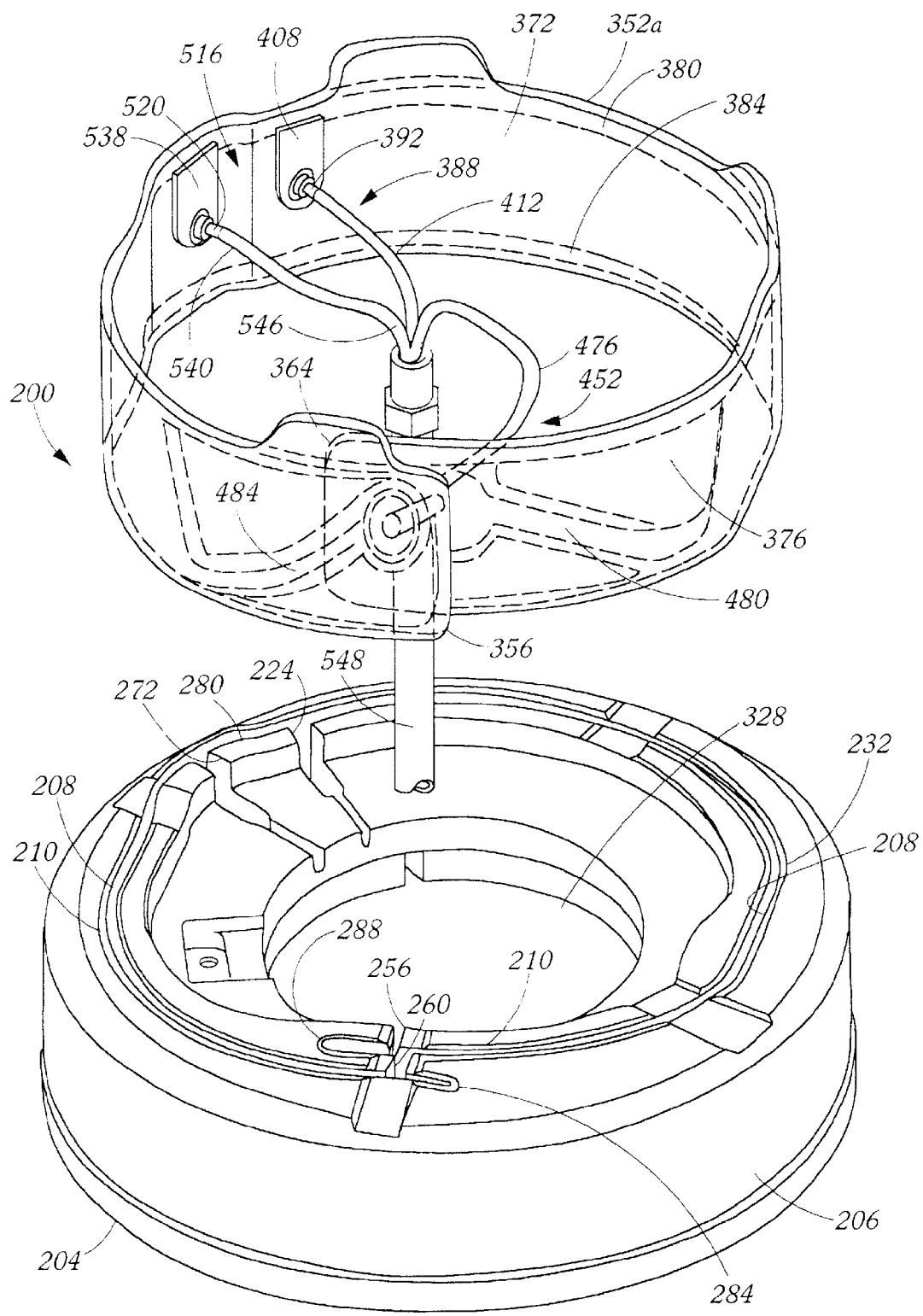
FIG. 8B is an exploded, isometric view of a channel assembly as from the system of FIG. 1 together with the vessel of FIGS. 2C–2D.
Figure 9A:
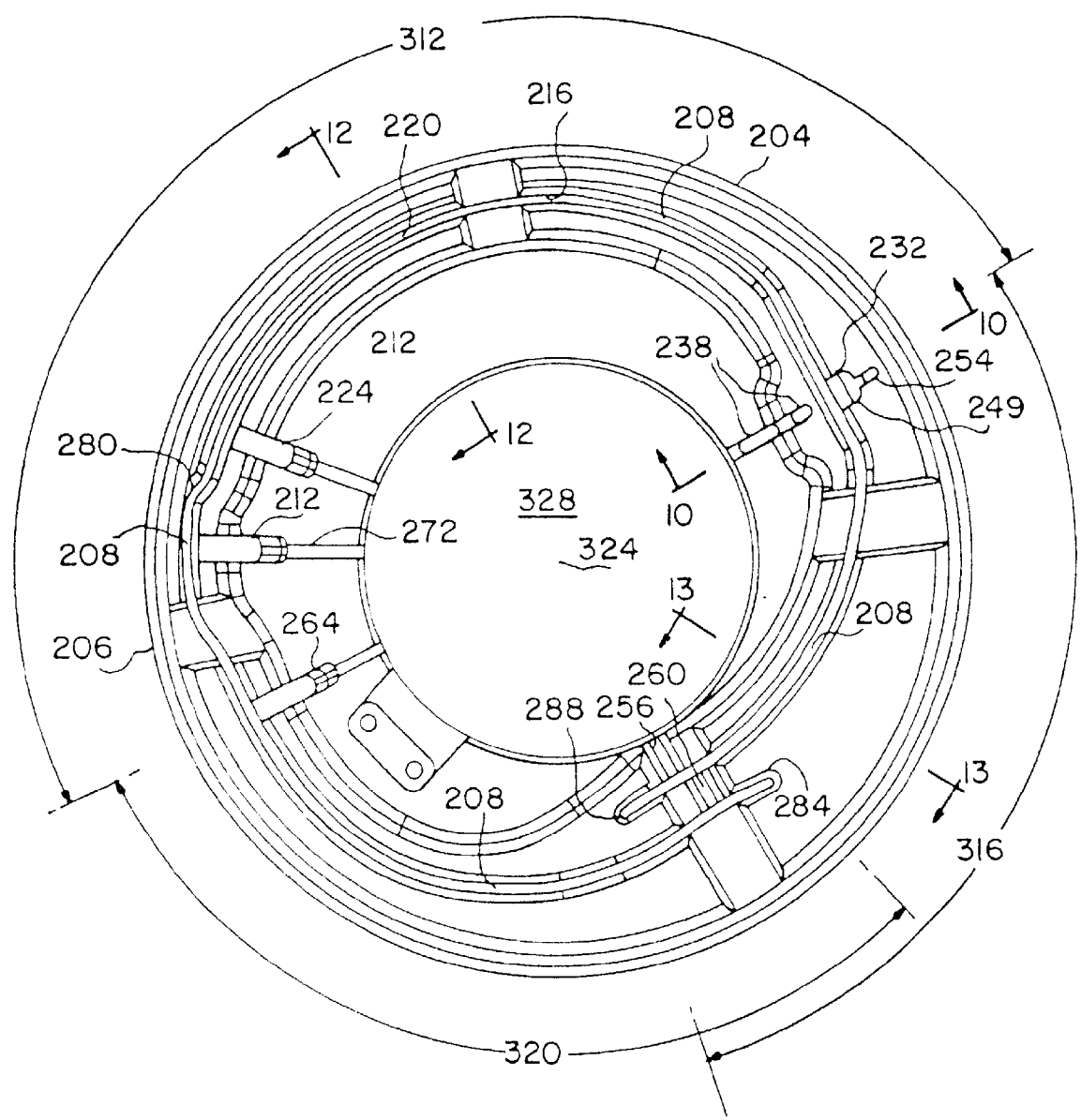
FIGS. 9A–9B are top views of the channel housing from the channel assembly of FIG.
Figure 9B:
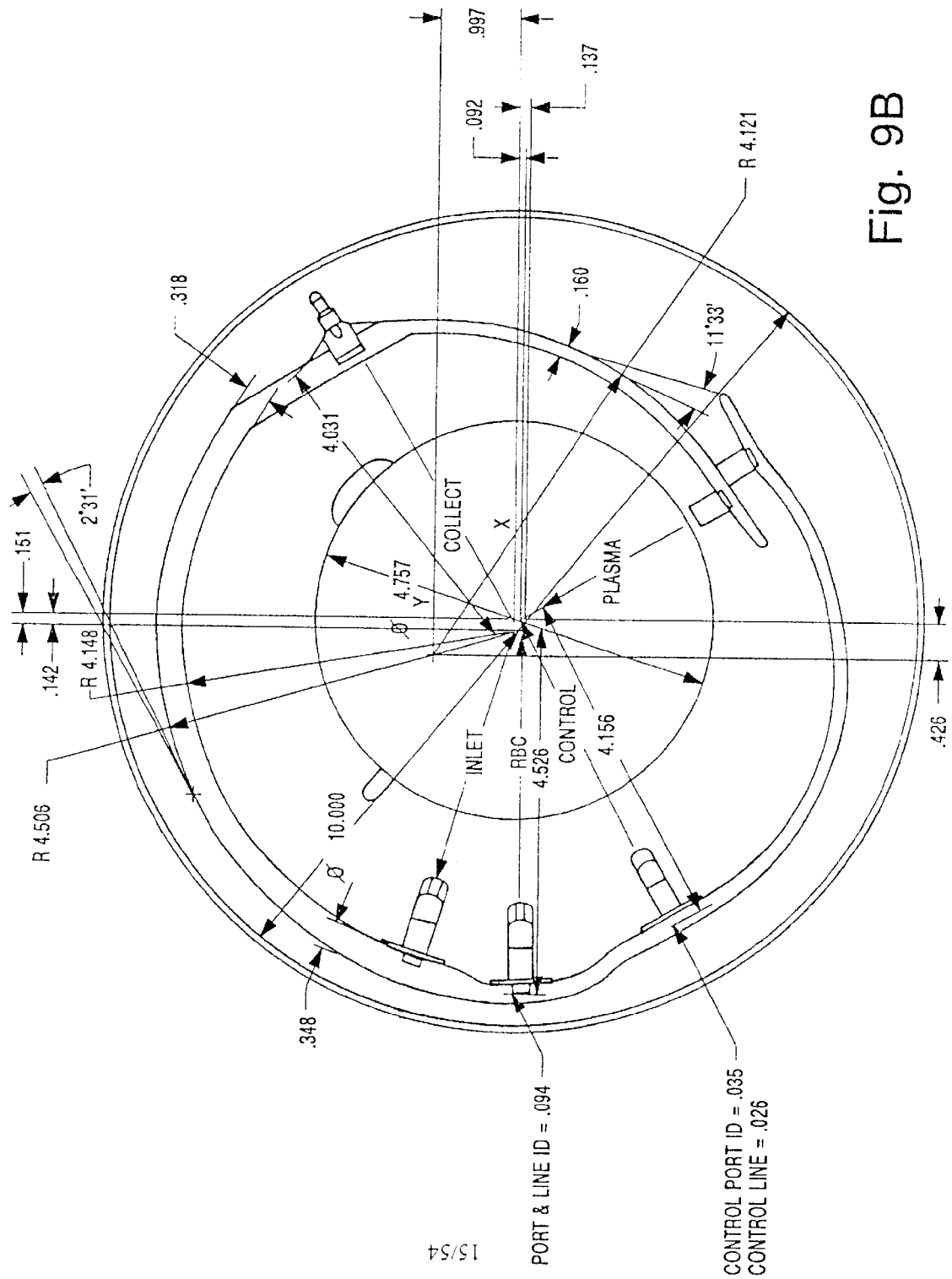
Figure 10:
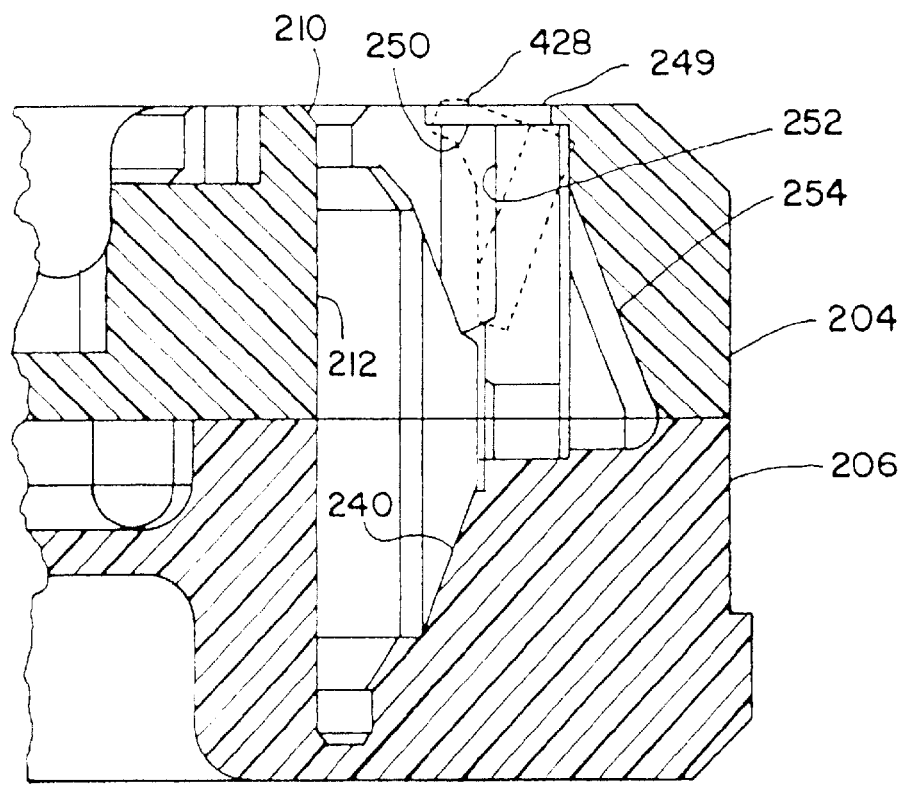
FIG. 10 is a cross-sectional view taken along line 10—10 of FIG. 9A.
Figure 11A:
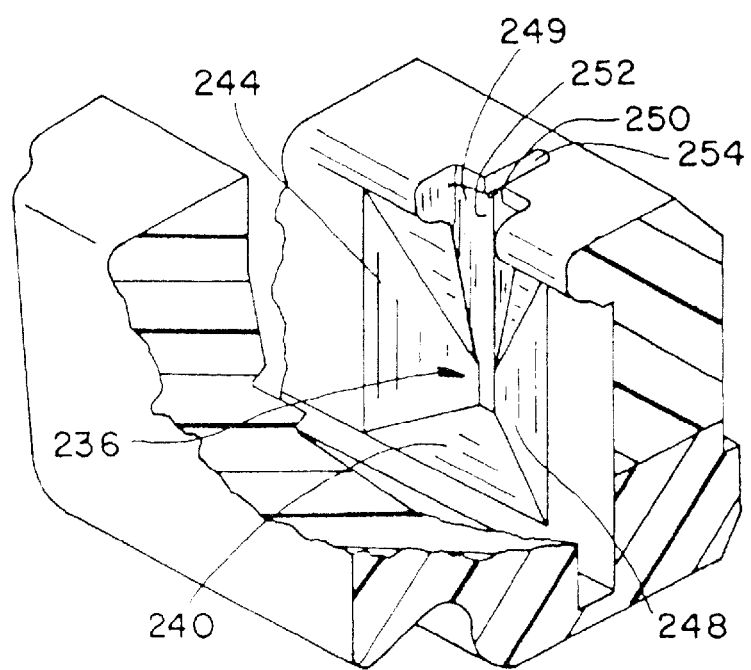
FIG. 11A is a cutaway, isometric view of the platelet collect well region of the channel housing of FIG. 8A.

As illustrated in FIGS. 8–9, an RBC dam 232 of the channel 208 is disposed in a clockwise direction from the blood inlet slot 224 and whose function is to preclude RBCs and other large cells such as WBCs from flowing in a clockwise direction beyond the RBC dam 232. Generally, the surface of the RBC dam 232 which interfaces with the fluid containing volume of the blood processing vessel 352/352a may be defined as a substantially planar surface or as an edge adjacent the collect well 236. At least in that portion of the channel 208 between the blood inlet port 224 and the RBC dam 232, blood is separated into a plurality of layers of blood component types including, from the radially outermost layer to the radially innermost layer, red blood cells ("RBCs"), white blood cells ("WBCs"), platelets, and plasma. The majority of the separated RBCs are removed from the channel 208 through an RBC outlet port assembly 516 which is disposed in an RBC outlet slot 272 associated with the channel 208, although at least some RBCs may be removed from the channel 208 through a control port assembly 488 which is disposed in a control port slot 264 associated with the channel 208.

The RBC outlet port slot 272 is disposed in a counterclockwise direction from the blood inlet slot 224, is generally concave, and intersects the channel 208 at its inner channel wall 212 in substantially perpendicular fashion (e.g., the RBC outlet slot 272 interfaces with the inner channel wall 212). An RBC outlet port assembly 516 to the interior of the blood processing vessel 352/352a is disposed in this RBC outlet slot 272 such that separated RBCs from the apheresis procedure may be continually removed from the blood processing vessel 352/352a when in the channel 208 (e.g., during rotation of the channel housing 204). In order to retain a substantially continuous surface along the inner channel wall 212 during an apheresis procedure and with the blood processing vessel 352/352a being pressurized, namely by reducing the potential for the RBC outlet port assembly 516 deflecting radially inwardly within the RBC outlet slot 272, a recess 276 is disposed on the inner channel wall 212 and contains the end of the RBC outlet slot 272 (e.g., FIGS. 14A, 14B). This recess 276 receives a shield 538 which is disposed about the RBC outlet port assembly 516 on the exterior surface of the blood processing vessel 352/352a as will be discussed in more detail below. These above elements are preferably substantially similar in both of the alternative embodiments as shown in FIGS. 8A and 8B.

In the embodiment of FIG. 8A, there is a control port slot 264 is disposed in a counterclockwise direction from the RBC outlet slot 272, is generally concave, and intersects the channel 208 at its inner channel wall 212 in substantially perpendicular fashion (e.g., the control port slot 264 interfaces with the inner channel wall 212). A control port assembly 488 to the interior of the blood processing vessel 352 (see FIG. 8A) is disposed in the control port slot 264 (e.g., FIGS. 14A and C). In order to retain a substantially continuous surface along the inner channel wall 212 during an apheresis procedure and with the blood processing vessel 352 being pressurized, namely by reducing the potential for the control port assembly 488 deflecting radially inwardly within the control port slot 264, a recess 268 is disposed on the inner channel wall 212 and contains the end of the control port slot 264. This recess 268 receives a shield 508 which is disposed about the control port assembly 488 on the exterior surface of the blood processing vessel 352 as will be discussed in more detail below.

In the embodiment of FIG. 8B, the RBC outlet port 520 acts also as the interface control outlet port, and there is thus no corresponding control port assembly 488 in this embodiment. The interface control features hereof will be described further below.

The portion of the channel 208 extending between the control port slot 264 and the RBC dam 232 may be characterized as the first stage 312 of the channel 208. The first stage 312 is configured to remove primarily RBCs from the channel 208 by utilizing a reverse flow in relation to the flow of platelet-rich and/or platelet-poor plasma (depending upon the corresponding use of respective vessels 352 or 352a) through the channel 208 which is in a clockwise direction. In this regard, the outer channel wall 216 extends along a curvilinear path from the RBC dam 232 to the blood inlet slot 224 generally progressing outwardly away from the rotational axis 324 of the channel housing 204. That is, the radial disposition of the outer channel wall 216 at the RBC dam 232 is less than the radial disposition of the outer channel wall 216 at the blood inlet slot 224. The portion of the RBC outlet slot 272 interfacing with the channel 208 is also disposed more radially outwardly an the portion of the blood inlet slot 224 which interfaces with the channel 208.

In the first stage 312, blood is separated into a plurality of layers of blood component types including, from the radially outermost layer to the radially innermost layer, red blood cells ("RBCs"), white blood cells ("WBCs"), platelets, and plasma. As such, the RBCs sediment against the outer channel wall 216 in the first stage 312. By configuring the RBC dam 232 such that it is a section of the channel 210 which extends further inwardly toward the rotational axis 324 of the channel housing 204, this allows the RBC dam 232 to retain separated RBCs and other large cells as noted within the first stage 312. That is, the RBC dam 232 functions to preclude RBCs from flowing in a clockwise direction beyond the RBC dam 232. And, in the embodiment of FIGS. 2C–2D and 8B, it is preferable that, as described below, all blood components except platelet-poor plasma are precluded from flowing in a clockwise direction beyond the RBC dam 232.

Separated RBCs and other large cells as noted are removed from the first stage 312 utilizing the above-noted configuration of the outer channel wall 216 which induces the RBCs and other large cells as noted to flow in a counterclockwise direction, e.g., generally opposite to the flow of inlet blood into and through the first stage 312). Specifically, separated RBCs and other large cells as noted flow through the first stage 312 counter clockwise along the outer channel wall 216, past the blood inlet slot 224 and the corresponding blood inlet port assembly 388 on the blood processing vessel 352/352a, and to an RBC outlet slot 272. In the embodiment of FIG. 8A, in order to reduce the potential for counterclockwise flows other than separated RBCs being provided to the control port assembly 488 disposed in the control port slot 264 (e.g., such that there is a sharp demarcation or interface between RBCs and plasma proximate the control port slot 264 as will be discussed in more detail below), a control port dam 280 of the channel 208 is disposed between the blood inlet slot 224 and the RBC outlet slot 272. That is, preferably no WBCs, nor any portion of a buffy coat, disposed radially adjacent to the separated RBCs, is allowed to flow beyond the control port dam 280 and to the control port slot 264. The "buffy coat" includes primarily WBCs, lymphocytes, and the radially outwardmost portion of the platelet layer. As such, substantially only the separated RBCs and plasma are removed from the channel 208 in the FIG. 8A embodiment via the RBC control slot 264 to maintain interface control as noted. Contrarily, in the embodiment of FIGS. 2C–2D and 8B, all of these layers (except the platelet poor plasma) are retained behind the dam 232 and are also flowed back counter clockwise to the RBC/control outlet 520 where all such components, even the platelet poor plasma flowing thereto in a clockwise direction from the second stage (see below), is removed through the RBC/control outlet 520. Preferably, as will be described below, the RBC/plasma interface is maintained at the radial level of the RBC/control outlet 520; and thus, the dam 280 does not foreclose any separated component flow thereto.

The flow of RBCs to the control port assembly 488 in the embodiment of FIGS. 2A–2B and 8A, is typically relatively small. Nonetheless, the ability for this flow is highly desired in that the control port assembly 488 functions in combination with the RBC outlet port assembly 516 to automatically control the radial position of an interface between separated RBCs and the "buffy coat" in relation to the RBC dam 232 by controlling the radial position of an interface between separated RBCs and plasma in relation to the control port assembly 488. The control port assembly 488 and RBC outlet port assembly 516 automatically function to maintain the location of the interface between the separated RBCs and the buffy coat at a desired radial location within the channel 208 which is typically adjacent the RBC dam 232 such that there is no spillover of RBCs or the buffy coat beyond the RBC dam 232. This function is provided by removing separated RBCs from the channel 208 at a rate which reduces the potential for RBCs and the other large cells as noted flowing beyond the RBC dam 232 and contaminating the platelet collection.

Separated platelets, again in the embodiment of FIGS. 2A–2B and 8A, which are disposed radially inwardly of the RBC layer and more specifically radially inwardly of the buffy coat, flow beyond the RBC dam 232 with the plasma (e.g., via platelet-rich plasma) in a clockwise direction. In the FIG. 8B embodiment, there is no platelet collection performed, and, preferably only platelet-poor plasma flows over the dam 232. Forcing the interface further radially outwardly by making the RBC port 520 also act as the control port achieves this restriction, i.e., the platelets do not get close enough to the dam 232 to flow thereover in this other embodiment. However, in the embodiment of FIG. 8A, a generally funnel-shaped platelet collect well 236 is disposed in a clockwise direction from the RBC dam 232 and is used to remove platelets from the channel 208 in the platelet-rich plasma. The configuration of the platelet collect well 236 is defined by only part of the outer channel wall 216. The portion of the platelet collect well 236 defined by the configuration of the outer channel wall 216 includes a lower face 240, a left side face 244, and a right side face 248. These faces 240, 244, 248 are each substantially planar surfaces and taper generally outwardly relative to the rotational axis 324 and inwardly toward a central region of the platelet collect well 236.

The remainder of the platelet collect well 236 (FIG. 8A) is defined by the blood processing vessel 352 when loaded in the channel 208, namely a generally triangularly-shaped, which is disposed above the platelet outlet port assembly 416 to the interior of the blood processing vessel 352 and discussed in more detail below. A platelet support recess extends further radially outwardly from those portions of the platelet collect well 236 defined by the configuration of the outer channel wall 216 and primarily receives the support 428 associated with the platelet collect port assembly 416. Generally, the upper portion of the support 428 is disposed below and engages an upper lip 252 of the platelet support recess 249, while portions of the fourth face 444 of the support 428 are seated against the two displaced shoulders 252. This positions the support 428 when the blood processing vessel 352 is pressurized to direct platelets toward the platelet collect port assembly 416.

The outer channel wall 216 is further configured to receive the platelet collect tube An upper platelet collect tube recess 254 and a lower platelet collect tube recess 255 are disposed yet further radially outwardly from the platelet support recess 249 to provide this function. As such, the platelet collect tube 424 may extend radially outwardly from the outer sidewall 376 of the blood processing vessel 352, extend upwardly through the lower platelet collect tube recess 255 and the upper platelet collect tube recess 254 behind or radially outwardly from the support 428, and extend above the channel housing 204.

Platelet-poor plasma continues to flow in a clockwise direction through the channel 208 after the platelet collect well 236 (FIG. 8A), or after the dam 232 (in the embodiment of FIG. 8B), and may be removed from the channel 208. In this regard, the channel 208 further includes a generally concave plasma outlet slot 256 (FIGS. 8A and 8B) which is disposed proximate the second end 288 of the channel 208 and intersects the channel 208 at its inner channel wall 212 in substantially perpendicular fashion (i.e., the plasma outlet slot 256 interfaces with the inner channel wall 212). A plasma outlet port assembly 452 to the interior of the blood processing vessel 352 is disposed in this plasma outlet slot 256 such that plasma may be continually removed from the blood processing vessel 352/352a during an apheresis procedure (e.g., during continued rotation of the channel housing 204). This plasma may be collected and/or returned to the donor/patient 4 as described in further detail below.

Figure 2C:
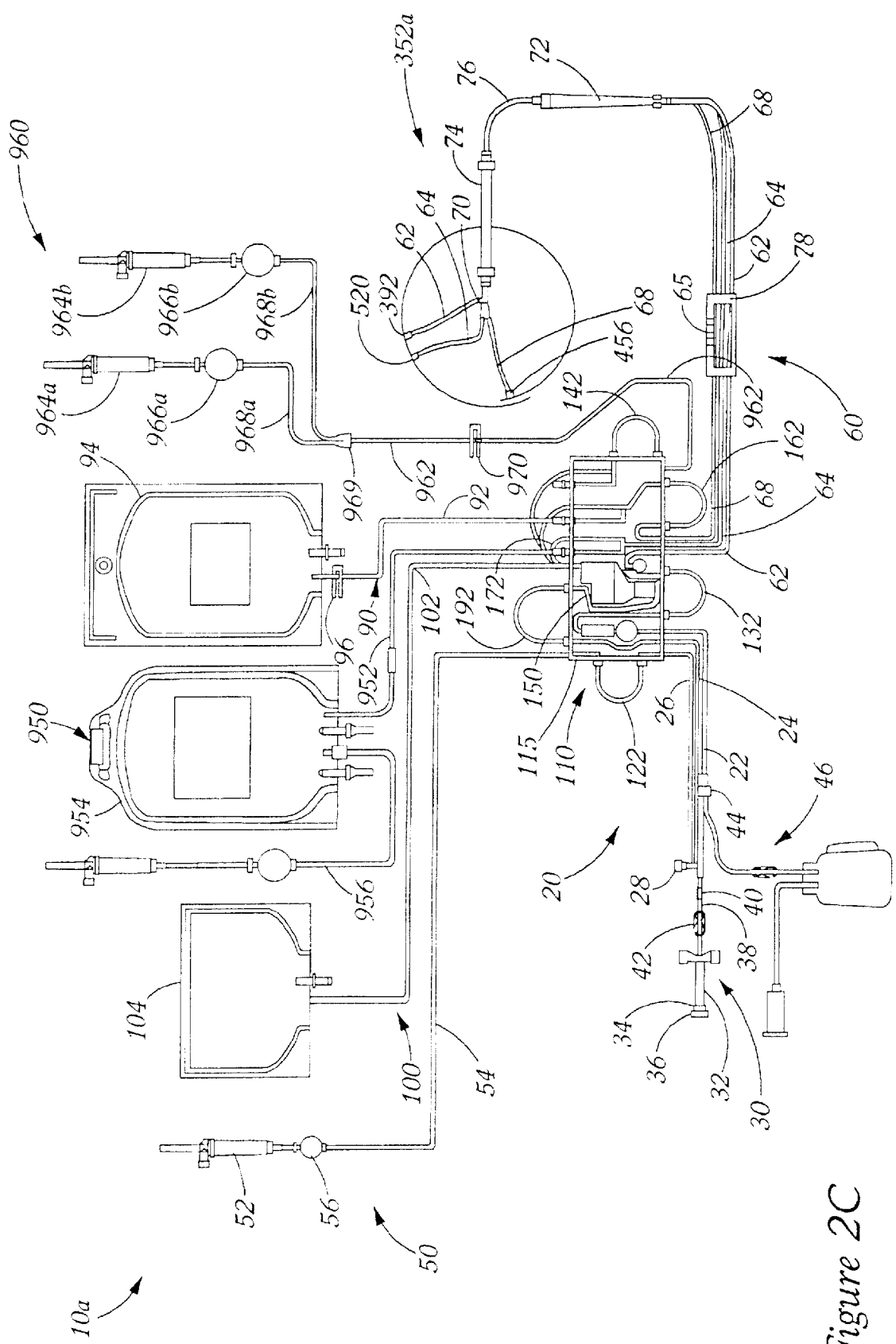
FIGS. 2C–2D illustrate another alternative extracorporeal tubing circuit and cassette assembly thereof for use in the system of FIG. 1.
Figure 2D:
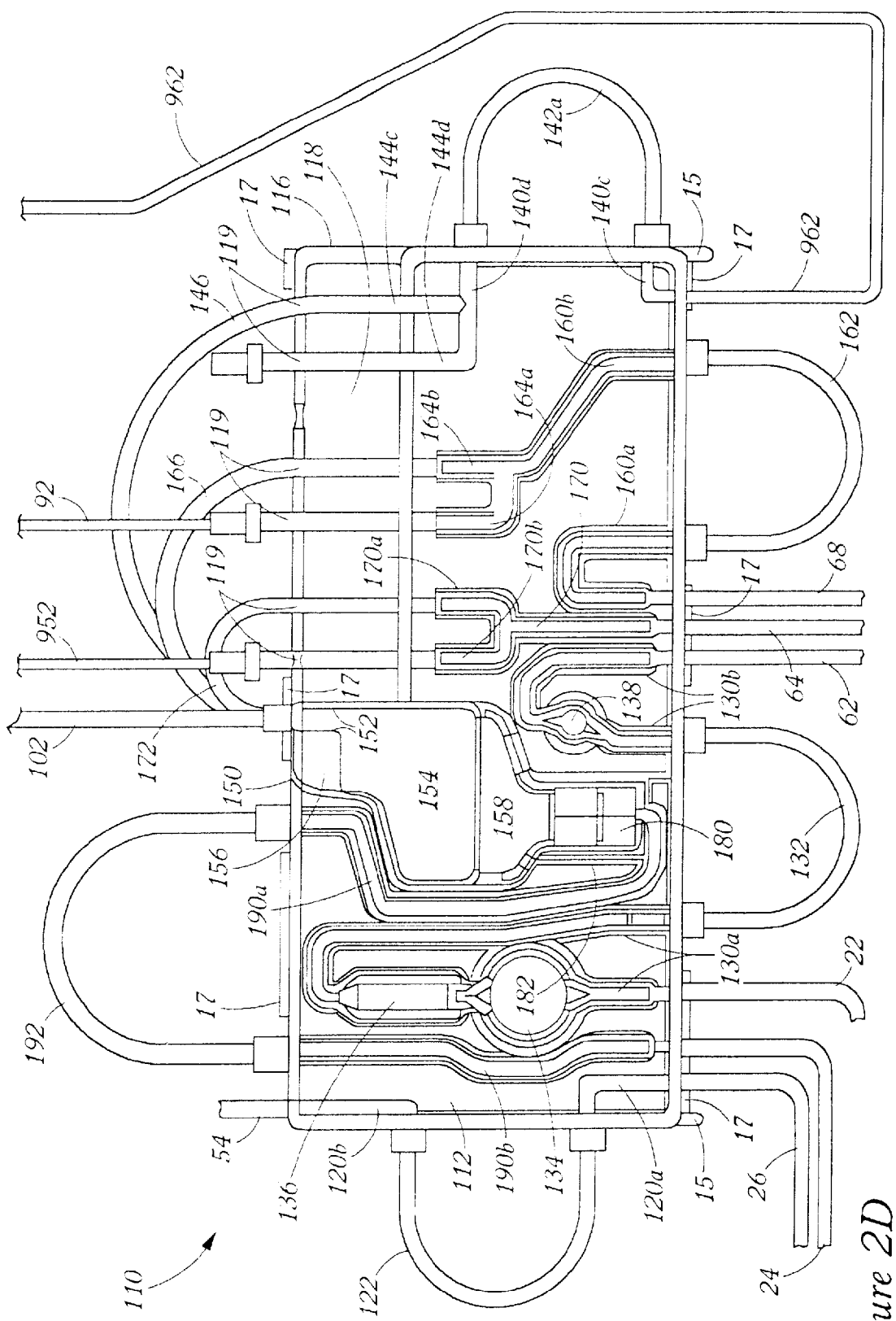

In order to increase the number of platelets that are separated and removed from the vessel 352 in the embodiment of FIG. 8A, in a given apheresis procedure, the configuration of the channel 208 between the platelet collect well 236 and the plasma outlet slot 256 may be such that platelets which separate from plasma in this portion of the channel 208 actually flow in a counterclockwise direction back towards the platelet collect well 236 for removal from the channel 208. This may be provided by configuring the outer channel wall 216 such that it extends generally curvilinearly about the rotational axis 324 from the platelet collect well 236 to the plasma outlet slot 256 progressing generally inwardly toward the rotational axis 324 of the channel housing 204. Consequently, the portion of the channel 208 including the platelet collect well 236 and extending from the platelet collect well 236 to the second end 288 may be referred to as a second stage 316 of the channel 208. In the embodiment of FIGS. 2C–2D and 8B where there is no platelet collect well, the second stage 316 extends from the top of the dam 232 to the plasma outlet port 456 (see FIG. 2C).

The channel 208 is also configured to provide platelet-poor plasma to the control port slot 264 in the FIG. 8A embodiment, and to the RBC/control port slot 272 in the FIG. 8b embodiment. Thus platelet-poor plasma flows to the control port assembly 488 (FIG. 8A) or RBC/control port 520 (FIG. 8B) in order to assist in automatically controlling the interface between the RBCs and the buffy coat or plasma in relation to the RBC dam I 232. n this regard, the first end 284 of the channel 208 is interconnected with the second end 288 of the channel 208 by a connector slot 260. With the first connector 360 and second connector 368 of the blood processing vessel 352/352a being joined, they may be collectively disposed in this connector slot 260. As such, a continuous flowpath is provided within the blood processing vessel 352/352a and, for purposes of the automatic interface control feature, RBCs may flow to the control port slot 264 (FIG. 8A) in a counterclockwise direction and plasma may flow to the control port slot 264 (FIG. 8A) or RBC/control port slot 272 (FIG. 8B) in a clockwise direction. The portion of the channel 208 extending from the first end 284 to the respective control port slots 264/272 may be referred to as a third stage 320 of the channel A 208.

As noted above, the configuration of the channel 208 is desirable/important in a number of respects. As such, the dimensions of one embodiment of the channel 208 are provided herein and which may contribute to the functions of the channel 208 discussed below. The dimensions for one embodiment of the channel 208 are identified on FIG. 9B. All radii and thicknesses, etc., are expressed in inches.

One of the desired attributes of the channel 208 is that it facilitates the loading of the blood processing vessel 352/352a therein. This is provided by configuring the channel 208 to include a chamfer 210 on both sides of the channel 208 along the entire extent thereof. Generally, the chamfer 210 extends downwardly and inwardly toward a central portion of the channel 208 as illustrated, for instance, in FIGS. 12–13. In this embodiment the angle of this chamfer 210 ranges from about 30 degrees to about 60 degrees relative to horizontal, and preferably is about 45 degrees. Moreover, the configuration of the channel 208 retains the blood processing vessel 352/352a within the channel 208 throughout the apheresis procedure. This is particularly relevant in that the channel housing 254 is preferably rotated a relatively high rotational velocities, such as about 3,000 RPM.

Another desirable attribute of the channel 208 is that it provides a self-retaining function for the blood processing vessel 352/352a. The configuration of the channel 208 in at least the first stage 312, and preferably in the region of the platelet collect well 236 (FIG. 8A) and in the region of the RBC dam 232 as well, is configured such that the upper portion of the channel 208 includes a restriction (e.g., such that the upper part of the channel 208 in this region has a reduced width in relation to a lower portion thereof). Although this configuration could also be utilized in the portion of the second stage 316 disposed between the platelet collect well 236 or dam 232 and the plasma outlet slot 256, in the illustrated embodiment the width or sedimentation distance of the channel 208 in this region is less than the width or sedimentation distance of the channel 208 throughout the entire first stage 312. This use of a "reduced width" can itself sufficiently retain the blood processing vessel 352/352a in the channel 208 in the "reduced-width" portion of the second stage 316 such that the inner channel wall 212 and outer channel wall 216 in this portion of the second stage 316 may be generally planar and vertically extending surfaces.

Figure 12:
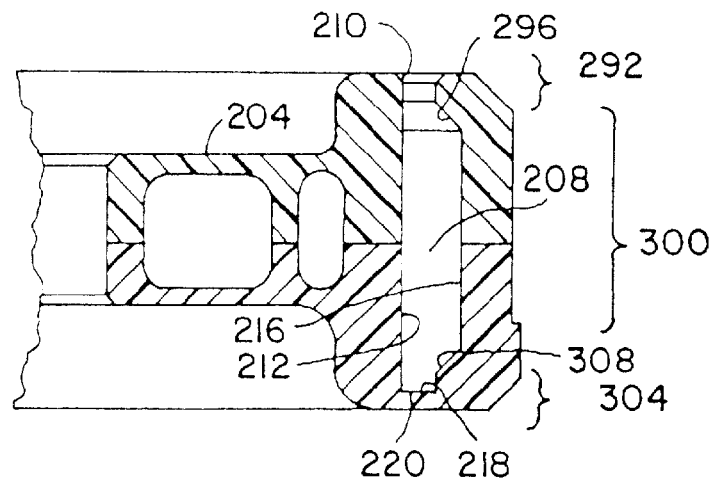
FIG. 12 is a cross-sectional view of the channel housing taken along line 12—12 in FIG.
Figure 13:
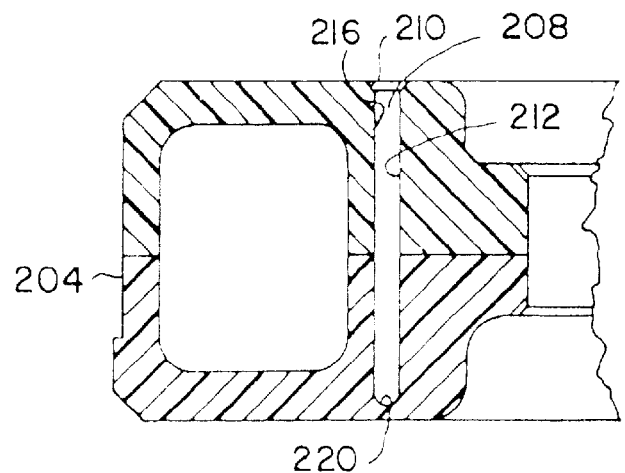
FIG. 13 is a cross-sectional view of the channel housing taken along line 13—13 in FIG.
Figure 14C:
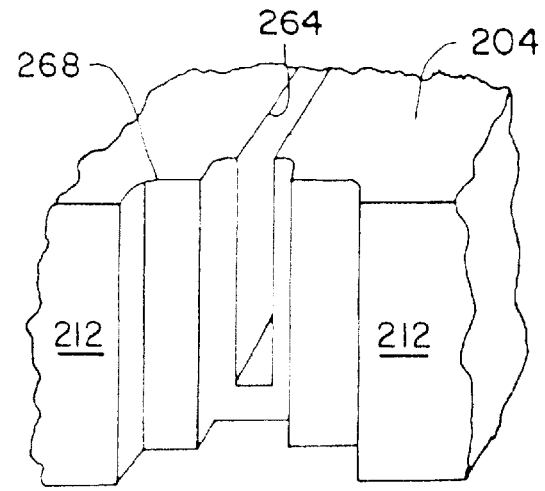
FIG. 14C is a cutaway, isometric view of the control port slot region of the channel housing of FIG. 8A.
Figure 14A:
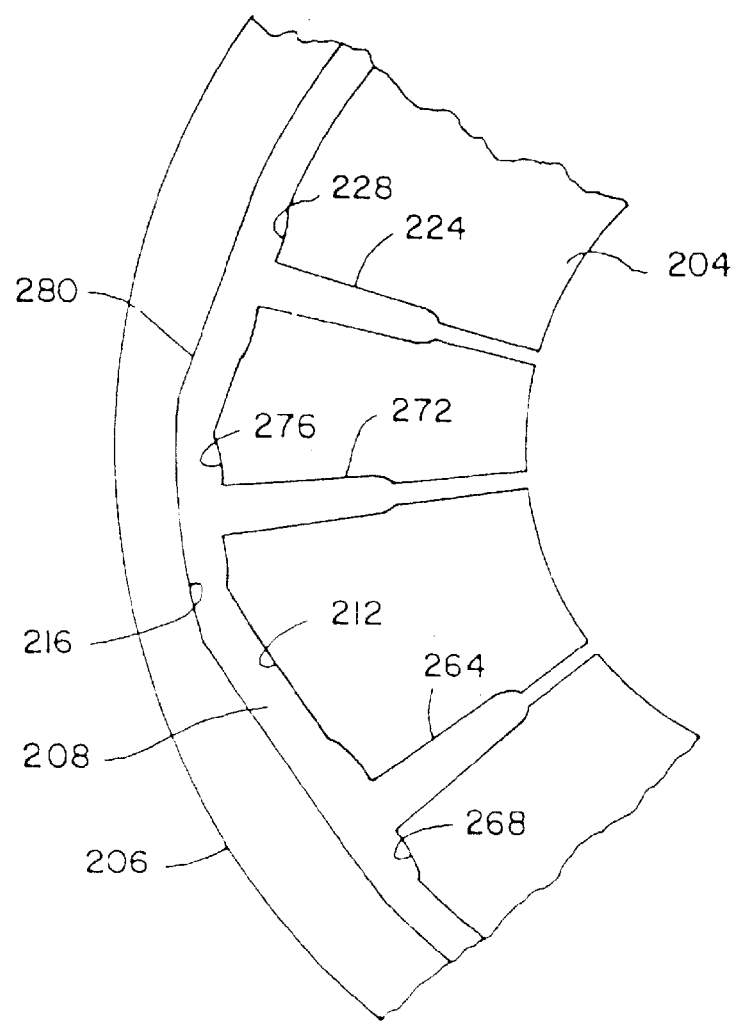
FIG. 14A is a top view of the blood inlet port slot, the RBC outlet slot, and the control port slot on the channel housing of FIG. 8A.
Figure 14B:
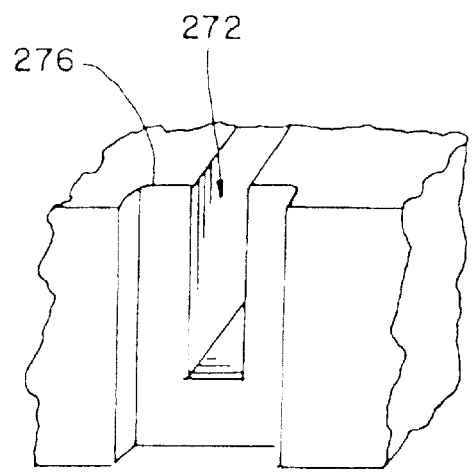
FIG. 14B is a cutaway, isometric view of the whole blood inlet port slot region of the channel housing of FIG. 8A.

In the illustrated embodiment and as best illustrated in FIG. 12, the noted "restriction" in the channel 208 is provided by configuring the outer channel wall 216 with a generally C-shaped profile. In this portion of the channel 208, the channel 208 includes an upper channel section 292 having a first width, a mid-channel section 300 having a second width greater than the first width, and a lower channel section 304 having a width less than that of the mid-channel section 300 and which is typically equal to that of the upper channel section 292. This profile is provided by an upper lip 296 which extends radially inwardly from the outer channel wall 216 toward, but displaced from, the inner channel wall 212, and by a lower lip 308 which extends radially inwardly from the outer channel wall 216 toward, but displaced from, the inner channel wall 212. This lower lip 308 actually defines a portion of the channel base 220 but does extend entirely from the outer channel wall 216 to the inner channel wall 212 such that it defines a notch 218.

When the blood processing vessel 352/352a is loaded into the channel 208, the fluid-containing volume of the coinciding portion of the blood processing vessel 352/352a is disposed below the upper channel section 292 and is principally contained within the mid-channel section 300. That is, the upper lip 296 "hangs over" the fluid-containing volume of the blood processing vessel 352/352a over at least a portion of its length. The upper lip 296 thereby functions to retain the blood processing vessel 352/352a within the channel 208 during rotation of the channel housing 204. Moreover, the upper lip 296 reduces the potential for creep by supporting the vessel 352/352a proximate the upper seal 380. The upper channel section 292 and the lower channel section 304 are multi-functional in that they also serve to receive and support an upper seal 380 and lower seal 384 of the blood processing vessel 352/352a to a degree such that the stresses induced on these portions of the blood processing vessel 352/352a during an apheresis procedure are reduced as will be discussed in more detail below. As can be appreciated, a similarly configured upper lip and lower lip could extend outwardly from the inner channel wall 212 toward, but displaced from, the outer channel wall 216, alone or in combination with the upper lip 296 and lower lip 308, and still retain this same general profile for the channel 208 to provide the noted functions.

Another desirable attribute of the channel 208 is that it allows for the use of blood as the liquid which primes the blood processing vessel 352/352a versus, for instance, saline solutions. Priming with blood allows for the actual collection of blood components to begin immediately (i.e., blood used in the prime is separated into blood component types, at least one of which may be collected). Blood priming is subject to a number of characterizations in relation to the apheresis system 2 and is based primarily upon the configuration of the channel F 208. or instance, the configuration of the channel 208 allows for blood to be the first liquid introduced into the blood processing vessel 352/352a which is loaded in the channel 208. Moreover, the configuration of the channel 208 allows separated plasma to flow in a clockwise direction through the channel 208 and to reach the control port slot 264 (FIG. 8a and thus the control port assembly 488 of the blood processing vessel 352) before any separated RBCs or any of the other noted large cells flow in the same clockwise direction beyond the RBC dam 232 and thus into the second stage 316 (i.e., a spillover condition). That is, blood priming may be utilized since control of the interface between the separated RBCs and the buffy coat is established before any RBCs or WBCs spill over into the second stage 316. Blood priming may also be characterized as providing blood and/or blood components to the entire volume of the blood processing vessel 352/352a prior to any RBCs or any of the other noted large cells flowing beyond the RBC dam 232 and into the second stage 316.

In order to achieve this desired objective of priming the blood processing vessel 352/352a with blood, generally the volume of the channel 208 which does not have RBCs to the volume of the channel 208 which does have RBCs must be less than one-half of one less than the ratio of the hematocrit of the RBCs leaving the channel 208 through the RBC outlet port assembly 516 to the hematocrit of the blood being introduced into the channel 208 through the blood inlet port assembly 388. This may be mathematically expressed as follows $V_2/V_1 < (H_{RP}/H_{IN} - 1)/2$, where:

$V_2$ = the volume of the channel 208 containing only plasma or platelet-rich plasma;

$V_1$ = the volume of the channel 208 containing RBCs of the first stage 312 and third stage 320;

$H_{RP}$=the hematocrit of the pocked RBCs leaving the channel 208 through the RBC outlet port assembly 516; and $H_{IN}$=the hematocrit of the blood entering the channel 208 through the blood inlet port assembly 388.

This equation assumes that the hematocrit in the RBC volume and is calculated as (HIN+HRP)/2. In the case where the HIN is equal to 0.47 and HRP is equal to 0.75, this requires that the ratio of V1/V2 be less than 0.30 in order for a blood prime to be possible.

The noted ratio may be further characterized as the ratio of that portion of the channel 208 which may be characterized as containing primarily plasma (e.g., VPL) to the volume of that portion of the channel 208 which may be characterized as containing primarily RBCs (e.g., VRBC). Referring to FIG. 15, these respective volumes may be defined by a reference circle 332 which originates at the rotational axis 324 and which intersects the RBC dam 232 at the illustrated location which would be at the border of a spillover condition. Portions of the channel 208 which are disposed outside of this reference circle 232 are defined as that portion of the channel 208 which includes primarily RBCs or which defines VRBC (e.g., about 77.85 cc in the illustrated embodiment), while those portions of the channel 208 which are disposed inside of the reference circle 232 are defined as that portion of the channel 208 which includes primarily plasma or which defines VPL (e.g., about 19.6 cc in the illustrated embodiment). In the illustrated embodiment, the ratio of VPL/VRBC is about 0.25 which is less than that noted above for the theoretical calculation for the blood prime (e.g., 0.30 based upon comparison of the hematocrits). In order to further achieve the noted desired ratio, the width and height of the channel 208 throughout that portion of the second stage 316 disposed in a clockwise direction from the platelet collect well 236 (FIG. 8a or the dam 232 (FIG. 8B), also in third stage 320, are each less than the width and height of the channel 208 throughout the entire first stage 312.

Another important feature relating to the configuration of the channel 208 is that the radially inwardmost portion of the inner channel wall 212 is at the interface with the plasma outlet slot 256. That is, the entirety of the inner channel wall 212 slopes toward the plasma outlet slot 256. This allows any air which is present in the blood processing vessel 352/352a during priming to be removed from the blood processing vessel 352/352a through the plasma outlet slot 256 and more specifically the plasma outlet port assembly 452 in the air will be the least dense fluid within the blood processing vessel 352/352a this time.

Another desirable attribute of the channel 208 is that it contributes to being able to utilize a high packing factor in an apheresis procedure. A "packing factor" is a dimensionless quantification of the degree of packing of the various blood component types in the first stage 312 and is thus reflective of the spacings between the various blood component types. The packing factor may thus be viewed similarly to a theoretical density of sorts (e.g., given a quantity of space, what is the maximum number of a particular blood component type that can be contained in this space).e The packing factor is more specifically defined by the following equation:

$$PF = \omega^2 \times R \times (v_{RBC}/W) \times V/Q_{IN}, \text{ where:}$$

PF=packing factor;
ω=rotational velocity;

R=the average radius of the outer channel wall 216 in the first cell separation stage 312;
$V_{RBC}$=the sedimentation velocity of RBCs at 1G;
V=the functional volume of the first cell separation stage 312;
W=the average sedimentation distance or width of the channel 208; and
$Q_{IN}$=the total inlet flow to the channel 208.

Consequently, the packing factor as used herein is dependent upon not only the configuration of the channel 208, particularly the first stage 312, but the rotational velocities being used in the apheresis procedure as well as the inlet flow to the blood processing vessel 352/352a. The following are packing factors associated with the blood processing channel 208 having the above-described dimensions:

| | N (rpm) | $Q_{in}$ ml/ml | V (ml) | PF | G @ $R_{avg}$ | P @ R1st (psi) |
|---|---|---|---|---|---|---|
| FF8 | 0 | 0 | 62.8 | 0.0 | 0.0 | 0.0 |
| SLOPE = .02 | 905 | 5 | 62.8 | 13.0 | 100.1 | 8.1 |
| | 1279 | 10 | 62.8 | 13.0 | 200.2 | 16.2 |
| | 1567 | 15 | 62.8 | 13.0 | 300.2 | 24.3 |
| | 1809 | 20 | 62.8 | 13.0 | 400.3 | 32.5 |
| | 2023 | 25 | 62.8 | 13.0 | 500.4 | 40.6 |
| | 2216 | 30 | 62.8 | 13.0 | 600.5 | 48.7 |
| | 2394 | 35 | 62.8 | 13.0 | 700.6 | 56.8 |
| | 2559 | 40 | 62.8 | 13.0 | 800.6 | 64.9 |
| | 2714 | 45 | 62.8 | 13.0 | 900.7 | 73.0 |
| | 2861 | 50 | 62.8 | 13.0 | 1100.9 | 81.1 |
| | 3001 | 55 | 62.8 | 13.0 | 1100.9 | 89.3 |
| | 3001 | 60 | 62.8 | 11.9 | 1100.9 | 89.3 |
| | 3001 | 65 | 62.8 | 11.0 | 1100.9 | 89.3 |
| | 3001 | 70 | 62.8 | 10.2 | 1100.9 | 89.3 |
| | 3001 | 75 | 62.8 | 9.5 | 1100.9 | 89.3 |
| | 3001 | 80 | 62.8 | 8.9 | 1100.9 | 89.3 |
| | 3001 | 85 | 62.8 | 8.4 | 1100.9 | 89.3 |
| | 3001 | 90 | 62.8 | 7.9 | 1100.9 | 89.3 |
| | 3001 | 95 | 62.8 | 7.5 | 1100.9 | 89.3 |
| | 3001 | 100 | 62.8 | 7.1 | 1100.9 | 89.3 |
| | 3001 | 105 | 62.8 | 6.8 | 1100.9 | 89.3 |
| | 3001 | 110 | 62.8 | 6.5 | 1100.9 | 89.3 |
| | 3001 | 115 | 62.8 | 6.2 | 1100.9 | 89.3 |
| | 3001 | 120 | 62.8 | 6.0 | 1100.9 | 89.3 |
| | 3001 | 125 | 62.8 | 5.7 | 1100.9 | 89.3 |
| | 3001 | 130 | 62.8 | 5.5 | 1100.9 | 89.3 |
| | 3001 | 135 | 62.8 | 5.3 | 1100.9 | 89.3 |
| | 3001 | 140 | 62.8 | 5.1 | 1100.9 | 89.3 |

Note the G forces are listed for the various rotational speeds at the middle of the first stage 312 and for a 10 inch outer diameter for the channel housing 204. At about G 2,560 RPM, force is about 800 G, while at about 3,000 RPM the G force is about 1,100 Gs.

Increasing the packing factor beyond a certain point produces diminishing returns regarding the collection of blood component types. That is, further increases in packing factor may not produce correspondingly increased collection efficiencies and may in fact impede the collection of blood component types. It is believed that a packing factor ranging from about 4 to about 21, preferably from about 11 to 16, and more preferably about 13, is optimum for collection of most blood component types. It has been observed, however, that during red blood cell collection, an increased packing factor (i.e., >13) may prove desirable to lower the level of white blood cells in the collected RBC product. A packing factor of 16 has been found preferable in collecting RBCs and plasma simultaneously with the embodiment of FIGS. 2C–2D and 8B (see below). The rotational velocity of the channel housing 204 may be adjusted based upon the inlet flows being provided to the blood processing vessel 352 or 352a to maintain the desired packing factor. For instance, the desired operating speed for the centrifuge housing 204 during the normal course of an apheresis procedure is preferably about 3,000 RPM. However, this rotational speed may be reduced to "match" the inlet flow to the blood processing vessel 352 or in order to retain the desired packing factor. Similarly, the rotational speed of the channel housing 204 may be increased to "match" an increased inlet flow to the blood processing vessel 352/352a in order to retain the desired packing factor.

Due to constraints regarding the blood processing vessel 352/352a, more specifically the various tubes interconnected therewith (e.g., which provide the seal-less loop), the above-noted desired packing factors of about 13 may be realized for inlet flows of up to about 55 ml/min. (instantaneous). Beyond 55 ml/min., the rotational speed would have to be increased above 3000 RPM to maintain the desired packing factor of about 13. Although tubes exist which will withstand those rotational speeds, presently they are not approved for use in an apheresis system. With the presently approved tubing, the packing factor may be maintained at a minimum of about 10, and preferably at least about 10.2, or even 11, for inlet flows (instantaneous) of about 40–70 ml/min. For the packing factor preference of 16 for the collection of RBCs and plasma together (FIGS. 2C–2D), a maximum 3000 RPM rotational speed would indicate that a slower inlet flow would be necessary. The higher packing factor of 16 provides a purer plasma separation (i.e., fewer platelets) over the RBC dam; and thus, a purer plasma product. However, a packing factor of 16 is also slower because of the lower inlet flow. Thus, after collecting plasma and RBCs together (until a minimum desired amount of plasma is collected, for instance), then the packing factor would preferably be reduced to about 13 to collect RBCs at a faster rate.

The packing factor may also be related to the resulting hematocrit achieved by the system. A target hematocrit of 80, for example, has been readily achievable with a packing factor of preferably between 11 and 16, and again preferably about 13. Note, the resulting hematocrit is also dependent on the amount of separated plasma which is re-mixed with the separated RBCs in the interface control outlets, as described herein.

At the above noted increased rotational speeds, the channel 208 not only provides for achieving an increased packing factor, but reduces the impact of this high packing factor on the collection efficiency regarding platelet collection. Specifically, the configuration of the channel 208 is selected to reduce the number of platelets that are retained within the first stage 312 (in FIG. 8A embodiment). The configuration of the channel 208 in the first stage 208 utilizes a progressively reduced width or sedimentation distance progressing from the blood inlet slot 224 to the RBC dam 232. That is, the width of the channel 208 proximate the blood inlet slot 224 is less than the width of the channel 208 proximate the RBC dam 232. This configuration of the channel 208 in the first stage 312 reduces the volume of the "buffy coat" or more specifically layer between the RBCs and platelets to be collected. As noted, this buffy coat includes primarily WBCs and lymphocytes, as well as the radially outwardmost portion of the platelet layer. The "buffy coat" is preferably retained in the first stage 312 during an apheresis procedure. Since the volume of the "buffy coat" is reduced by the reduced width of the channel 208 proximate the RBC dam 232, this reduces the number of platelets which are retained in the first stage(FIG. 8A), and thus increases the number of platelets which flow to the platelet collect well 236 (FIG. 8A).

Disposable Set: Blood Processing Vessel

The blood processing vessel 352 (or 352a in the FIG. 2C, 8B embodiment) is disposed within the channel 208 for directly interfacing with and receiving a flow of blood in an apheresis procedure. The use of the blood processing vessel 352/352a alleviates the need for sterilization of the channel housing 204 after each apheresis procedure and the vessel 352/352a may be discarded to provide a disposable system. There are initially two important characteristics regarding the overall structure of the blood processing vessel 352/352a. The blood processing vessel 352/352a is constructed such that it is sufficiently rigid to be free-standing in the channel 208. Moreover, the blood processing vessel 352/352a is also sufficiently rigid so as to be loaded in the channel 208 having the aboveidentified configuration (i.e., such that the blood processing vessel 352/352a must be directed through the reduced width upper channel section 292 before passage into the larger width mid-channel section 300). However, the blood processing vessel 352/352a must also be sufficiently flexible so as to substantially conform to the shape of the channel 208 during an apheresis procedure.

In order to achieve the above-noted characteristics, the blood processing vessel 352/352a may be constructed as follows. Initially, materials for the blood processing vessel 352/352a include PVC, PETG, and polyolefins, with PVC being preferred. Moreover, the wall of thickness of the blood processing vessel 352/352a will typically range between about 0.030" and 0.040". Furthermore, the durometer rating of the body of the blood processing vessel 352/352a will generally range from about 50 Shore A to about 90 Shore A.

Referring primarily to FIGS. 16–23B, the blood processing vessel 352/352a includes a first end 356 and a second end 364 which overlaps with the first end 356 and is radially spaced therefrom. A first connector 360 is disposed proximate the first end 356 and a second connector 368 is disposed proximate the second end 364. When the first connector 360 and second connector 368 are engaged (typically permanently), a continuous flow path is available through the blood processing vessel 352/352a. This construction of the blood processing vessel 352/352a facilitates loading in the channel 208 in the proper position and as noted also contributes to the automatic control of the interface between the separated RBCs and the buffy coat or plasma relative to the RBC dam 232.

The blood processing vessel 352/352a includes an inner sidewall 372 and an outer sidewall 376. In the illustrated embodiment, the blood processing vessel 352/352a is formed by sealing two pieces of material together (e.g., RF welding). More specifically, the inner sidewall 372 and outer sidewall 376 are connected along the entire length of the blood processing vessel 352/352a to define an upper seal 380 and a lower seal 384. Seals are also provided on the ends of the vessel 352/352a. The upper seal 380 is disposed in the reduced width upper channel section 292 of the channel 208, while the lower seal 384 is disposed in the reduced width lower channel section 304 of the channel 208 (e.g., FIG. This 19F). again reduces the stresses on the upper seal 380 and lower seal 384 when a flow of blood is provided to the blood processing vessel 352/352a and pressurizes the same. That is, the upper seal 380 and lower seal 384 are effectively supported by the channel 208 during an apheresis procedure such that a resistance is provided to a "pulling apart" of the upper seal 380 and lower seal 384. By utilizing two separate sheets to form the blood processing vessel 352/352a, a "flatter" profile may also be achieved. This type of profile is beneficial during rinseback, and also facilitates loading and unloading of the vessel 352/352a relative to the channel 208.

Blood is introduced into the interior of the blood processing vessel 352/352a through a blood inlet port assembly 388 which is more particularly illustrated in FIGS. 19a–g.

Initially, the port 392, as all other ports, is welded to the blood processing vessel 352/352a over a relatively small area. This results in less movement of materials due to the welding procedure which provides a smoother surface for engagement by the blood and/or blood component types.

The blood inlet port assembly 388 includes a blood inlet port 392 and a blood inlet tube 412 which is fluidly interconnected therewith exteriorly of the blood processing vessel 352/352a. The blood inlet port 392 extends through and beyond the inner sidewall 372 of the blood processing vessel 352/352a into an interior portion of the blood processing vessel 352/352a. Generally, the blood inlet port assembly 388 is structured to allow blood to be introduced into the blood processing vessel 352/352a during an apheresis procedure without substantially adversely affecting the operation of the apheresis system 2.

Figure 19A:
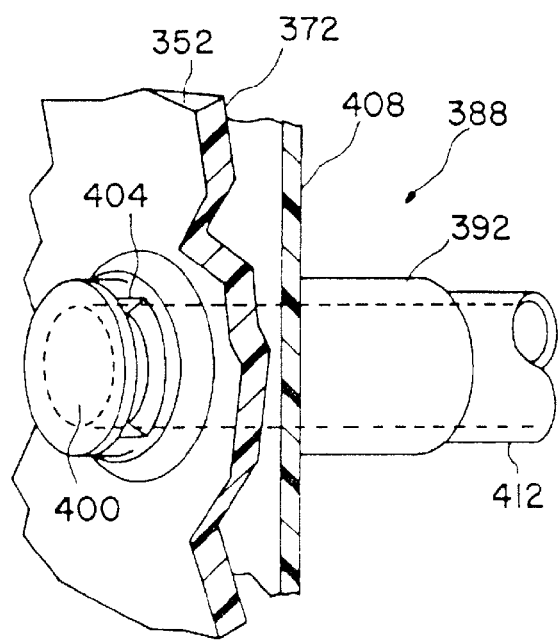
FIG. 19A is a cutaway, isometric view of the blood inlet port assembly for the blood processing vessel of FIG. 8A.
Figure 19B:
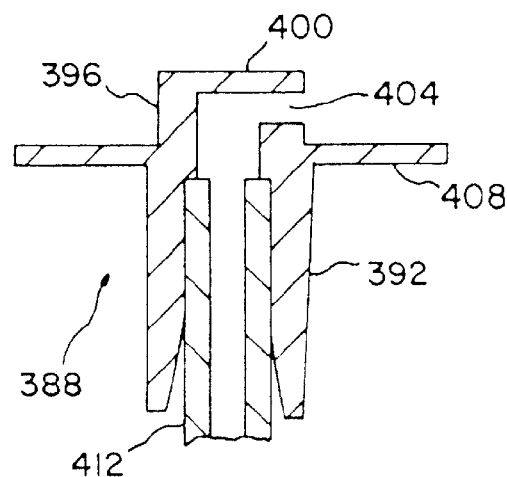
FIG. 19B is a longitudinal cross-sectional view of the blood inlet port assembly for the blood processing vessel of FIG. 8A.
Figure 19C:
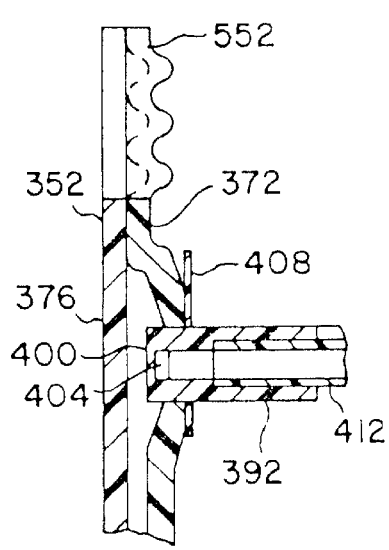
FIG. 19C is a cross-sectional view of the blood inlet port assembly interfacing with the blood processing vessel of FIG. 8A.
Figure 19D:
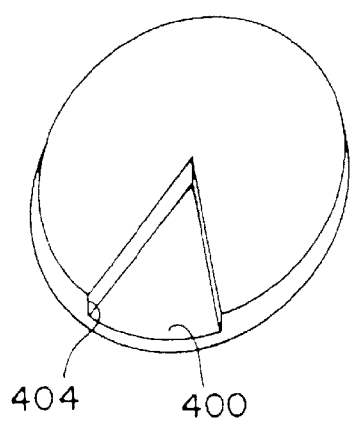
FIG. 19D is an isometric view of the interior of the vane of the blood inlet port of FIG.
Figure 20A:
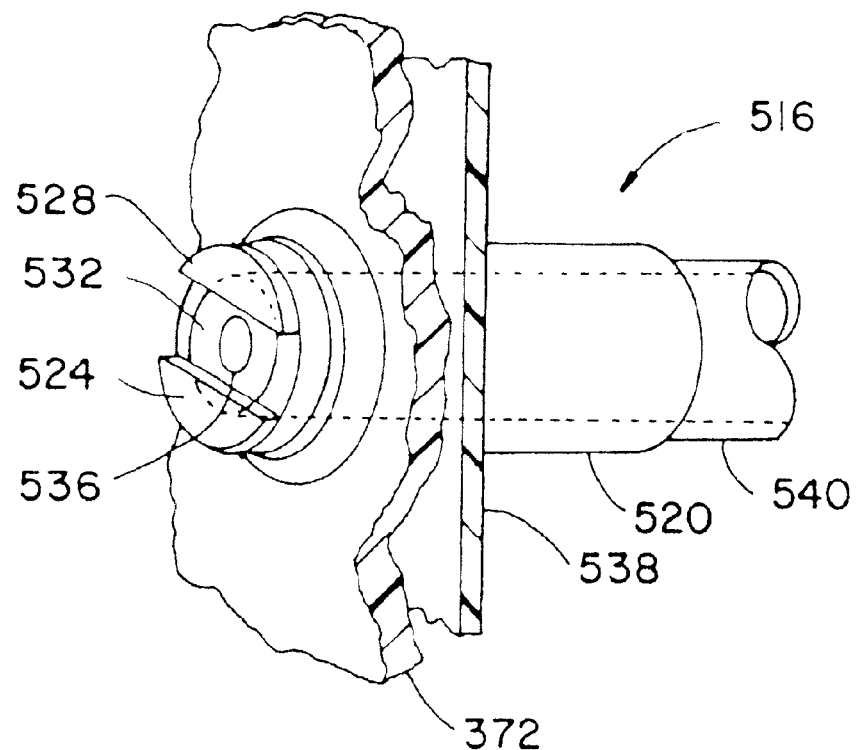
FIG. 20A is a cutaway, isometric view of the red blood cell outlet port assembly interfacing with the blood processing vessel of FIG. 8A.
Figure 20B:
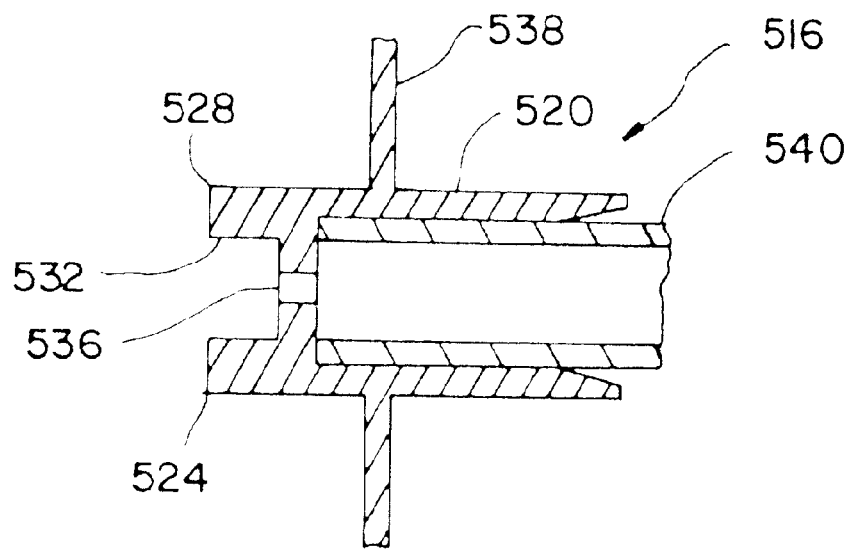
FIG. 20B is a longitudinal, cross-sectional view of the red blood cell outlet port assembly of FIG. 20A.
Figure 20C:
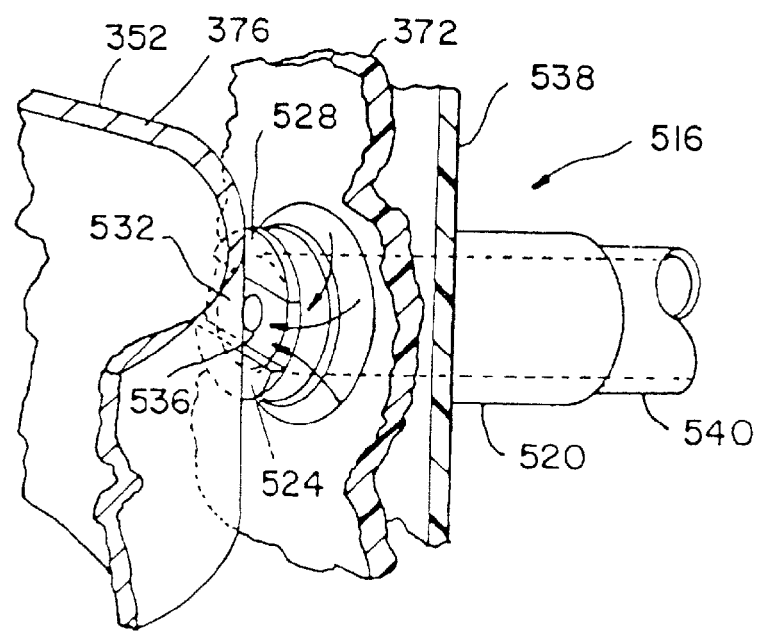
FIG. 20C is a cutaway, isometric view of the red blood cell port assembly interfacing with the blood processing vessel of FIG. 8A during rinseback at the end of an apheresis procedure.
Figure 20D:
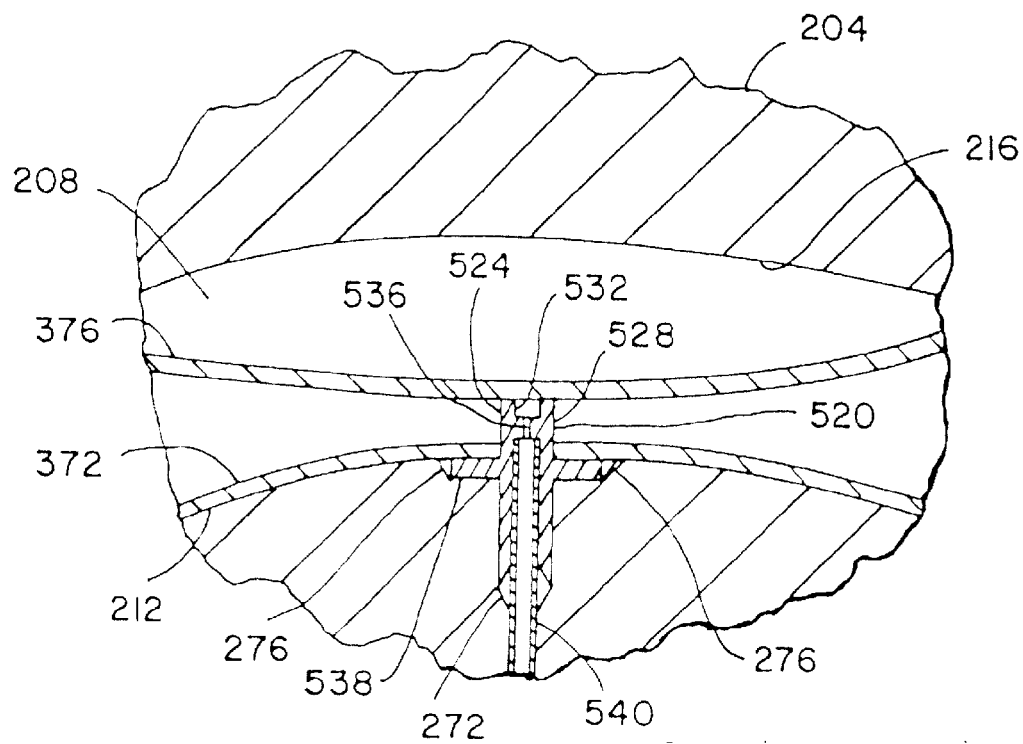
FIG. 20D is a cross-sectional view, looking downwardly, of the red blood cell outlet port assembly interfacing with the blood processing vessel in the channel of FIG. 8A during rinseback at the end of an apheresis procedure.
Figure 21A:
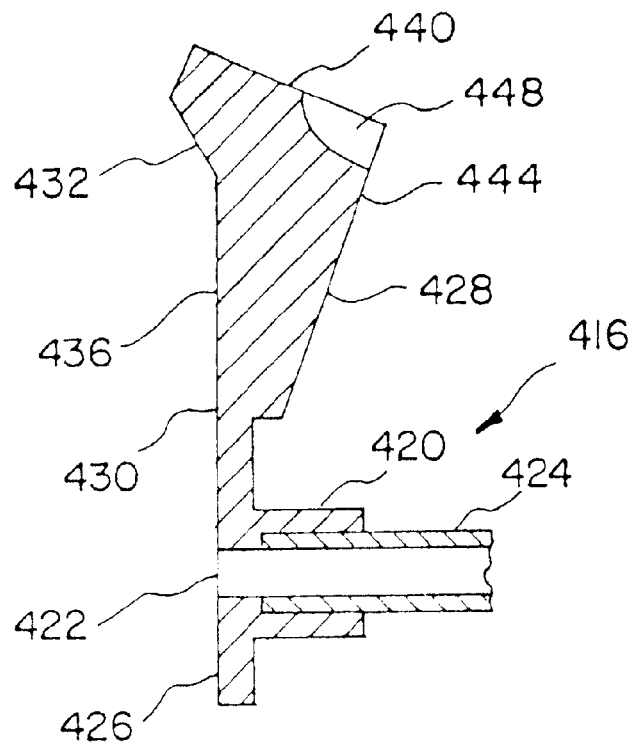
FIG. 21A is a cross-sectional view of the platelet outlet port assembly for the blood processing vessel of FIG. 8A.
Figure 21B:
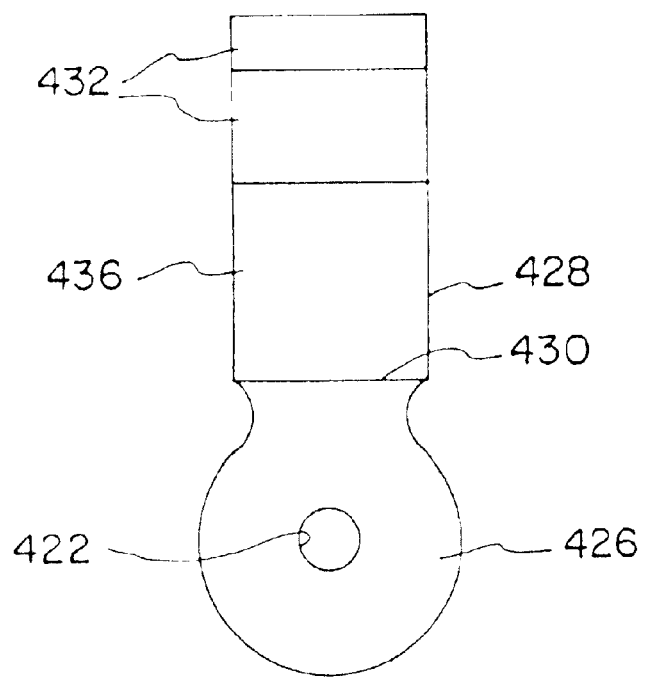
FIG. 21B is a plan view of the platelet outlet port assembly of FIG. 21A from the interior of the channel.

The blood inlet port 392 includes a substantially cylindrical sidewall 396. A generally vertically extending slot 404 is disposed proximate an end of the sidewall 396 of the blood inlet port 392 such that the slot 404 is substantially parallel with the inner sidewall 372 and outer sidewall 376 of the blood processing vessel 352/352a. The slot 404 projects in the clockwise direction, and thus directs the flow of blood in the channel 208 generally toward the RBC dam 232. A vane 400 is positioned on the end of the cylindrical sidewall 396, is disposed to be substantially parallel with the inner sidewall 322 and thereby directs the flow of blood out through the slot 404. As illustrated in FIG. 19D, the vane 400 includes a generally V-shaped notch on the interior of the blood inlet port 392, the arcuate extent of which defines the "height" of the slot 404.

The desired manner of flow of blood into the blood processing vessel 352/352a during an apheresis procedure is subject to a number of characterizations, each of which is provided by the above-described blood inlet port assembly 388. Initially, the flow of blood into the blood processing vessel may be characterized as being at an angle of less than 90 degrees relative a reference line which is perpendicular to the inner sidewall 372 of the blood processing vessel 352/352a. That is, the blood is injected in a direction which is at least partially in the direction of the desired flow of blood through the blood processing vessel 352/352a. Moreover, the desired flow of blood into the blood processing vessel 352/352a may be characterized as that which reduces the effect on other flow characteristics within blood processing vessel 352/352a at the blood inlet port 392.

Separated RBCs 556 again flow along the outer sidewall 376 of the blood processing vessel 352/352a adjacent the outer channel wall 216, past the blood inlet port 392 and the RBC outlet port assembly 516 as illustrated in FIGS. 19E and 19G. The desired flow of blood into the blood processing vessel 352/352a may then be further characterized as that which is substantially parallel with at least one other flow in the region of the blood inlet port 392 (e.g., inject the blood substantially parallel with the flow of RBCs 556). This manner of introducing blood into the blood processing vessel 352/352a may then be further characterized as that which does not significantly impact at least one other flow in the region of the blood inlet port 392.

As noted above, the blood inlet port assembly 388 interfaces with the inner sidewall 372 of the blood processing vessel 352/352a in a manner which minimizes the discontinuity along the inner channel wall 212 in the region of the blood inlet slot 224 in which the blood inlet port 392 is disposed. Specifically, a shield 408 may be integrally formed with and disposed about the blood inlet port 392. The shield 408 is disposed on an exterior surface of the blood processing vessel 352/352a and interfaces with its inner sidewall 372. The shield 408 is at least in partial overlapping relation with the inner sidewall 372. Moreover, in the case where the shield 408 is integrally formed with the port 392, it need not be attached to the inner sidewall 372. The port 392 is installed asymmetrical relative to the shield 408 which is beneficial for manufacturability. All shields and their blood-related ports discussed below also include this feature.

Generally, the shield 408 is more rigid than the inner sidewall 372 of the blood processing vessel 352/352a. This increased rigidity may be provided by utilizing a more rigid material for the shield 408 than is used for the inner sidewall 372. For instance, the durometer rating of the material forming the shield 408 may range from about 90 Shore A to about 130 Shore A, while the durometer rating of the material forming the inner sidewall 372 of the blood processing vessel 352/352a again ranges from about 50 Shore A to about 90 Shore A in one embodiment. This durometer rating (when the shield 408 and port 392 are integrally formed) also enhances the seal between the port 392 and the tube installed therein.

When the blood inlet port 392 is disposed in the blood inlet slot 224 when loading the blood processing vessel 352/352a in the channel 208, the shield 408 is positioned within the recess 228 formed in the inner channel wall 212. Again, the blood inlet slot 224 intersects with the inner channel wall 212, and more specifically the recess 228. That is, the recess 228 contains and is disposed about one end of the blood inlet slot 224. Preferably, the thickness of the shield 408 is substantially equal to the depth or thickness of the recess 228 such that the amount of discontinuity along the inner channel wall 212 in the region of the blood inlet slot 224 is reduced or minimized. Due to the increased rigidity of the shield 408 in comparison to the materials forming the blood processing vessel 352/352a, when the blood processing vessel 352/352a is pressurized during an apheresis procedure the shield 408 restricts movement of the blood processing vessel 352/352a and/or the blood inlet port 392 into the blood inlet slot 224. That is, the shield 408 restricts and preferably minimizes any deflection of the blood processing vessel 352/352a into the blood inlet slot 224 during the procedure. Moreover, with the shield 408 being integrally formed with the blood inlet port 392, the radial position of the vertical slot 404 in the blood inlet port 392 is not dependent upon the thickness of the materials forming the blood processing vessel 352/352a.

In the first stage 312, blood which is provided to the blood processing vessel 352/352a by the blood inlet port assembly 388 is separated into at least RBCs, and plasma. The RBCs, as well as most of the WBCs, are retained within the first stage 312 and are preferably precluded from flowing in a clockwise direction past the RBC dam 232 into the second stage 316 or, in the FIG. 8A embodiment, into the platelet collect well Instead, the RBCs and WBCs are induced to flow along the outer channel wall 216 in a counterclockwise direction past the blood inlet port 392 and toward the RBC outlet port assembly 516 of the blood processing vessel 352/352a. That is, the RBC outlet port assembly 516 is disposed in a counterclockwise direction from the blood inlet port assembly 388. However, as noted above, in the FIG. 8A embodiment, the control port dam 280 impedes the flow to the buffy coat control port assembly 488 to provide a sharp interface between the separated RBCs and the plasma proximate the control port assembly 488 such that this may be used to control the radial position of the interface between the RBCs and the buffy coat in the area of the RBC dam 232. In the FIG. 8B embodiment on the other hand, the interface is established proximate the RBC/control port 520 as described hereinbelow.

The RBC outlet port assembly 516 is more specifically illustrated in FIGS. 20A–D and generally includes an RBC outlet port 520 and an RBC outlet tube 540 fluidly interconnected therewith exteriorly of the blood processing vessel 352/352a. The RBC outlet port 520 extends through and beyond the inner sidewall 372 of the blood processing vessel 352/352a into an interior portion of the blood processing vessel 352/352a. In addition to removing separated RBCs from the blood processing vessel 352/352a during an apheresis procedure, the RBC outlet port assembly 516 also functions in combination with the control port assembly 488 (FIG. 8A) or by itself (FIG. 8B) to automatically control the radial position of the interface between separated RBCs and the buffy coat or plasma relative to the RBC dam 232 (i.e., to prevent RBCs from flowing beyond the RBC dam 232) in a manner discussed in more detail below.

The RBC outlet port 520 is also configured to reduce the potential for the flow therethrough being obstructed during rinseback (i.e, during the evacuation of the blood processing vessel 352/352a upon completion of blood component separation and collection process so as to provide as much of the contents thereof back to the donor/patient 4). During rinseback, the rotation of the channel housing 204 is terminated and a relatively significant drawing action (e.g., by pumping) is utilized to attempt to remove all contents from the blood processing vessel 352/352a. The end of the RBC outlet port 520 includes a first protrusion 524 and a second protrusion 528 displaced therefrom, with a central recess 532 being disposed therebetween which contains the noted orifice 536 for the blood outlet port 520. The first protrusion 524 and the second protrusion 528 each extend further beyond the inner sidewall 372 of the blood processing vessel 352/352a a greater distance then the central recess 532/352a. As such, during rinseback if the outer sidewall 376 attempts to contact the inner sidewall 372, the first protrusion 524 and second protrusion 528 will displace the central recess 532 and its orifice 536 away from the outer sidewall 376. This retains the orifice 536 in an open condition such that the flow therethrough is not obstructed during rinseback.

As noted above, the RBC outlet port assembly 516 interfaces with the inner sidewall 372 of the blood processing vessel 352/352a in a manner which minimizes the discontinuity along the inner channel wall 212 in the region of the RBC outlet 272 in which the RBC outlet port 520 is disposed. Specifically, a shield 538 is integrally formed with and disposed about the RBC outlet port 520. The shield 538 is disposed on an exterior surface of the blood processing vessel 352/352a and interfaces with its inner sidewall 372. The shield 538 is at least in partial overlapping relation with the inner sidewall 372. Moreover, in the case where the shield 538 is integrally formed with the port 520, it need not be attached to the inner sidewall 372. Generally, the shield 538 is more rigid than the inner sidewall 372. This increased rigidity may be provided by utilizing a more rigid material for the shield 538 than is used for the inner sidewall 372. For instance, the durometer rating of the material forming the shield 538 may range from about 90 Shore A to about 130 Shore A, while the durometer rating of the material forming the inner sidewall 372 of the blood processing vessel 352/352a again ranges from about 50 Shore A to about 90 Shore A in one preferred embodiment.

When the RBC outlet port 520 is disposed in the RBC outlet slot 272 when loading the blood processing vessel 352/352a in the channel 208, the shield 538 is positioned within the recess 276 formed in the inner channel wall 212. Again, the RBC outlet slot 272 intersects with the inner channel wall 212, and more specifically the recess That is, the recess 276 contains and is disposed about one end of the RBC outlet slot 272. Preferably, the thickness of the shield 538 is substantially equal to the depth or thickness of the recess 276 such that the amount of discontinuity along the inner channel wall 212 in the region of the RBC outlet slot 272 is reduced or minimized. Due to the increased rigidity of the shield 538 in comparison to the materials forming the blood processing vessel 352/352a, when the blood processing vessel 352/352a is pressurized during an apheresis procedure, the shield 538 restricts movement of the blood processing vessel 352/352a and/or the RBC outlet port 520 into the RBC outlet slot 272. That is, the shield 538 restricts and preferably minimizes any deflection of the blood processing vessel 352/352a into the RBC outlet slot 272. Moreover, with the shield 538 being integrally formed with the RBC outlet port 520, the radial position of the orificeis not dependent upon the thickness of the materials forming the blood processing vessel 352/352a.

Separated platelets in the embodiment of FIG. 8A, are allowed to flow beyond the RBC dam 232 and into the second stage 316 of the channel 208 in platelet-rich plasma. The blood processing vessel 352 (FIG. 8A) includes a platelet collect port assembly 416 to continually remove these platelets from the vessel 352 throughout an apheresis procedure and such is more particularly illustrated in FIGS. 8A, 16, and 21A–B. Generally, the platelet collect port assembly 416 is disposed in a clockwise direction from the blood inlet port assembly 388, as well as from the RBC dam 232 when the blood processing vessel 352 is loaded into the channel 208. Moreover, the platelet collect port assembly 416 interfaces with the outer sidewall 376 of the blood processing vessel 352.

The platelet collect port assembly 416 (FIG. 8A) is disposed in the platelet support recess 249 and the platelet outlet tube recess 254 which are disposed radially outwardly from the portion of the platelet collect well 236 defined by the outer channel wall 216 of the channel 208. The platelet collect port assembly 416 generally includes a platelet collect port 420 and a platelet collect tube 424 which is fluidly interconnected therewith exteriorly of the blood processing vessel 352. The orifice 422 of the port 420 may be substantially flush with the interior surface of the outer sidewall 376 of the blood processing vessel 352. Moreover, the radial position of the orifice 422 is established by engagement of part of the platelet collect port 420 with boundaries of the recess 249 and/or 254.

The platelet collect port 420 (FIG. 8A) is welded to the blood processing vessel 352. The thickness of the overlapping portions of the port 420 and vessel 352 are substantially equal. The weld area is overheated such that there is a mixing of the two materials. This results in the platelet collect port 420 being able to flex substantially against the outer channel wall 216 when the vessel 352 is pressurized.

The blood processing vessel 352 (FIG. 8A) and the outer channel wall 216 of the channel 210 collectively define the platelet collect well 236. The contribution of the blood processing vessel 352 to the platelet collect well 236 is provided by a substantially rigid support 428 which is disposed vertically above the platelet collect port 420 and hingedly interconnected at location 430 with the outer sidewall 376 and/or a mounting plate 426 of the platelet collect port 420. The contoured support 428 includes a first face 432 and a second face 436 which interface with the exterior surface of the outer sidewall 376 of the blood processing vessel 352 (i.e., the support overlaps with the sidewall 376 of the blood processing vessel 352 and need not be attached thereto over the entire interface therewith) and which are disposed in different angular positions. The upper portion of the first face 432 extends over the top of the blood processing vessel 352, while the lower portion of the first face 432 generally coincides with the upper seal 380 on the blood processing vessel 352. The second face 436 interfaces with the outer sidewall 376 in a region of the fluid-containing volume of the blood processing vessel 352 and is the primary surface which directs platelets toward the platelet collect port 420.

When the blood processing vessel 352 (FIG. 8A) is pressurized, the support 428 moves into a predetermined position defined by portions of the platelet collect recess 252. Specifically, a third face 440 is retained under an upper lip 254 on the upper perimeter of the platelet support recess 249, and the two sides of a fourth face 444 seat against a shoulder 252 disposed on each side of the platelet support recess 249. A platelet tubing notch 448 is formed in the support 428 at generally the intersection between the third face 440 and the fourth face 444. The platelet collect tube 426 thus may extend out from the platelet collect port 420, up the platelet collect tube recess 254, against the platelet tube notch 448 if necessary, and above the channel housing 204 to pass down through the central opening 328 therein.

In order to increase the purity of platelets that are collected, a platelet purification system as described in U.S. patent application Ser. Nos. 08/423,578 and corresponding U.S. Pat. Nos. 5,674,173; 5,906,570; inter alia, and 08/423, 583 may be disposed in the platelet collect tube 424 of the embodiment of FIGS. 2A–2B and 8A, and the entire disclosures of these patent documents are incorporated by reference in their entirety herein.

Figure 22:
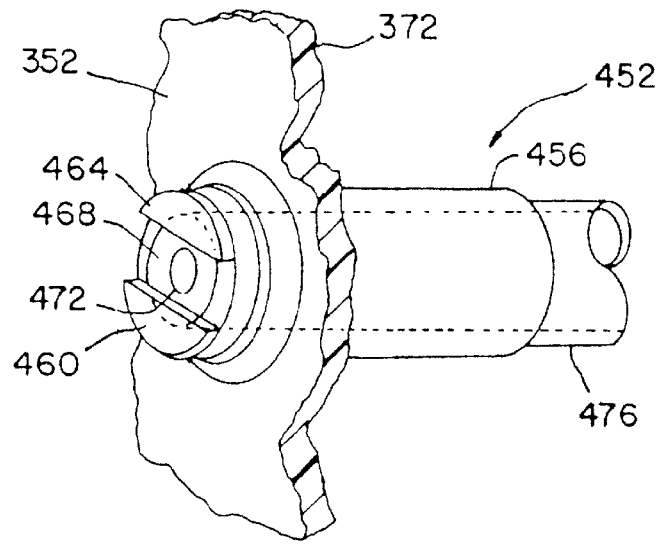
FIG. 22 is a cutaway, isometric view of the plasma port assembly for the blood processing vessel of FIG. 8A.

Platelet-poor plasma flows beyond the platelet collect well 236 (FIG. 8A) and/or beyond the dam 232 (FIG. 8B) and to the plasma outlet port assembly 452. Here, some of the platelet-poor plasma may be removed from the blood processing vessel 352/352a and collected, although this "separated" plasma may also be returned the donor/patient 4 in some instances. The plasma port 456 is also used in the blood priming of the vessel 352/352a in that air is removed from the vessel 352/352a through the plasma port 456. Referring to FIG. 22, the plasma outlet port assembly 452 includes a plasma outlet port 456 and a plasma outlet tube 476 which is fluidly interconnected therewith exteriorly of the blood processing vessel 352/352a. The plasma outlet port 456 extends through and beyond the inner sidewall 372 of the blood processing vessel 352/352a into an interior of the blood processing vessel 352/352a. The plasma outlet port 456 is disposed between the second end 364 of the blood processing vessel 352/352a and the second connector 368.

The plasma outlet port 456 is configured to reduce the potential for the flow therethrough being obstructed during rinseback (i.e., during evacuation of the blood processing vessel 352/352a upon completion of an apheresis procedure so as to provide as much of the contents thereof back to the donor/patient 4). During rinseback, the rotation of the channel housing 204 is terminated and a relatively significant drawing action (e.g., by pumping) is utilized to attempt to remove all contents from the blood processing vessel The end of the plasma outlet port 456 includes a first protrusion 460 and a second protrusion 464 displaced therefrom, with a central recess 468 being disposed therebetween which contains an orifice 472 for the plasma outlet port 456. The first protrusion 460 and the second protrusion 464 each extend further beyond the inner sidewall 372 of the blood processing vessel 352/352a a greater distance then the central recess 468. As such, during rinseback if the outer sidewall 376 attempts to contact the inner sidewall 372, the first protrusion 460 and second protrusion 464 will displace the central recess 468 and its orifice 472 away from the outer sidewall 376. This retains the orifice 472 in an open condition such that the flow therethrough is not obstructed during rinseback.

In order to further assist in withdrawal from the blood processing vessel 352/352a after completion of an apheresis procedure and thus during rinseback, a first passage 480 and a second passageway 484 (see FIGS. 8A, 8B and 16) are formed in the blood processing vessel 352/352a (e.g., via heat seals, RF seals) and generally extend downwardly from the plasma outlet port 456 toward a lower portion of the blood processing vessel 352/352a. The first passageway 480 and second passageway 484 are disposed on opposite sides of the plasma outlet port 456. With this configuration, a drawing action through the plasma outlet port 456 is initiated in a lower portion of the blood processing vessel 352/352a at two displaced locations.

Figure 23A:
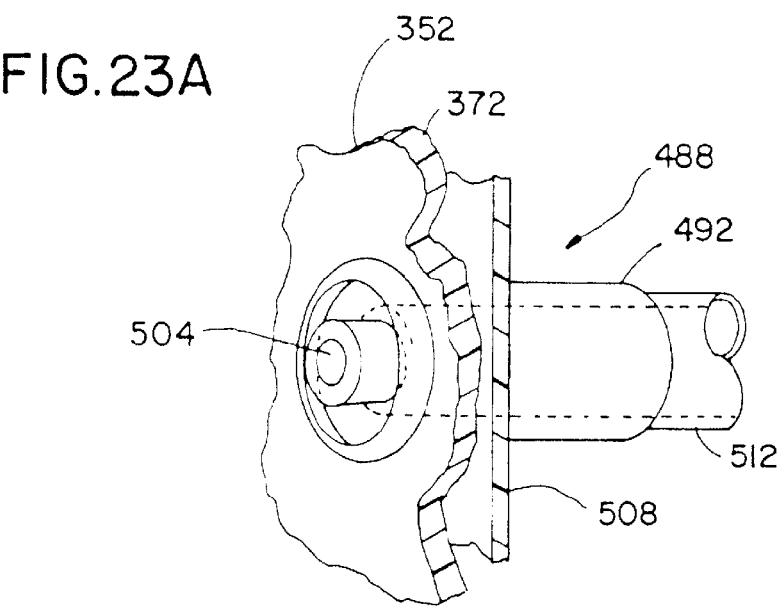
FIG. 23A is a cutaway, isometric view of the control port assembly for the blood processing vessel of FIG. 8A.
Figure 23B:
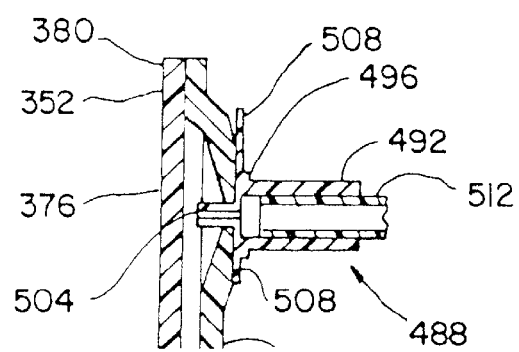
FIG. 23B is a cross-sectional view of the control port assembly interfacing with the blood processing vessel of FIG. 8A.
Figure 24:
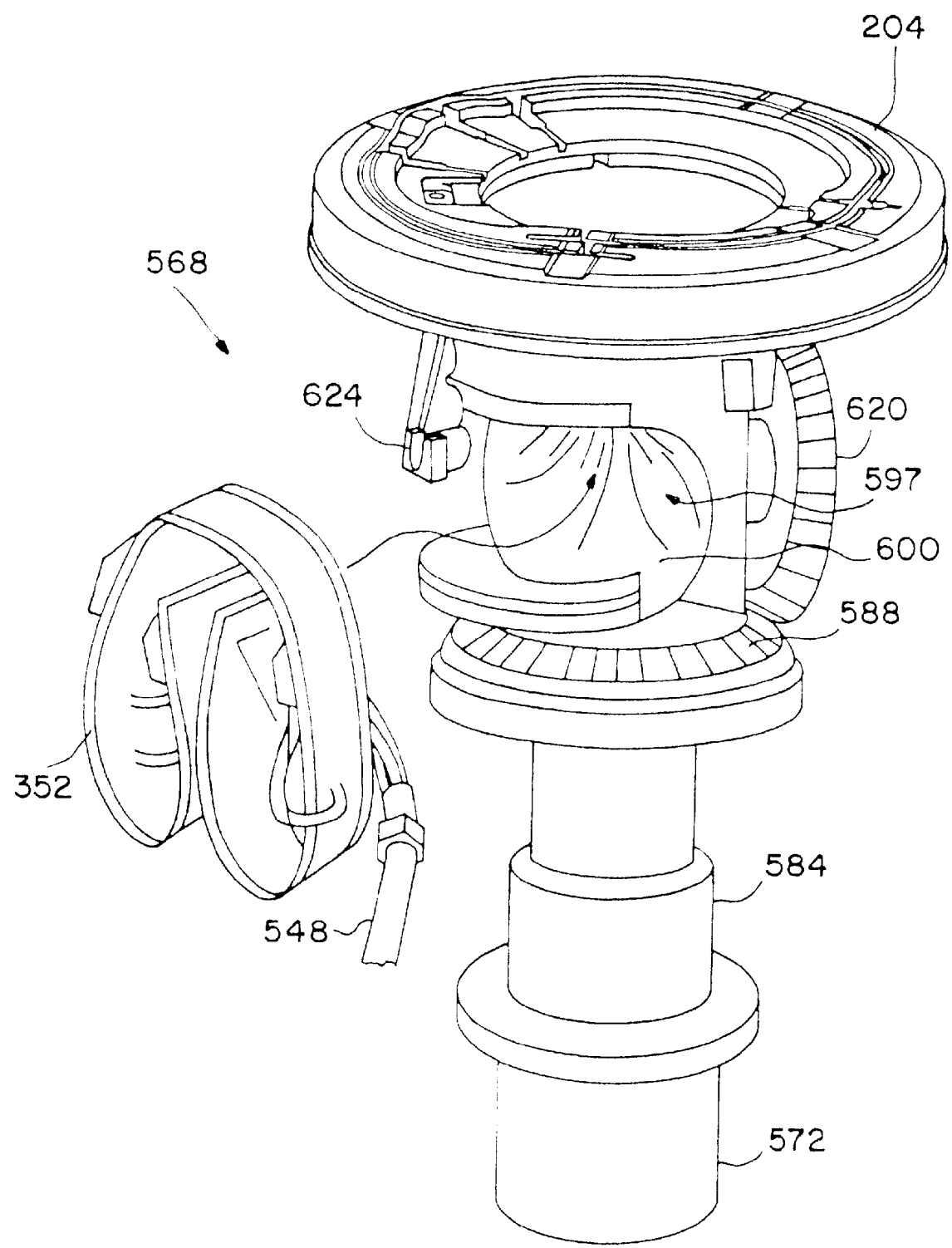
FIG. 24 is an isometric view of a centrifuge rotor assembly for the system of FIG. 1.

Some of the separated plasma is also utilized to automatically control the location of the interface between separated RBCs and the buffy coat or plasma in the first stage 312, specifically the radial position of this interface relative to the RBC dam 232. Plasma which provides this interface control function is removed from the blood processing vessel 352 by a control port assembly 488 in the embodiment of FIGS. 2A–2B and 8A, and which is illustrated in FIGS. 23A–B. (Again, the embodiment of FIGS. 2C–2D and 8B does not preferably have a control port assembly 488.) The control port assembly 488 is disposed in a clockwise direction from the plasma outlet port assembly 452 and proximate the RBC outlet port assembly 516, and thus between the first end 284 of the channel 208 and the RBC outlet port assembly 516. This plasma thus flows from the second stage 316 and into the third stage 320 to provide this function.

The control port assembly 488 (FIG. 8A) generally includes a control port 492 and control port tube 512 which is fluidly interconnected therewith exteriorly of the blood processing vessel 352. The control port 492 extends through and beyond the inner sidewall 372 of the blood processing vessel 352 into an interior portion of the blood processing vessel 352. The radial positioning of the orifice 504 of the control port 492 is not dependent upon the thickness of the material forming the blood processing vessel Instead, the control port 492 includes a shoulder 496 which engages or seats upon structure within the control port slot 264 to accurately place the orifice 504 at a predetermined radial position within the channel 208. Moreover, this predetermined radial position is substantially maintained even after the blood processing vessel is pressurized. In this regard, the control port assembly 488 interfaces with the inner sidewall 372 of the blood processing vessel 352 in a manner which minimizes the discontinuity along the inner channel wall 212 in the region of the control port slot 264 in which the control port 492 is disposed. Specifically, a shield 508 is integrally formed with and disposed about the control port 492. The shield 508 is disposed on an exterior surface of the blood processing vessel 352 and interfaces with its inner sidewall 372. The shield 508 is at least in partial overlapping relation with the inner sidewall 372. Moreover, in the case where the shield 508 is integrally formed with the port 492, it need not be attached to the inner sidewall 372. Generally, the shield 508 is more rigid than the inner sidewall 372 and this assists in maintaining the orifice 504 of the control port 492 at the desired radial position within the channel 208. This increased rigidity may be provided by utilizing a more rigid material for the shield 508 than is used for the inner sidewall 372. For instance, the durometer rating of the material forming the shield 508 may range from about 90 Shore A to about 130 Shore A, while the durometer rating of the material forming the inner sidewall 372 of the blood processing vessel 352 again ranges from about 50 Shore A to about 90 Shore A in one embodiment.

The control port assembly 488 (FIG. 8A) and/or the RBC outlet port assembly 516 (by itself in the FIG. 8B embodiment) function in combination to control the radial position of the interface between separated RBCs and the buffy coat or plasma relative to the RBC dam 232. In the FIG. 8A embodiment, two structural differences between the RBC outlet port assembly 516 and the control port assembly 488 contribute to achieving this automatic control. Initially, the orifice 536 to the RBC outlet port 520 is disposed further into the interior of the blood processing vessel 352 than the control port 492. In one embodiment, the orifice 536 of the RBC outlet port 520 is disposed more radially outwardly than the orifice 504 of the control port 492. Moreover, the diameter of the RBC outlet tube 540 is greater than that of the control port tube 512. In one embodiment, the inner diameter of the RBC outlet tube 54 is about 0.094", while the inner diameter of the control port tube 512 is about 0.035". The control port tube 512 and RBC outlet tube 540 also join into a common return tube 546 via a three-way tubing jack 544 which further assists in providing the automatic interface control feature.

The automatic interface position control is provided as follows utilizing the RBC outlet port assembly 516 and the control port assembly 488 in FIG. 8A. Initially, there are two interfaces in the channel 208 of significance with regard to this automatic interface position control feature. One of these interfaces is the RBC/buffy coat interface in relation to the RBC dam 232. However, there is also an RBC/plasma interface in the region of the control port assembly 488 which again is available through use of the control port dam 280. The control port dam 280 allows substantially only RBCs to flow to the control port assembly 488 in a counterclockwise direction.

In the event that the interface between the RBCs and plasma moves radially inwardly toward the rotational axis 324, RBCs will begin flowing out the control port tube 512 in addition to the RBC outlet tube 540. This decreases the flow through the smaller diameter control port tube 512 due to the higher viscosity and density of the RBCs compared to the plasma which typically flows through the control port tube 512. Consequently, the flow through the larger diameter RBC outlet tube 540 must increase since the flow through the return tube 546 must remain the same. This removes more RBCs from the first stage 312 such that both the interface between the RBCs and the buffy coat in relation to the RBC dam 232 and the interface between the RBCs and the plasma both move radially outwardly. That is, this changes the radial position of each of these interfaces. As such, the potential for RBCs flowing beyond the RBC dam 232 and into the platelet collect well 236 is reduced.

In the event that the location of the interface between the RBCs and plasma progresses radially outward, the flow through the control port tube 512 will increase since the quantity of RBCs exiting the blood processing vessel 352 through the control port 512 will have decreased. Since the flow through the return tube 546 must remain the same, this results in a decrease in the flow of RBCs through the RBC outlet tube 540. This reduces the number of RBCs being removed from the channel 208 such that both the interface between the RBCs and the buffy coat in relation to the RBC dam 232 and the interface between the RBCs and the plasma both move radially inwardly. That is, this changes the radial position of each of these interfaces.

The above-described tubes which interface with the blood processing vessel 352 of the embodiment of FIGS. 2A–2B and 8A, namely the blood inlet tube 412, the platelet collect tube 424, the plasma outlet tube 476, the return tube 546, each pass downwardly through the central opening 328 in the channel housing 204. A tubing jacket 548 is disposed about these various tubes and protects such tubes during rotation of the channel housing 204. These tubes are also fluidly interconnected with the extracorporeal tubing circuit 10 which again provides for fluid communication between the donor/patient 4 and the blood processing vessel 352.

The blood processing vessel 352/352a also includes features for loading and unloading the same from the channel 208. Referring back to FIG. 16, the vessel 352/352a includes at least one and preferably a plurality of tabs 552. The tabs 552 may be integrally formed with the blood processing vessel 352/352a (e.g., formed by the seal which also forms the upper seal 380). However, the tabs 552 may also be separately attached. The tabs 552 nonetheless extend vertically above the fluid-containing volume of the blood processing vessel 352/352a, preferably a distance such that the tabs 552 actually project above the channel housing 204. The tabs 552 thereby provide a convenient non-fluid-containing structure for the operator to grasp and load/remove the blood processing vessel 352/352a into/from the channel 208 (e.g., they provide structure for the operator to grasp which has had no blood-related flow therethrough during the apheresis procedure). The tabs 552 are particularly useful since there may be resistance provided to a loading and an unloading of the blood processing vessel 352/352a into/from the channel 208.

Centrifuge Rotor Assembly

The channel assembly 200 is mounted on the centrifuge rotor assembly 568 which rotates the channel assembly 200 to separate the blood into the various blood component types by centrifugation. The centrifuge rotor assembly 568 is principally illustrated in FIGS. 24–25 and generally includes a lower rotor housing 584 having a lower gear 588. An input or drive shaft 576 is disposed within the lower rotor housing 584 and is rotatably driven by an appropriate motor 572. The input/drive shaft 576 includes a platform 580 mounted on an upper portion thereof and a rotor body 592 is detachably interconnected with the platform 580 such that it will rotate therewith as the input/drive shaft 576 is rotated by the motor 572.

The centrifuge rotor assembly 568 further includes an upper rotor housing 632 which includes a mounting ring 644 on which the channel housing 204 is positioned. In order to allow the channel housing 204 to rotate at twice the speed of the rotor body 592, the upper rotor housing 632 and lower rotor housing 584 are rotatably interconnected by a pinion assembly 612. The pinion assembly 612 is mounted on the rotor body 592 and includes a pinion mounting assembly 616 and a rotatable pinion 620. The pinion 620 interfaces with the lower gear 588 and a driven gear 636 which is mounted on the mounting ring 644. The gear ratio is such that for every one revolution of the rotor body 592 the upper rotor housing 632 rotates twice. This ratio is desired such that no rotary seals are required for the tubes interfacing with the blood processing vessel In one embodiment, the lower gear 588, the pinion 620, and the driven gear 636 utilize straight bevel gearing.

The centrifuge rotor assembly 568 is also configured for easy loading of the blood processing vessel 352/352a in the channel 208 of the channel housing 204. In this regard, the rotor body 592 includes a generally L-shaped blood processing vessel loading aperture 597. The aperture 597 includes a lower aperture 600 which extends generally horizontally into the rotor body 592 through its sidewall 596 of the rotor body 592, but only partially therethrough. The perimeter of the lower aperture 600 is defined by a left concave wall 601, a back concave wall 603, and a right concave wall 602.

The loading aperture 597 also includes an upper aperture 598 which intersects with the lower aperture 600 at 599 and extends upwardly through an upper portion of the rotor body 592. The upper aperture 598 is aligned with a generally vertically extending central opening 640 in the upper rotor housing 632. As noted above, the channel housing 204 also includes a central opening 328. As such, a blood processing vessel 352/352a may be folded if desired, inserted into the lower aperture 600, deflected upwardly by the back concave wall 603, through the upper aperture 598, through the central opening 640 in the upper rotor housing 632, and through the central opening 328 of the channel housing 204. The operator may then grasp the blood processing vessel 352/352a and load the same in the channel 208.

The centrifuge rotor assembly 568 includes a number of additional features to facilitate the loading of the blood processing vessel 352/352a in the channel 208. Initially, the pinion 620 is radially offset in relation to the lower aperture 600 of the rotor body 592. In one embodiment, a reference axis laterally bisects the lower aperture 600 and may be referred to as the "zero axis". The axis about which the pinion 620 rotates is displaced from this "zero axis" by an angle α of about 40 degrees in the illustrated embodiment (see FIG. 25A). An angle α of −40 degrees could also be used. Positioning the pinion 620 at an angle of "greater" than ±40 degrees will result in the pinion 620 beginning to interfere with the access to the loading aperture 597. Although the angle α may be less than 40 degrees and may even be 0 degrees, having the pinion 620 at 0 degrees will result in the counterweights 608 potentially interfering with the access to the loading aperture 597. Based upon the foregoing, in FIG. 25 the pinion assembly 612 has therefore been rotated about the axis which the centrifuge rotor assembly 568 rotates for ease of illustration.

Since only a single drive gear is utilized to rotate the upper rotor housing 632 relative to the rotor body 592, an upper counterweight 604 and lower counterweight 608 are disposed or detachably connected to the rotor body 592 proximate the upper and lower extremes of the lower aperture 600. Due to the offset positioning of the pinion 620 in relation to the lower aperture 600, the upper and lower counterweights 604, 608 are also radially offset in relation to the lower aperture 600. That is, the upper and lower counterweights 604, 608 are "off to the side" in relation to the lower aperture 600 such that access thereto is not substantially affected by the counterweights 604 and 608. A tube mounting arm 624 is also appropriately attached to the rotor body 592 and engages the tubing jacket 548. The tubing mounting arm 624 serves to further the rotational balance of the rotor body 592.

Figure 25A:
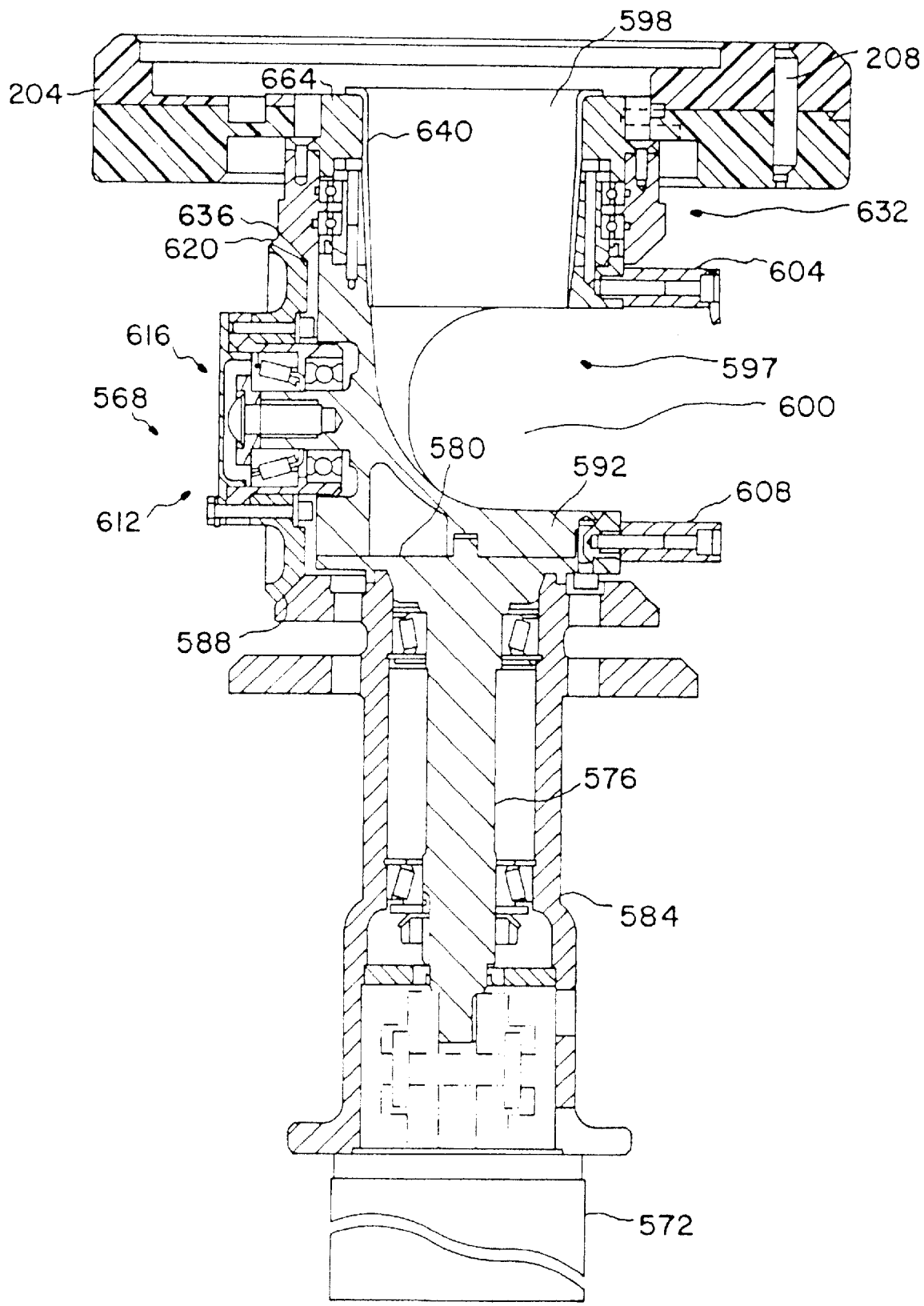
FIG. 25A is a longitudinal cross-sectional view of the rotor assembly of FIG. 24.
Figure 25B:
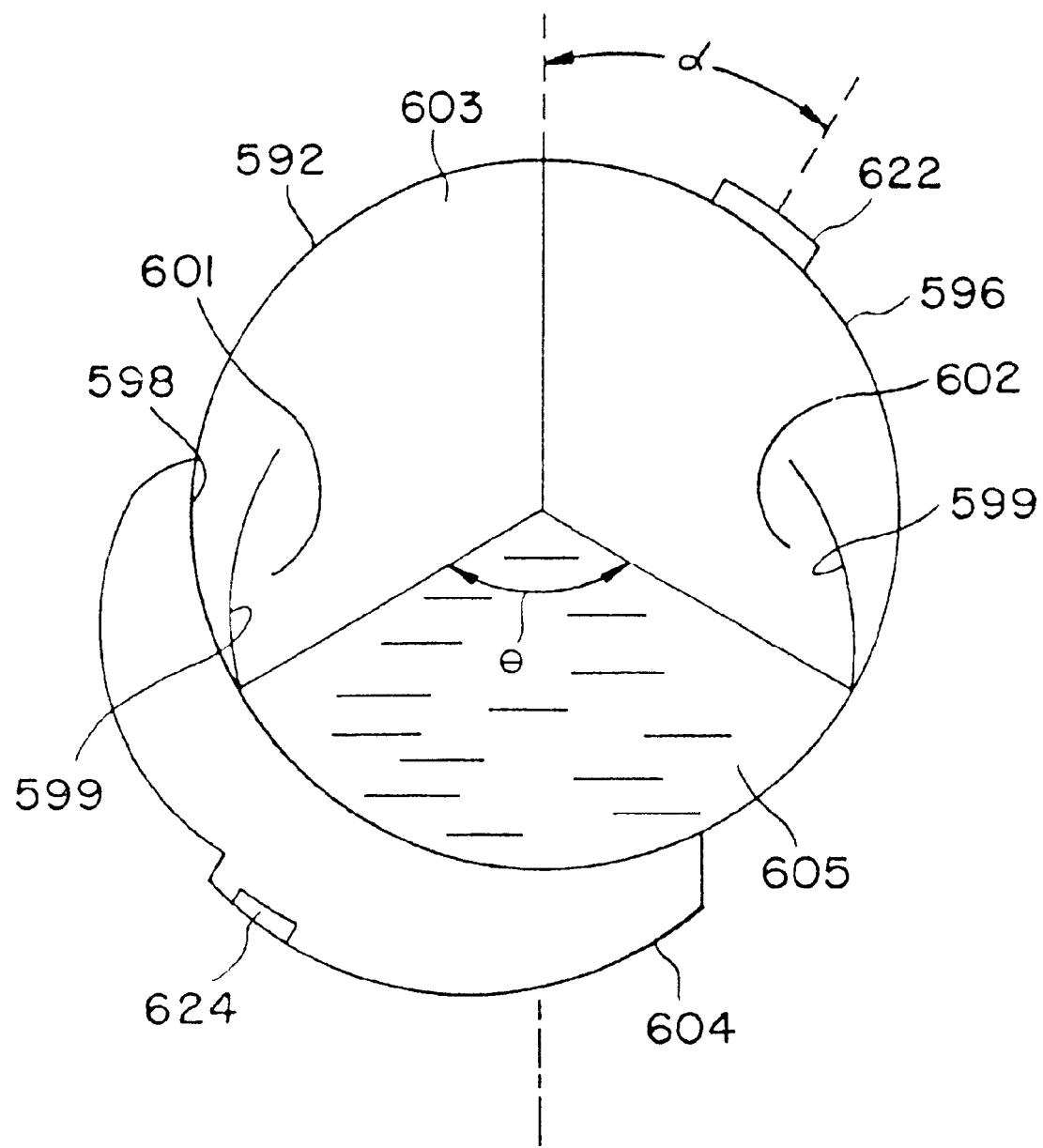
FIG. 25B is a top view of the rotor body of the rotor assembly of FIG. 24.
Figure 25C:
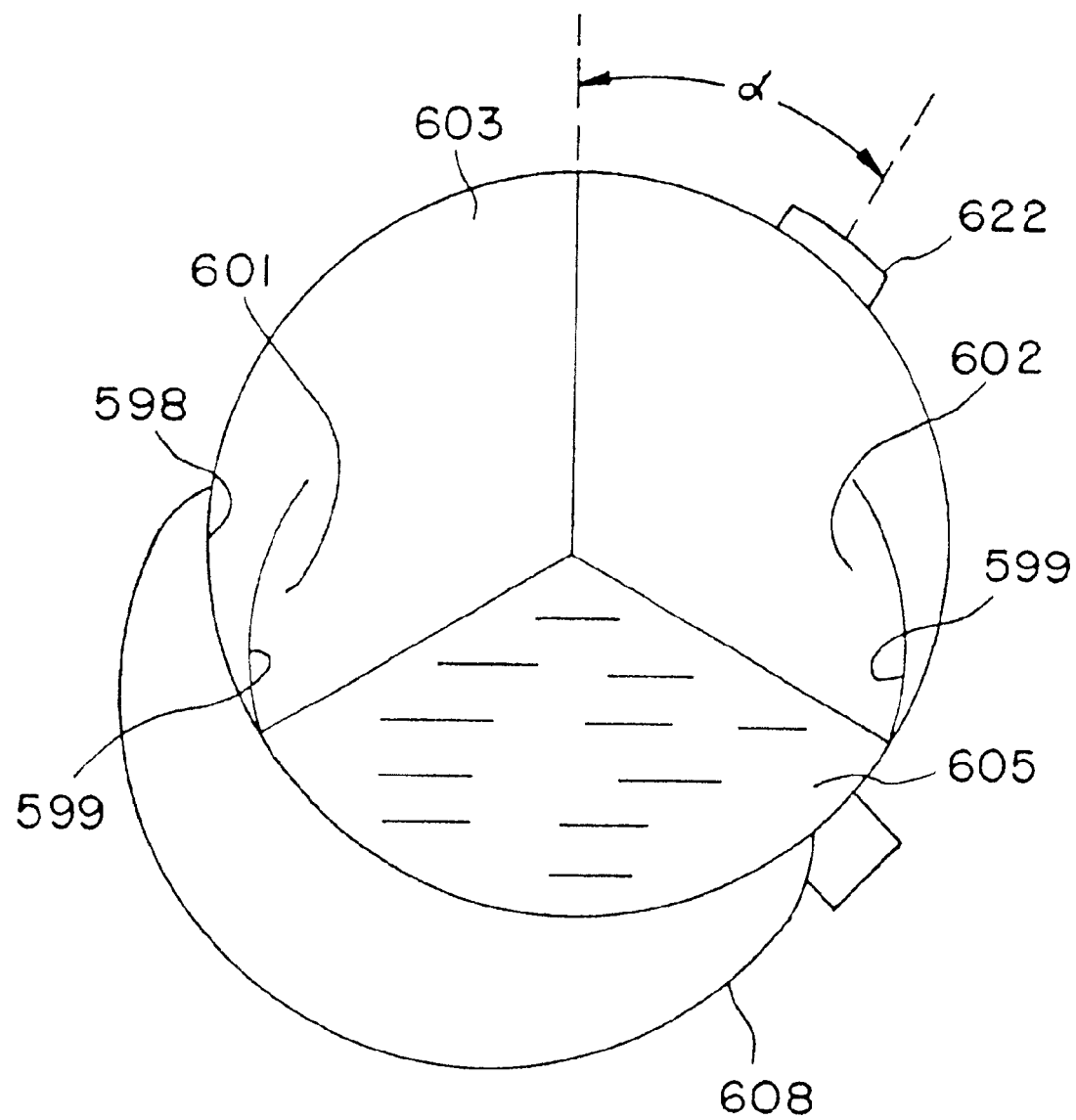
FIG. 25C is a top view of the rotor body of the rotor assembly of FIG. 24 with the upper counterweight removed so as to illustrate the lower counterweight.
Figure 25D:
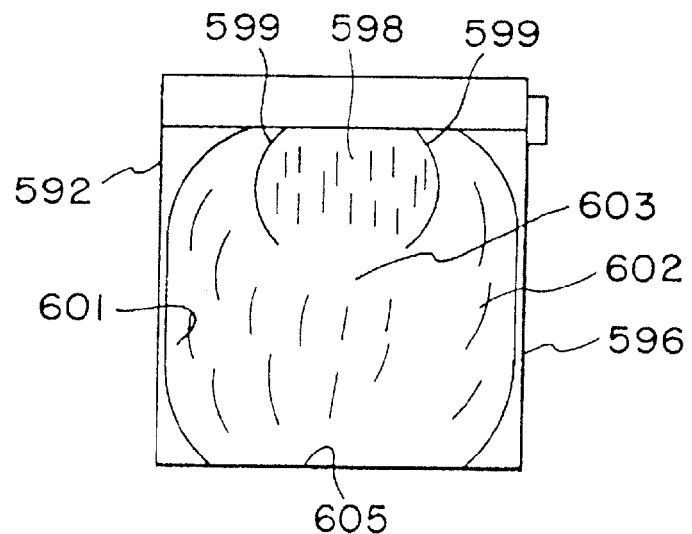
FIG. 25D is a front view of the rotor body of FIG. 24.
Figure 25E:
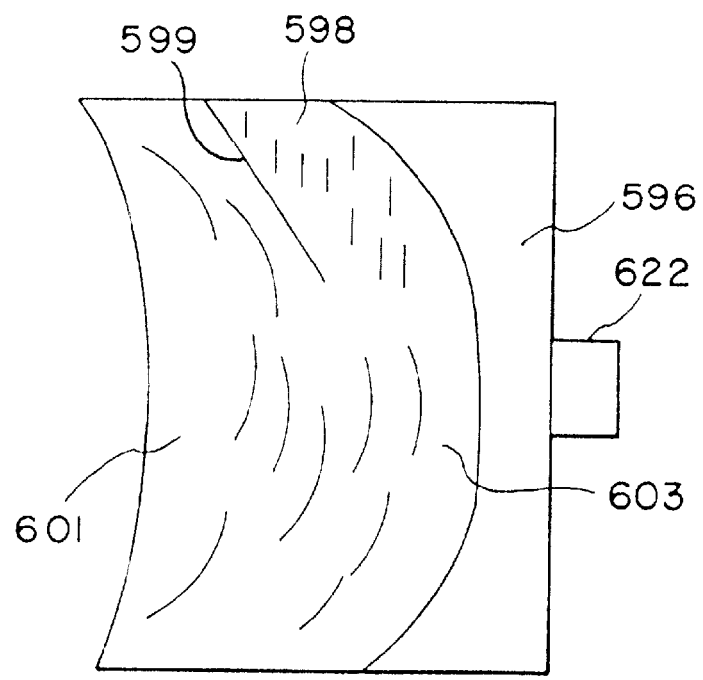
FIG. 25E is an isometric view of the left side of the blood processing vessel aperture in the rotor body of FIG. 24.
Figure 25F:
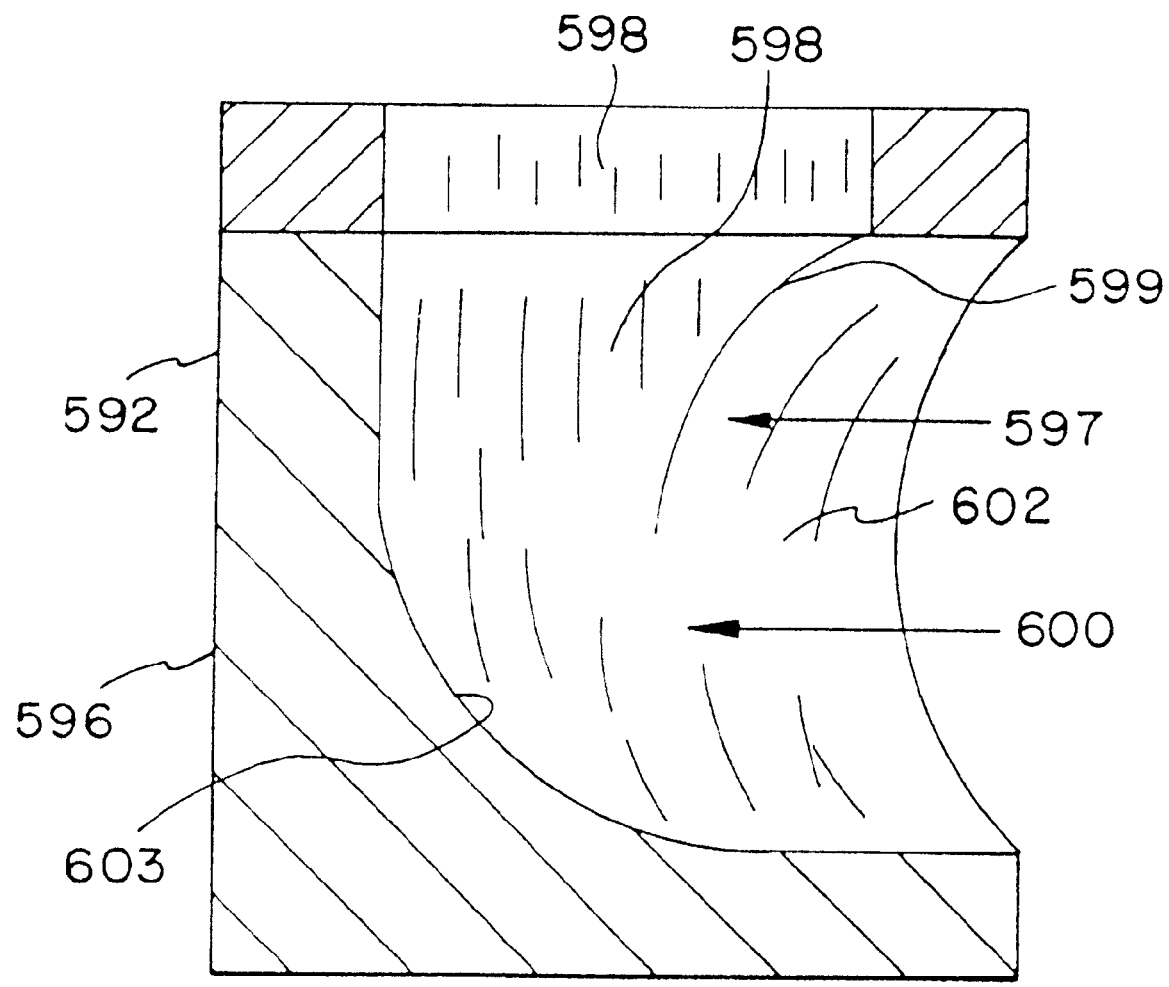
FIG. 25F is a cross-sectional view of the rotor body of FIG. 24.

Another feature of the centrifuge rotor assembly 568 which contributes to the loading of the blood processing vessel 352/352a upwardly through the rotor body 592 is the size of the lower aperture 600. As illustrated in FIG. 25B, the "width" of the lower aperture may be defined by an angle θ which may range from about 70 degrees to about 90 degrees, and in the illustrated embodiment is about 74 degrees. The back wall 603, left wall 601 and right wall 602 are also defined by a radius ranging from about "1.75"to about "2.250", and in the illustrated embodiment this radius is between about "2.008" and about "2.032".

Apheresis Protocol

A first alternative protocol which may be followed for performing an apheresis procedure on a donor/patient 4 utilizing the above-described system 2 will now be summarized. Initially, an operator loads the cassette assembly 110 onto the pump/valve/sensor assembly 1000 of the blood component separation device 6 and hangs the various bags (e.g., bags 104, 94, 84, and/or 954) on the blood component separation device 6. The operator then loads the blood processing vessel 352 (e.g., FIGS. 2A, 2B and 8a) within the channel 208 which is disposed on the channel housing 204 which is in turn mounted on the centrifuge rotor assembly 568, particularly the mounting ring 644. More specifically, the operator may fold the blood processing vessel 352 and insert the same into the blood processing vessel loading aperture 597 on the rotor body 592. Due to the arcuately-shaped, concave configuration of the loading aperture 597, specifically the lower aperture 600, the blood processing vessel 352 is deflected upwardly through the upper aperture 598, the central opening 640 in the upper rotor housing, and the central opening 328 in the channel housing 294. The operator then grasps the blood processing vessel 352 and pulls it upwardly away from the channel housing 204.

Once the blood processing vessel 352 has been installed up through the centrifuge rotor assembly 568, the operator loads the blood processing vessel 352 into the channel 208 on the channel housing 204. The operator generally aligns the blood processing vessel 352 relative to the channel 208 (e.g., such that the blood inlet port 392 is vertically aligned with the blood inlet slot 224, such that the platelet collect port 420 is vertically aligned with the platelet support recess 249 and the platelet collect tube recess 254 (in the embodiment of FIGS. 2A–2B), such that the plasma outlet port 456 is vertically aligned with the plasma outlet slot 256, such that the control port 492 is vertically aligned with the control port slot 264 (also per FIGS. 2A–2B), and such that the RBC outlet port 520 is vertically aligned with the RBC outlet slot 272). Once again, the interconnection of the first connector 360 and second connector 368, which is preferably fixed, facilitates the loading of the blood processing vessel 352, as well as the existence of the chamfer 210.

With the blood processing vessel 352 properly aligned, the operator directs the blood processing vessel 352 through the reduced width upper channel section 292 of the channel 208 until the blood processing vessel 352 hits the channel base 220. In this case, the longitudinal extent of the blood processing vessel 352 located in the portion of the channel 208 which includes the first stage 312, the RBC dam 232, and the platelet/plasma collect or second stage 316 will be disposed as follows: 1) the upper seal 380 will be disposed in the upper channel section 292; 2) the fluid-containing volume of the blood processing vessel 352 will be disposed in the mid channel section 300; and 3) the lower seal 384 will be disposed in the lower channel section 304. The above-noted ports will also be disposed in their respective slots in the channel housing 204 by the operator at this time. Moreover, the shield 408 associated with the blood inlet port assembly 388 will be disposed in the recess 228 associated with the blood inlet slot 224. Similarly, the shield 538 associated with the RBC outlet port assembly 516 will be disposed in the recess 276 associated with the RBC outlet slot 272. Furthermore, the shield 508 associated with the control port assembly 488 will be disposed in the recess 268 associated with the control port slot 264 (according to the embodiment of FIGS. 2A–2B).

With the extracorporeal tubing circuit 10 and the blood processing vessel 352 loaded in the above-described manner, the circuit 10 and vessel 352 may first be pressure-tested to verify that there are no leaks. The donor/patient 4 is then fluidly interconnected with the extracorporeal tubing circuit 10 (by inserting an access needle 32 into the donor/patient 4). Moreover, the anticoagulant tubing 54 is primed between the anticoagulant supply (which interfaces with the spike drip member 52) and the manifold 48. Furthermore, blood return/replacement delivery tubing 28 is primed with blood from the donor/patient 4 by running the blood return/replacement delivery peristaltic pump 1090 pump in reverse to draw blood from the donor/patient 4, through the blood return tubing 28, and into the reservoir 150 until blood is detected by the low level sensor 1320.

The blood processing vessel 352 must also be primed for the apheresis procedure. In one embodiment, a blood prime may be utilized in that blood will be the first liquid introduced into the blood processing vessel 352. The flow of blood from the donor/patient 4 to the extracorporeal tubing circuit 10 is initiated with the centrifuge rotor assembly 568 rotating the channel housing 204 at a rotational velocity of from about 150 RPM to about 250 RPM for a rotor diameter of about 10", and typically about 200 RPM. This lower rotational velocity not only reduces the potential for air locks developing the in the blood processing vessel 352, but also minimizes any preheating of the blood processing vessel 352. The rotational velocity in this "first stage" need not be fixed, but may vary.

Once the flow of blood reaches the blood processing vessel 352, the rotational speed of the channel housing 204 is increased from about 1,500 RPM to about 2,500 RPM for a rotor diameter of about 10", preferably about 2000 RPM, such that blood being provided to the blood processing vessel 352 will be separated into the various blood component types even during the priming procedure. Once again, in this "second stage", the rotational velocity need not be fixed, but may vary. In order for a blood prime to be successful in the first embodiment, a flow must be provided to the control port assembly 488 before any RBCs flows beyond the RBC dam 232 in a clockwise direction. This is again provided by the configuration of the channel 208. When there is no control port assembly 488 (see FIGS. 2C–2D), a plasma flow first desirably reaches the RBC/control port 520 before RBCs flow over or beyond the RBC dam 232 (although this is less important in this embodiment as described below).

Importantly, during this "second stage" of the blood priming procedure, air present in the blood processing vessel 352 is removed from the blood processing vessel 352 and due to the noted rotational velocities in this "second stage", the potential for air locks is also reduced. More specifically, air which is present in the blood processing vessel 352 is less dense than the whole blood and all of its blood component types. As noted above, the radially inwardmost portion of the inner channel wall 212 is at the intersection between the plasma outlet slot 256 and the inner channel wall 212. Consequently, the air present in the blood processing vessel 352 collects near the plasma outlet port 456 and is removed from the blood processing vessel 352 through the plasma outlet tubing 476, and is provided to the vent bag 104.

When the blood processing vessel 352 contains blood and/or blood components throughout its entirety, the rotational velocity of the channel housing 204 is increased to its normal operation speed from about 2,750 RPM to about 3,250 RPM for a rotor diameter of about 10", and preferably about 3,000 RPM. This completes the blood priming procedure.

During the above-noted blood priming procedure, as well as throughout the remainder of the apheresis procedure, blood component types are separated from each other and removed from the blood processing vessel 352 on a blood component type basis. At all times during the apheresis procedure, the flow of whole blood is provided to the blood processing vessel 352 through the blood inlet port assembly 416 and is directed to the first stage 312. The control port dam 280 again reduces the potential for blood flowing in a counterclockwise direction in the channel 208 in the FIG. 8A embodiment. Other detailed differences of blood priming between the embodiments disclosed herein will be further addressed below.

In the first stage 312, blood is separated into a plurality of layers of blood component types including, from the radially outermost layer to the radially innermost layer, RBCs, WBCs, platelets, and plasma. As such, the RBCs sediment against the outer channel wall 216 in the first cell separation stage 312. By configuring the RBC dam 232 such that it is a section of the channel 210 which extends further inwardly toward the rotational axis 324 of the channel housing 204, this allows the RBC dam 232 to retain separated red blood cells in the first stage 312.

Separated RBCs are removed from the first stage 312 utilizing the above-noted configuration of the outer channel wall 216 which induces the RBCs to flow in a counterclockwise direction (e.g., generally opposite to the flow of blood through the first cell separation stage 312). That is, the portion of the channel 208 proximate the RBC outlet port assembly 516 is disposed further from the rotational axis 324 of the channel housing 204 than that portion of the channel 210 proximate the RBC dam 232. As such, separated RBCs flow through the first stage 312 in a counterclockwise direction along the outer channel wall 216, past blood inlet port assembly 388 on the blood processing vessel 352 and to an RBC outlet port assembly 516. Since the vertical slot 404 of the blood inlet port 392 is substantially parallel with the inner channel wall 212, the outer channel wall 216, the inner sidewall 372 of the blood processing vessel 352 and the outer sidewall 376 of the blood processing vessel 352, since it directs the flow of blood in a clockwise direction in the channel 208 and thus toward the RBC dam 232, and since it is disposed proximate the inner channel wall 212, the introduction of blood into the blood processing vessel 352 does not substantially affect the flow of RBCs along the outer channel wall 216. Consequently, RBCs effectively flow undisturbed past the blood inlet port 392 and to the RBC outlet port assembly 516 for removal from the blood processing vessel 352. These RBCs may either be collected and/or provided back to the donor/patient 4.

An embodiment such as the first embodiment described herein (corresponding to FIGS. 2A–2B and FIG. 8A) may make use of the fact that platelets are less dense then RBCs and are thus able to flow beyond the RBC dam 232 when the RBC/buffy coat interface is disposed sufficiently close to the dam 232 (i.e., sufficiently radially inwardly disposed to be near the top of the dam 232). These platelets would then flow to the platelet collect well 236 in platelet-rich plasma where they are removed from the blood processing vessel 352 by the platelet collect port assembly 416. Again, the blood processing vessel 352 via the support 428 and the outer channel wall 216 would collectively define the platelet collect well 236 when the blood processing vessel 352 is pressurized. That is, part of the platelet collect well 236 is defined by the lower face 240 and side faces 244, 248 formed in the outer channel wall 216, while the remainder thereof is defined by the second face 436 of the support 428 when the support 428 is moved into a predetermined position within and against portions of platelet support recess 249 upon pressurization of the blood processing vessel 352.

Platelet-poor plasma is less dense than the platelets and would continue to flow in a clockwise direction through the second stage 316 to the plasma outlet port assembly 452 where at least some of the plasma is removed from the blood processing vessel 352. This plasma may be collected and/or returned to the donor/patient 4. However, some of the plasma flow continues in the clockwise direction into and through the third stage 320 to the control port assembly 488 to provide for automatic control of the location of the interface between the RBCs and platelets in the above-described manner. As described further below, preferably all of the plasma which flows over the RBC dam 232 in the second embodiment herein (FIGS. 2C–2D) would be platelet-poor and flow to the plasma outlet port assembly 452 as above, as well as to the RBC/control outlet port 520 even though there is no control port assembly 488.

Platelet/RBC (and Potential Plasma) Collection

As noted, a preferred blood apheresis system 2 provides for contemporaneous separation of a plurality of blood components during blood processing, including the separation of red blood cells (RBCs), platelets and plasma. In turn, such separated blood components may be selectively collected in corresponding storage reservoirs (or bags) or immediately returned to the donor/patient 4 during a blood return submode. In this regard, and in one approach where at least platelets and/or both platelets and RBCs (and/or potentially plasma) are to be collected (see the embodiment of FIGS. 2A–2B), blood apheresis system 2 may be advantageously employed to collect platelets, and if desired separated plasma, during a time period(s) separate from the collection of red blood cells. In this manner, the collection of both high quality platelet units and high quality red blood cell units can be realized.

Moreover, the procedures described herein are preferably carried out using blood priming of extracorporeal tubing circuit 10 and blood processing vessel 352. Also, the preferred blood processing here provides for the collection of platelets in reservoir 84 during a first period and the collection of red blood cells in reservoir 954 during a second period (FIGS. 2A–2B). Plasma collection in reservoir 94 may also be selectively completed during the first period. During the platelet blood processing period and successive RBC collection procedure, blood component separation device 6 will control the initiation and termination of successive blood removal and blood return submodes, as described hereinabove. Additionally, blood component separation device 6 will control the platelet and RBC collection processes according to a predetermined protocol, including control over the divert valve assemblies 1100, 1110 and 1120 of the pump/valve/sensor assembly 1000.

More particularly, following blood priming, blood separation control device 6 provides control signals to pump/valve/sensor assembly 1000 so that in the embodiment of FIGS. 2A–2B, platelet divert valve assembly 1100 diverts the flow of separated platelets pumped through platelet outlet tubing 66 and platelet tubing loop 142 into platelet collection tubing 82 for collection in reservoir 84. If plasma collection is desired, blood component separation device 6 also provides control signals so that plasma divert valve 1110 diverts the flow of separated plasma pumped through plasma outlet tubing 68 and plasma tubing loop 162 into plasma collector tubing 92 for collection in reservoir 94. Additionally, RBC/plasma divert valve assembly 1120 will continue to divert the flow of separated RBCs flowing through outlet tubing 64 through return tubing loop 172 and into blood return reservoir 150. Platelet collection is carried out as previously discussed hereinabove, with a packing factor in the second stage of vessel 352 maintained at between about 4 and 15, and most preferably at about 13. When the desired volumes of platelets and plasma have been collected, blood component separation device 6 will selectively control divert assemblies and 1110 to divert the flow of platelets and plasma into reservoir 150.

Preferably following completion of platelet and plasma collection (in the embodiment of FIGS. 2A–2B), the RBC collection procedure is initiated via control signals provided by blood collection device 6. Such RBC collection procedure includes a setup phase and a collection phase. During the setup phase, the blood apheresis system 2 is adjusted to establish a predetermined hematocrit in those portions of the blood processing vessel 352 and extracorporeal tubing circuit 10 through which separated RBCs will pass for collection during the RBC collection phase.

More particularly, during the setup phase, and in order to realize a predetermined hematocrit of at least about 75%, for example, and more preferably at about 80%, the packing factor in the first stage 312 of the blood processing vessel 352 is established at between about 11 and about 21, and most preferably at about 13. Additionally, the AC ratio (i.e., the ratio between the inlet flow rate to vessel 352 (including whole blood plus anticoagulant AC) and the AC flow rate into tubing circuit 10) will be established within the range of about 6 to 16, and most preferably at about 8.14 (particularly in the U.S.). Further, the total uncollected plasma flow rate through blood processing vessel 352 and extracorporeal tubing circuit 10 will be established at a predetermined level. These adjustments are carried out in simultaneous fashion to establish the desired hematocrit in an expeditious manner. As will be appreciated, the adjusted AC ratio and predetermined hematocrit should be maintained during the subsequent RBC collection phase.

During the set-up phase, blood component separation device 6 provides appropriate control signals to the pump/valve/sensor assembly 1000 such that all separated blood components flowing out of processing vessel 352 will pass to return reservoir 150. Also, blood component separation device 6 will continue operation of blood inlet pump assembly 1030, including operation during each blood return submode.

In order to establish the desired packing factor, the operating speed of centrifuge rotor assembly 568 may be selectively established via control signals from blood component separation device 6, and the blood inlet flow rate to vessel 352 may be selectively controlled via control by blood component separation device 6 over pump assembly 1030. More particularly, as mentioned above, increasing the rpms of centrifuge rotor assembly 568 and/or decreasing the inlet flow rate will tend to increase the packing factor, while decreasing the rpms and increasing the flow rate will tend to decrease the packing factor. As can then be appreciated, the blood inlet flow rate to vessel 352 is effectively limited by the desired packing factor.

To establish the desired AC ratio, blood component separation device 6 provides appropriate control signals to anticoagulant peristaltic pump 1020 so as to introduce anticoagulant into the blood inlet flow at a predetermined rate, as previously described hereinabove. Relatedly, in this regard, it should be noted that the inlet flow rate of anticoagulated blood to blood processing vessel 352 is limited by a predetermined, maximum acceptable anticoagulant infusion rate (ACIR) to the donor/patient 4. As will be appreciated by those skilled in the art, the predetermined ACIR may be established on a donor/patient-specific basis (e.g., to account for the particular total blood volume of the donor/patient 4).

To establish the desired total uncollected plasma flow rate out of blood processing vessel 352, blood collection device 6 provides appropriate control signals to plasma pump assembly 1060 and platelet pump assembly 1040. Relative to platelet collection, such control signals will typically serve to increase plasma flow through plasma outlet port 456, and thereby reduce plasma flow with RBCs through RBC outlet port 520. This serves to increase the hematocrit in the separated RBCs. Additionally, it is preferable for blood processing device 6 to provide control signals to platelet pump assembly 1040 so as to establish a predetermined flow rate wherein platelets and some plasma pass together through platelet port 420, thereby reducing platelet clumping downstream in tubing circuit 10. In this regard, such predetermined rate will be limited by the diameter of the platelet outlet tubing 66 and the size of the internal channels (e.g., 140*a*, 140*b*) within molded cassette 110.

In one embodiment, where centrifuge rotor assembly 568 defines a rotor diameter of about 10 inches, and where a blood processing vessel 352 (FIGS. 2A–2B) is utilized, as described hereinabove, it has been determined that channel housing 204 can be typically driven at a rotational velocity of about 3000 rpms to achieve the desired hematocrit during the setup and blood collection phases. Correspondingly, the blood inlet flow rate to vessel 352 should be established at or below about 64.7 ml/min. The desired hematocrit can be reliably stabilized by passing about two whole blood volumes of either reservoir 150 (in cassette 110) or reservoir 352 through the respective reservoir before the RBC collection phase is initiated.

To initiate the RBC collection phase, blood component separation device 6 provides an appropriate control signal to RBC/plasma divert valve assembly 1120 so as to direct the flow of RBCs removed from blood processing vessel 352 into RBC collection reservoir 954. Both the platelet divert valve assembly 1100 and plasma divert valve assembly 1110 remain in a position to direct flow into reservoir 150 for return to donor/patient 4 during blood return submodes. In the later regard, it is preferable that, during blood return submodes of the RBC collection phase, blood collection device 6 provide appropriate control signals so as to stop the operation of all pump assemblies other than return pump assembly 1090. In this regard, stoppage of inlet pump assembly 1030 avoids recirculation of uncollected blood components into vessel 352 and resultant dilution of separated RBC components within vessel 352.

As will be appreciated, in the present invention separated RBCs are not pumped post-separation out of vessel 352 for collection, but instead are pushed out vessel 352 and through extracorporeal tubing circuit 10 by the pressure of the blood inlet flow to vessel 352. Consequently, trauma to the collected RBCs is minimized.

During the RBC collection phase, the inlet flow into vessel 352 is limited by the above-noted maximum acceptable ACIR to the donor/patient 4. The desired inlet flow rate is also limited by that necessary to maintain the desired packing factor, as also discussed. In this regard, it will be appreciated that, relative to the setup phase, the inlet flow rate may be adjusted slightly upwards during the RBC collection phase since not all anticoagulant is being returned to the donor/patient 4. That is, a small portion of the AC remains with the plasma that is collected with the RBCs in RBC reservoir 954.

Following collection of the desired quantity of red blood cells, blood separation device 6 may provide a control signal to divert assembly 1120, so as to divert RBC flow to reservoir 150. Additionally, if further blood processing is not desired, rinseback procedures may be completed. Additionally, the red blood cell reservoir 954 may be disconnected from the extracorporeal tubing circuit 10. A storage solution may then be added. Such storage solution may advantageously facilitate storage of the RBCs for up to about 42 days at a temperature of about 1–6 degrees C. In this regard, acceptable storage solutions include a storage solution generically referred to in the United States as Additive Solution(AS-3), available from Medsep Corp. located in Covina, Calif.; and a storage solution generically referred to in Europe as "SAGM", available from MacoPharma located in Tourcoing, France.

The storage solution may be contained in a separate storage solution bag that can be selectively interconnected to the RBC collection bag 954. Such selective interconnection may be provided via sterile-docking tubing utilizing a sterile connecting device. By way of example, one such sterile connecting device to interconnect tubing is that offered under the trade name "SCD 312" by Terumo Medical Corporation located in Somerset, N.J. Alternatively, selective interconnection may be established utilizing the sterile barrier filter/spike assembly 956. The use of assembly 956 facilitates the maintenance of a closed system, thereby effectively avoiding bacterial contamination. By way of example, the mechanical, sterile barrier filter in assembly 956 may include a porous membrane having 0.2 micron pores.

In order to ensure the maintenance of RBC quality, the RBC collection bag 954, the storage solution and the anticoagulant used during blood processing should be compatible. For example, RBC collection reservoir 954 may comprise a standard PVC DEHP reservoir (i.e., polyvinyl chloride-diethylhexylphthallate) offered by Medsep Corporation. Alternatively, a citrated PVC reservoir may be employed. Such reservoir may utilize a plasticizer offered under the trade name "CITRIFLEX B6" by Moreflex located in Commerce, Calif. Further, the anticoagulant utilized in connection with the above-described platelet collection and red blood cell collection procedures may be an acid citrate dextrose-formula A (ACD-A).

After the storage solution has been added to the collected red blood cells in RBC reservoir 954, selective filtering may be desired to remove white blood cells. More particularly, for example, leukoreduction may be desired to establish a white blood cell count at $<5 \times 10^8$ white blood cells/unit (e.g., about 250 ml.) to reduce any likelihood of febrile nonhemolytic transfusion reactions. Further, such filtering may be desirable to achieve a white blood cell count of $<5 \times 10^6$ white blood cells/unit to reduce any risk of HLA (i.e., human leukocyte A) sensitization. If such leukoreduction is deemed appropriate, the red blood cell/storage solution mixture can be connected to a commercially available red cell filter/bag assembly so that red blood cells are gravity transferred from the collection bag 954 through a filter and into a new storage bag. Such commercially available red cell filter/bag kits include those available under the trade names "LEUKO- NET" or "r\LS" from Hemasure, Inc. located in Marlborough, Mass., and "RC 100", "RC50" and "BPF4" from Pall Corp. located in Glencove, N.Y.

Several advantages can be realized utilizing the above-described procedure for red blood cell collection. Such advantages include: consistency in final RBC product volume and hematocrit; reduced exposure of a recipient if multiple units of blood products are collected from a single donor/patient and transfused to a single recipient; reduced time requirements for RBC collection and for collection of double units of red blood cells if desired.

While one approach for platelet and RBC collection has been described above, other approaches using the embodiment of FIGS. 2A–2B will be apparent. By way of primary example, the described RBC collection procedure may be carried out following blood priming, and prior to platelet collection. Such an approach would advantageously allow RBC collection to occur in the course of AC ramping, thereby reducing total processing time requirements. That is, since AC ramping up to a predetermined level (e.g., increasing the AC ratio up to about 13) is typically gradually completed prior to the start of a platelet collection procedure (e.g., so as to maintain an acceptable ACIR), completing RBC collection procedures in the course of AC ramping would reduce the overall processing time for RBC and platelet collection. The RBC collection procedure could be completed when AC ramping reaches about 8.14, with AC ramping continuing thereafter. Alternately, RBC collection could occur in tandem with AC ramping, wherein the target AC ratio of about 8.14 would be established as an average effective ratio for the RBCs and plasma collected and mixed within reservoir 954.

Further, and as noted above, plasma collection could occur contemporaneous with RBC collection. Additionally, in this regard, plasma collection could occur during both platelet and RBC collection procedures, depending upon the volume of plasma product desired. Finally, it has been recognized that the present invention of embodiment of FIGS. 2a–2b may also be employable to simultaneously separate and collect both red blood cells and platelets, and if desired, plasma.

RBC/Plasma (Generally Non-platelet) Collection

As noted, a preferred blood apheresis system 2 also provides for continuous separation of red blood cells (RBCs) and plasma with various alternative collection options. For example, continuous separation may be provided with contemporaneous collection of both RBCs and plasma and/or with collection of either RBCs or plasma separately (see, e.g., the embodiment of FIGS. 2c–2d, 8B). In the preferred system, all the non-collected components are reinfused into the donor. Moreover, the separated blood components, RBCs and/or plasma (in the embodiments of FIGS. 2C–2D, e.g.), may be selectively collected, as described above, in corresponding storage reservoirs or immediately returned to the donor/patient 4 during a blood return/replacement fluid delivery submode. Note, the buffy coat components namely platelets and WBCs are not collected separately in this embodiment (FIGS. 2C–2D). Rather, these components preferably remain with the RBCs throughout these procedures and may either be filtered out subsequently, e.g., the WBCs through a leukoreduction filter (e.g., "COBE r\LS" filter) or the like; or may remain with the RBC product(s) as the platelets likely will, albeit without any deleterious effect. Preferably, the plasma product(s) hereof will remain platelet-poor and contain no WBCs (or at least within promulgated minimum safety ranges).

In the present embodiment (FIGS. 2C–2D and 8B), any of three options is primarily available, the collection of RBCs and plasma contemporaneously, or RBCs alone, or plasma alone (in either "alone" case, the collection may mean no other product is ever collected during that procedure, or no other product is collected at the same time; previous or subsequent collection is also possible). And in one approach where both plasma and RBCs are to be collected, blood apheresis system 2 may preferably be advantageously employed to collect RBCs and plasma contemporaneously for a first time period, and then collect either plasma or red blood cells for a second period. In this manner, the collection of both high quality plasma units and high quality red blood cell units can be realized. Target yields for both components are thus also preferably achieved or achievable. This may thus include double red blood cell products, for example. Note, a double product quantity is preferably configurable by the user; however, suggestions have been made for red blood cell products to be targeted at about 180 or 200 milliliters in pure form, which would be 225 or 250 ml at 80 hematocrit (i.e., including 20% plasma in the end product). Thus, a double RBC product under these suggestions would be about 360 or about 400 ml. in pure form and 450 to 500 at 80 hematocrit. Note, the 180 ml. suggestion may be based upon an understood concept of a whole blood donation unit of 450 ml.+10% which would provide about 60 grams of hemoglobin (Hb) or an average 180 ml. hematocrit (Ht) (see U.S. Federal Food and Drug Administration (FDA) suggestions). Other sizes can also be configured and collected based upon donor ability.

Replacement fluid(s) are preferably also optionally administrable within the procedures of the present invention using the embodiment of FIGS. 2C–2D. Sterile saline solution(s) and/or replacement/exchange plasma (and/or replacement/exchange red blood cells) are optional replacement fluids, inter alia, considered for use herein. Thus, if/when large fluid amounts of plasma and/or RBCs are taken from a donor/patient, replacement fluid(s) may be delivered in return to leave the donor/patient adequately hydrated i.e., replacement fluids may, in certain situations, qualify more product options from a given donor. For example, a particular donor may not qualify for a certain donation (e.g., a double RBC product) under normal conditions; however, with a replacement fluid infusion, that donor may then qualify for that donation.

Also, replacement fluids may also be used to avoid hypovolemia and like reactions. Bolus deliveries are also preferably deliverable herewithin. Exchange fluids (plasma and/or RBCs) may be used for therapeutic purposes as well. These alternatives are detailed further hereinbelow. Note first however that it is preferable that the one or more replacement fluid spike assembly(ies) 964 (964a/964b) are/ may be similar structurally and/or functionally to the anticoagulant spike assembly 50/52 shown and described hereinabove; but it is preferable that there be some distinction therefor safety reasons. For example, if a plastic spike is used for the anticoagulant line(s), it would then be preferable to include a metal or distinctly colored or shaped spike or spikes for the replacement fluid line(s) so that the operator will not confuse them and accidentally run anticoagulant into the replacement fluid system and thereby potentially seriously overload the donor/patient with anticoagulant.

The general set-up or initiation procedures described hereinabove for any and/or all other apheresis procedures are likewise and/or similarly carried out here to provide blood priming of extracorporeal tubing circuit 10a (FIGS. 2C–2D) and blood processing vessel 352a (FIG. 8B) (distinctions are described herein). The initiation of blood processing thereafter then provides for the collection of plasma in one or more reservoir(s) 94 and/or the collection of red blood cells in one or more reservoir(s) 954. Alternatively, either RBC collection in reservoir(s) 954 or plasma collection in reservoir(s) 94 may also be selectively completed in separate procedures. During either collection procedure, blood component separation device 6 preferably controls the initiation and termination of successive blood removal and blood return submodes, as described for example, in the preferred embodiment hereinabove (from and to the donor through level control in the cassette reservoir 150 using the two ultrasound fluid level detectors 1300, 1320, e.g.). Additionally, blood component separation device 6 will control the plasma and RBC collection processes according to predetermined protocols, preferably including control over the preferred valve assemblies 1100, 1110 and 1120 of the pump/valve/sensor assembly 1000, and/or the appropriate pumps 1020, 1030, 1040, 1060 and/or 1090.

Initially, blood priming is carried out generally as described hereinabove. However, as described here, a further step during priming is preferably instituted prior to starting component collection. During blood priming, it is still desirable that the component separation begin even during the priming stage, and that plasma flows over the RBC dam 232 and continues around to the plasma outlet port 456 and still further around to the RBC/control outlet 520 (see FIG. 8B); while RBCs build up behind the RBC dam 232 and flow in a counterflow direction back to the RBC/control outlet 520. (Note that the buffy coat elements preferably remain behind the dam 232 as well and flow to the RBC outlet port 520 with the RBCs; however, even though not preferred, sufficient functionality may nevertheless likely be retained even if some RBCs and/or buffy coat components flow over the dam 232 during priming. Potential WBC contamination of platelet collection apparatus is not here in issue, though it may be an issue for the plasma collection assembly, as well). The further priming step here is to then shut the plasma pump 1060 off for a period and thereby force a greater quantity of separated plasma toward the RBC/control outlet port and thereby force the high hematocrit separated RBCs out of the vessel 352a through the RBC/control outlet 520 until the plasma/RBC interface moves radially outward toward the orifice 536 of the outlet port 520. Eventually, plasma reaches the orifice 536 and spills thereinto and flows out through the outlet port 520. This plasma spilling into port 520 suggests it may also be called a spill port 520. Note, a greater quantity of plasma also fills the first stage 312 thus also contributing to the forcing of the RBC/plasma interface radially outward. Then, when the interface is established at or sufficiently adjacent the RBC orifice 536, as preferred here, the plasma pump may be automatically turned back on by the separation device 6 at a rate which maintains the RBC/plasma interface at or sufficiently adjacent the radial level of the RBC/control outlet orifice 536. In particular, it is desirable that the interface be maintained at this location such that a mixed flow of RBCs and plasma is maintained continuously through the RBC/control outlet port 520 such that the mixed flow of RBCs and plasma has reached and continues at a target hematocrit, here preferably at about 80. Maintenance by the device 6 of a particular relationship of the rate of plasma outflow generated by the plasma pump 1060 relative to the inlet rate of blood flow generated by the blood inlet pump 1030 provides for continuing the target output hematocrit of the RBC/plasma mixed flow through the RBC/control outlet port 520.

Following and/or contemporaneously with the blood priming phase as described hereinabove, blood separation control device 6 provides control signals to pump/valve/sensor assembly 1000 so that the replacement fluid lines may also be primed. In particular, replacement fluid valve assembly 1100 is opened and replacement fluid inlet pump 1040 is switched on to provide for the pumping of saline solution (or other replacement fluid(s)) through replacement fluid inlet tubing 962 and the replacement fluid tubing loop 142a into replacement fluid introduction tubing line 146 for initial collection in cassette reservoir 150, though this initial priming collection will likely and preferably does constitute a small amount of replacement fluid(s).

After priming is completed, yet still during the set-up phase, blood component separation device 6 may provide appropriate control signals to the pump/valve/sensor assembly 1000 such that all separated blood components flowing out of processing vessel 352a will first pass to return/delivery reservoir 150. Optionally, one or more cycles (preferably two) of separation and return of all blood components back to the donor may be performed before collection(s) and/or regular replacement fluid deliveries begin (this may be performed in order to stabilize the hematocrit in the first stage of vessel 352a). Any replacement fluid(s) collected in reservoir 150 during priming (again, likely very small amounts) may also be delivered to the donor/patient at this time. Also, blood component separation device 6 may continue operation of blood inlet pump assembly 1030 during one or more these initial blood component return submodes.

Then, the process of collection may begin. If plasma collection is not desired, plasma divert assembly 1110 maintains the flow of separated plasma from the vessel 352a to the reservoir 150 for return to the donor/patient 4. However, if plasma collection is desired (either alone or contemporaneously with RBCs), blood component separation device 6 may provide control signals so that plasma divert valve assembly 1110 switches to divert the flow of separated plasma pumped from vessel 352a through plasma outlet tubing 68 and plasma tubing loop 162 into plasma collector tubing 92 for collection in one or more plasma reservoir(s) 94. Additionally, if plasma is to be collected alone, RBC divert valve assembly 1120 will continue to maintain the flow of separated RBCs flowing from vessel 352a through outlet tubing 64 through return tubing loop 172 and into blood return reservoir 150. However, if RBCs are to be collected, alone or contemporaneously with plasma, then the RBC divert valve assembly 1120 switches to divert the flow of separated RBCs flowing from tubing 64 to and through spur 170b (of cassette 110) and into and through tubing line 952 to the one or more RBC collection reservoir(s) 954. No platelet collection is preferably carried out in this embodiment as previously discussed hereinabove.

Preferably during any of the collection processes involved with this embodiment (FIGS. 2C–2D), one or more replacement fluid(s) are also delivered to the donor/patient 4. Thus, whenever either divert valve assembly 1110 or 1120 is switched by the separation device 6 into a collection mode, then the replacement fluid inlet valve assembly 1100 may also be opened and the replacement fluid pump 1040 started to flow replacement fluids from the fluid source (not shown) through tubing line 962, cassette passageways 140c and 140d, and tubing loops 142a and 146 into the reservoir 150 (FIGS. 2C–2D). As a basic premise, the replacement fluid flow rate is equal to the total collection flow rate multiplied by the percentage of fluid desired to be given back to the donor/patient 4. This last factor is called a fluid balance percentage. Preferably, the rate of replacement fluid flow ($Q_{rf}$) is governed by the relationship of the total collection flow rate ($Q_{tot}$) minus the flow rate of the anticoagulant inflow ($Q_{ac}$) multiplied by the total fluid balance percentage (FB) ultimately delivered back to the donor/patient 4. In mathematical form;

$$Q_{rf} = [Q_{tot} - Q_{ac}] * FB;$$

Preferably, the fluid balance percentage is chosen within a limited range of 80% and(e.g., 80% representing the lessened amount of fluid the donor/patient 4 is given back, or has received at the end of the procedure relative to the donor/patient's donation amount, and 120% representing the additional amount of fluid given to the donor/patient 4 over the donation amount; thus, if 80% is chosen for example, then the donor/patient 4 ends the procedure with 80% of the donated fluid volume).

Note, a further option of fluid bolus infusion may be offered with a replacement fluid assembly such as that described herein. For example, a procedure for bolus infusion may be made available at any desired point in a procedure. As such, it may involve stopping all pumps except at least the replacement fluid inlet pump 1040 which delivers replacement fluid to the reservoir 150 at a selected infusion rate, then (with perhaps a slight delay to ensure a minimum level of fluid is present in the reservoir 150 prior to fluid return/delivery to the donor/patient), the return/delivery pump 1090 may be started to deliver the replacement fluid from the reservoir 150 to the donor/patient 4. A bolus button for initiating such a procedure may be permanently disposed on the separation device 6, and/or it may preferably be disposed on one or more selected touch screen(s) (see generally below) which may be displayed on the computer graphical interface 660. This may appear on an adjustment or troubleshooting screen, for example (see description(s) below).

When RBCs are collected contemporaneously with plasma, a packing factor in the first stage of vessel 352a is maintained preferably at 16. If RBCs are collected alone, then the packing factor is set between about 4 and 15, more preferably between 11 and 15, and most preferably at about 13. When the desired volumes of RBCs and/or plasma have been collected, blood component separation device 6 will preferably selectively control divert assemblies 1110 and 1120 to divert the respective flow of RBCs and/or plasma (whichever has reached its desired collected volume) into reservoir 150.

Following contemporaneous RBC and plasma collection (if this procedure is chosen), at which point either the target RBC volume/yield or the target plasma volume/yield (or both) has been reached, then the respective divert valve assembly 1110 or 1120 (or both) of the respective component whose target volume/yield has been reached is switched to divert flow of that separated component to flow to the reservoir Thus, if and when the target volume/yield of RBCs has been reached, then the divert valve assembly 1120 may be switched to return flow of separated RBCs to the reservoir 150, independent of and/or even if the plasma target volume/yield has not yet been reached. The same may be true in reverse, if and when the plasma target volume/yield has been reached, even if this occurs before the RBC target is reached, then the plasma divert valve assembly 1110 may be switched to flow the still incoming separated plasma to the reservoir 150. Then, collection of the other component is preferably continued until its target volume/yield is reached. Note, though either separated component may be collected first, and then the other components collected after the target volume/yield of the first component has been reached, it is preferable to start the procedure collecting both RBCs and plasma contemporaneously (assuming that a quantity of both products are desired from a given donor), and then switch to collecting only the component whose target volume/yield has not yet been reached when the other target has been reached.

Control over these switching steps after achieving either the RBC or the plasma target collection volumes/yields is initiated via control signals provided by blood collection/separation device 6 to the respective divert valve assemblies 1110 and 1120. Note also that the separation device 6 may make further adjustments as well upon switching from the contemporaneous collection of RBCs and plasma to the collection of only one such component. For example, the packing factor has been noted as preferably kept at 16 with a target hematocrit of 80 during collection of both RBCs and plasma contemporaneously. However, when the target volume/yield of one or the other blood component has been reached and then collection of only one component is continued, then the separation device 6 preferably adjusts to the preferred packing factor or hematocrit value as discussed herein. Specifically, if the plasma target has been reached, but RBC collection is to continue, the separation device preferably lowers the packing factor to the range disclosed herein, preferably to 11–15, or set even more preferably at 13 while maintaining a target hematocrit of 80. If, on the other hand, collection of plasma is instead to be continued after the target for RBCs has been reached, then the separation device 6 may reset the target hematocrit to approximately 55, for example, without concern for the resulting or actually occurring packing factor at this point.

Such RBC and/or plasma collection procedures may also include a setup phase and a collection phase. During a setup phase, the blood apheresis system 2 may be adjusted to establish a predetermined hematocrit in those portions of the blood processing vessel 352a and extracorporeal tubing circuit 10a through which separated RBCs will pass for collection during the RBC collection phase. More particularly, during the setup phase, and in order to realize a predetermined hematocrit of about 80%, the packing factor in the first stage 312 of the blood processing vessel 352a is established at between about 11 and about 21, and most preferably at about 16 for contemporaneous RBC and plasma collections, or 13 for RBC collections, alone. These are the preferred packing factors for collection phases of RBCs and plasma simultaneously, and RBCs alone, see discussions throughout. Additionally, the AC ratio (i.e., the ratio between the inlet flow rate to vessel 352a (including whole blood plus anticoagulant AC) and the AC flow rate into tubing circuit 10) will be established within the range of about 6 to 16, and most preferably at about 8.14 (in the United States) and/or 11 (in other countries). Further, the total uncollected plasma flow rate through blood processing vessel 352a and extracorporeal tubing circuit 10 may be established at a predetermined level. These adjustments are preferably carried out by controlling the speeds of the respective pumps and/or the centrifuge which may be adjusted in simultaneous fashion to establish the desired hematocrit in an expeditious manner. As will be appreciated, this adjusted AC ratio and predetermined hematocrit should be maintained during the subsequent RBC and plasma collection phase(s).

These adjustments will not affect the other collection control parameters where again, when collecting RBCs alone, the target hematocrit remains at 80, but the packing factor is preferably reduced to, for example, 11–13. This is similar to the RBC packing factor preference described above for the collection phase of RBCs after platelet collection has ceased (for the platelet/plasma/RBC embodiment; e.g., FIGS. 2A–2B, and corresponding description, above). Further still, when collecting plasma alone, the target hematocrit is preferably dropped to 55, and the packing factor in the first stage is not an issue (also as described hereinabove).

In order to establish the desired packing factor, the operating speed of centrifuge rotor assembly 568 may be selectively established via control signals from blood component separation device 6, and/or the blood inlet flow rate to vessel 352a may be selectively controlled via control by blood component separation device 6 over pump assembly 1030, and/or the plasma flow rate out through port 456 may similarly be controlled by device 6 through pump 1060. More particularly, increasing the rpms of centrifuge rotor assembly 568 and/or decreasing the inlet flow rate will tend to increase the packing factor, while decreasing the rpms and/or increasing the flow rate will tend to decrease the packing factor. As can be appreciated, the blood inlet flow rate to vessel 352a is effectively limited by the desired packing factor.

To establish the desired AC ratio, blood component separation device 6 provides appropriate control signals to anticoagulant peristaltic pump 1020 so as to introduce anticoagulant into the blood inlet flow at a predetermined rate, as previously described hereinabove. Relatedly, in this regard, it should be noted that the inlet flow rate of anticoagulated blood to blood processing vessel 352a is limited by a predetermined, maximum acceptable anticoagulant infusion rate (ACIR) to the donor/patient 4. As will be appreciated by those skilled in the art, the predetermined ACIR may be established on a donor/patient-specific basis (e.g., to account for the particular total blood volume of the donor/patient 4).

To establish the desired total uncollected plasma flow rate out of blood processing vessel 352a, it should be noted that when RBCs and plasma are collected simultaneously/contemporaneously, there is no uncollected plasma. Further, when plasma is collected alone, the uncollected plasma is that portion of the RBC/plasma outflow (i.e., that plasma flowing out RBC outlet port 520 with the RBC's through line 64) which may be determined by the hematocrit thereof. With a target hematocrit of about 55 in RBC line 64 during plasma collection alone, the uncollected plasma will constitute about 45% of that outflow. In either event, the blood collection device 6 provides appropriate control signals to plasma pump assembly 1060 to establish the desired total plasma flow rate, uncollected or collected. Relative to RBC collection, on the other hand, such control signals will typically serve to increase plasma flow through plasma outlet port 456, and thereby reduce plasma flow with RBCs through RBC outlet port 520. This serves to increase the hematocrit in the separated RBCs, to the target hematocrit of 80.

In one embodiment, where centrifuge rotor assembly 568 defines a rotor diameter of about 10 inches, and where a blood processing vessel 352a (see FIGS. 2C–2D and 8B) is utilized, as described hereinabove, it has been determined that channel housing 204 can be typically driven at a rotational velocity of about 3000 rpms to achieve the desired hematocrit during the both the setup and component collection phases. Correspondingly, the blood inlet flow rate to vessel 352a should preferably be established at below about 64.7 ml/min. The desired hematocrit can be reliably stabilized by passing about two whole blood volumes of vessel 352a through vessel 352a before the RBC and/or plasma collection phases are initiated.

To initiate an RBC collection phase, blood component separation device 6 pro an appropriate control signal to RBC divert valve assembly 1120 so as to direct the flow of RBCs removed from blood processing vessel 352a into RBC collection reservoir In an RBC only collection, plasma divert valve assembly 1110 remains in a position to direct flow into reservoir 150 for return of the separated plasma to donor/patient 4 during blood return/replacement fluid delivery submodes. Upon and/or simultaneously with initiation of RBC collection, replacement fluid valve assembly 1100 also preferably is switched to provide replacement fluid flow also into the reservoir 150. In all RBC collection and/or replacement fluid operational phases, it is preferable that, during blood component return/replacement fluid delivery submodes of the RBC collection phase, blood collection and separation device 6 provides appropriate control signals so as to stop the operation of all pump assemblies other than return/delivery pump assembly 1090. In this regard, stoppage of inlet pump assembly 1030 avoids recirculation of uncollected blood components and/or replacement fluid(s) into vessel 352a and resultant dilution of separated RBC components within vessel 352a.

As will be appreciated, and as was also true in the previously described above, in the present invention separated RBCs are not pumped post-separation out of vessel 352a through line 64 for collection, but instead are moved out of vessel 352a and through extracorporeal tubing circuit 10a by the relative pressure of the blood inlet flow to vessel 352a (as this may be modified by the plasma outlet pressure through the plasma outlet port 456). Consequently, trauma to the separated and collected RBCs is minimized.

During the RBC and/or plasma collection phases, the inlet flow into vessel 352a is limited as described above by the above-noted maximum acceptable ACIR to the donor/patient 4. The desired inlet flow rate is also limited by that necessary to maintain the desired packing factor, as also discussed. In this regard, it will be appreciated that, relative to the setup phase, the inlet flow rate may be adjusted slightly upwards during the RBC and/or plasma collection phases since not all anticoagulant is being returned to the donor/patient 4. That is, a portion of the anticoagulant remains with the collected plasma and/or the plasma that is collected with the RBCs in RBC reservoir(s) 954.

Following collection of the desired quantity of red blood cells and or plasma, and after blood separation device 6 has provided control signals to divert assemblies 1110 and so as to divert the respective separated plasma and separated RBC flows to reservoir 150, if further blood processing is not desired, rinseback procedures may then be completed as generally described above. However, here (in the embodiment of FIGS. 2c–2d) where there is no platelet pump splitting the rinseback flow, the plasma pump 1060 is set at the full plasma rate equal to rate of the return/delivery pump 1090 for rinseback. Note again, that the replacement fluid inlet pump 1040 is stopped here also as in all (non-bolus) instances when no RBCs or plasma are being collected.

Additionally, at the end of the procedures, the plasma bag(s) 94 and the red blood cell reservoir(s) 954 may be disconnected from the extracorporeal tubing circuit 10 in fashions like those described above. Storage solutions may also be added, also as described above. Post-collection filtration may also be performed. For example, leukoreduction/white blood cell filtration from the collected RBCs in a fashion as described above, before or after the option of adding a storage solution. The storage solutions and/or filtration devices and corresponding final storage reservoir(s) (not shown) may, as described hereinabove, be preconnected to the collection reservoirs herein, or attached subsequently via sterile connection or spike and sterile barrier connections, also as described hereinabove.

Note, a further beneficial feature of the present invention is that it is preferred that the system 2 be able to monitor or model the hematocrit (and/or platelet count) and the total blood volume of the donor/patient 4 during the overall procedure. For example, the machine 6 can continuously and instantaneously monitor the quantity of RBCs collected, the plasma collected, the anticoagulant (AC) collected with either or both the RBCs and/or plasma as well as the AC delivered to the donor/patient 4, and, if used, the saline/replacement solution delivered to the donor/patient 4 to determine the instantaneous hematocrit (and/or platelet count and/or the total blood volume) of the donor/patient 4. If for example, a donor started with a 45 hematocrit and a total blood volume of 5 liters (roughly equivalent to about 2.25 liters of RBCs), and the equivalent of 0.5 liters of whole blood were removed, and say a 0.5 liters of replacement fluid were added, then a result would be 2.02 liters of RBCs with a total blood volume of 5 liters and a resulting hematocrit of 40. Most desirably, this drop of hematocrit during a procedure may be instantaneously modeled so that the target hematocrit of the resulting products can continue to met. This may mean adjustments to certain flow rates such as the plasma pump rate to ensure that the target amount of separated plasma reaches and exits with the RBCs through the RBC exit port to provide the target hematocrit. Double red blood cell products and/or replacement fluid options will have greater impact on and/or be more greatly impacted by the instantaneous hematocrit of the donor/patient. Thus, this modeling provides better insurance that the target hematocrit will be reached even in a double red blood cell product.

Note further that instantaneous platelet and/or total blood volume monitoring may also be performed in similar fashions, and can also be used to ensure the quality of the platelet and/or plasma products by feed back adjustment control over certain flow rates. Moreover, these and similar procedures may be used to mode for ending or post hematocrit, platelet count and/or total blood volumes as protection measures for the donor/patient. For example, an ending total blood volume (or instantaneous such volume) may be pre-set as a maximum removal from the body in total (or at any time during the procedure); then, the machine 6 will be pre-disposed to disallow the start of any procedures (or stop a progressing procedure) which would ever remove in total (or at anytime during a procedure) any amount more than this pre-set maximum. An example maximum might be 15% of the donor's starting total volume (calculated preferably using height and weight). A user could choose other percentage options as well, as for example a more conservative 13%, inter alia. Similarly, post hematocrit and platelet post-count limits may also be pre-set (or configurable per each donor). Examples might be 30 or 32 post hematocrits, and/or 50,000 or 100,000 platelet post-counts. Maximum procedure times might also be used in such donor safety areas; e.g., 120 or 150 minute maximum procedure times.

As above, several advantages can be realized utilizing these procedures for red blood cell and/or plasma collections. Such advantages include: consistency in final RBC product volume and hematocrit; reduced exposure of a recipient if multiple units of blood products are collected from a single donor/patient and transfused to a single recipient; reduced time requirements for RBC and/or plasma collections and for collection of double units of red blood cells if desired.

Various approaches for plasma and RBC collection have been described above, and other approaches may also be beneficial. By way of an example, the described RBC collection procedure may be carried out following blood priming, but prior to plasma collection. Such an approach may advantageously allow RBC collection to occur in the course of AC ramping, thereby perhaps reducing total processing time requirements. That is, since AC ramping up to a predetermined level (e.g., increasing the AC ratio up to about 13), may be gradually completed prior to the start of a plasma collection procedure (e.g., so as to maintain an acceptable ACIR), completing RBC collection procedures in the course of AC ramping may reduce the overall processing time for both RBC and plasma collection. The RBC collection procedure could be completed when AC ramping reaches about 8.14 (in the U.S.) or 11 (in other countries), with AC ramping continuing thereafter. Alternatively, RBC collection could occur in tandem with AC ramping, wherein the target AC ratio of about 8.14 or 11 would be established as an average effective ratio for the RBCs and plasma collected and mixed within reservoir(s) 954.

Further alternative procedures are available, for example in therapeutic exchanges of RBCs or plasma, such that the exchange RBCs or plasma is the replacement fluid to be delivered through the replacement fluid tubing assembly 960 to the donor/patient 4 while the corresponding RBCs or plasma is removed from the donor/patient as described hereinabove. Collected components may similarly be therapeutically treated upon collection and then returned to the patient through the replacement fluid tubing assembly 960.

Alternative Collections

As mentioned, the present invention provides for the selection of various alternative component products to be collected. At least two discrete tubing and processing vessel sets have been described to achieve these options. The primary advantage is that any of these and other options may be obtained on the same platform or system. For example, extracorporeal blood processing system 2 (see generally FIG. 1) may be used to separate blood in various components and provide for the selection of collections of platelets (single, double or triple products, e.g.), alone or in combination with other products such as RBCs (single or double) and/or plasma (various quantities). More directly, given a particular donor ability (through blood volume, hematocrit and platelet count, e.g.), an operator of the present system may be presented with various options of donation combinations. Then, the operator may choose the most desirable option, and load the appropriate tubing set (see e.g., FIGS. 2A–2B vs. 2C–2D) on the machine 6, and then collect the desired component products. The system 2/machine 6 would operate the appropriate protocols as described hereinabove.

Note, other options are foreseeable as well. For example, though not explicitly shown above (not as preferred), platelets could be collected on a tubing set having a replacement fluid option such as that described relative to FIGS. 2C–2D. However, the vessel would be like vessel 325 (FIGS. 2A–2B, with the platelet outlet line running to and through the plasma pump 1060, e.g.) and the protocol preferably as described for the RBC/platelet option above (preferably platelet collection first, with RBCs to follow). Or, such a platelet/RBC with replacement fluids option could be formed of the tubing set of FIGS. 2A–2B with the replacement fluids run through the plasma pump 1060 with no plasma collection reservoirs then available. The limiting factor in the shown system is a further pump. In other words, if a further pump were added (not shown) to the machine 6, then a platelet/plasma/RBC tubing set such as that shown in FIGS. 2A–2B could be used with an additional pump and tubing line set running to and through the added pump to flow to the reservoir 150. A further limiting factor is that during platelet collections, replacement fluids are generally not necessary. Larger collections, such as double red blood cell products more often indicate a desirability for replacement fluids. Along this line, a further red blood cell container could be added to the tubing set of FIGS. 2A–2B; however, again, the preference would be to have a replacement fluid option available (though not necessary in all cases) for double red blood cell collections.

In either case, substantially all practical options are presently available using the two tubing sets shown and described herein. Moreover, other sets are also available, as for example a platelet/plasma set such as is shown and described in U.S. Pat. No. 5,653,887 to Wahl et al.; inter alia (assigned to the assignee of the present document). Such sets (as described therein) may also be used with the system of the present invention, and provide a further option to the users hereof.

Graphical Computer Interface

In order to assist an operator in performing the various steps of the protocol being used in an apheresis procedure with the apheresis system 2, the apheresis system 2 further includes a computer graphical interface 660 illustrated in FIG. 1. The following descripdescribes an interface for use by an English language speaking operator. For other operations and/or languages, the textual portions of the interface would, of course, be adapted accordingly. The graphical interface 660 includes a computer display 664 which has "touch screen" capabilities. Other appropriate input devices (e.g., keyboard) may also be utilized alone or in combination the touch screen. For example, a pump pause and a centrifuge stop button of the well known membrane type may be provided. The graphics interface 660 not only allows the operator to provide the necessary input to the apheresis system 2 such that the parameters associated with operation of the apheresis system may be determined (e.g., data entry to allow determination of various control parameters associated with the operation of the apheresis system 2), but the interface 660 also assists the operator by providing pictorials of at least certain steps of the apheresis procedure. Moreover, the interface 660 also effectively conveys the status of the apheresis procedure to the operator. Furthermore, the interface 660 also may be used to activate standardized corrective actions (i.e., such that the operator need only identify the problem and indicate the same to the interface 660 which will then direct the apheresis system 2 to correct the same).

Figure 26:
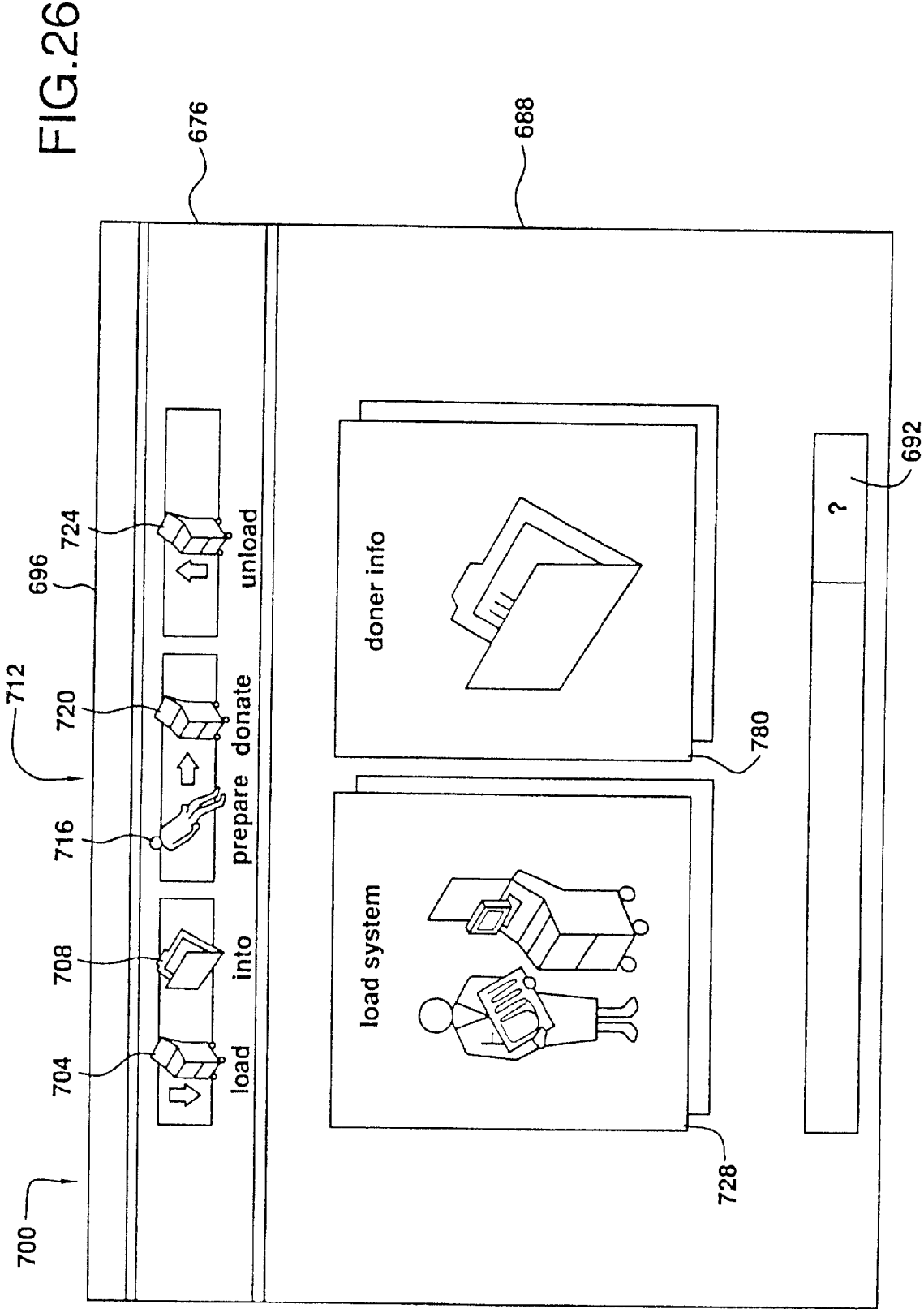
FIG. 26 is a "master screen" for the computer graphics interface of the apheresis system of FIG. 1.

Referring to FIG. 26, at the start of an apheresis procedure a master screen 696 is displayed to the operator on the display 664. The master screen 696, as well as each of the screens displayed to the operator by the interface 600, includes a status bar 676. The status bar 676 includes a system prep icon set 700. The system prep icon set 700 includes a load icon 704 (representing the shape of blood component separation device 6) with a downwardly extending arrow which collectively pictorially conveys to the operator that the disposable set 8 must be loaded onto the blood component separation device 6. The word "LOAD" is also positioned below the load icon 704 to provide a short textual instruction to the operator of the required action(s).

The system prep icon set 700 also includes an information icon 708 (representing the shape of an open filing folder) which pictorially conveys to the operator that certain information relating to the donor/patient 4, the procedure protocol, and/or the blood component separation device 6 must be obtained and entered. This information may be utilized by the apheresis system 2 to calculate one or more of the parameters associated with the apheresis procedure (e.g., inlet flow rate to the blood processing vessel 352) and/or to generate predicted yields of one or more blood component types (e.g., the amount of a certain blood component type which is anticipated to be collected based upon certain parameters such as donation time). The word "INFO" is also positioned below the information icon 708 to provide a short textual instruction to the operator of the required action(s). The information icon 708 is also positioned to the right of the load icon 704 to indicate to the operator that it is preferred, although not required, to perform the step(s) associated with the information icon 708 after the step(s) associated with the load icon 704 have been completed.

The status bar 676 also includes a collection icon set 712. The collection icon set 712 includes a donor/patient prep icon 716 (representing the shape of the donor/patient 4) which pictorially conveys to the operator that the donor/patient 4 must now be fluidly interconnected with the blood component separation device 6. The word "PRE-PARE" is also positioned below the donor/patient prep icon 716 to provide a short textual instruction to the operator of the required action(s). The donor/patient prep icon 716 is also positioned to the right of the information icon 708 to indicate to the operator that the step(s) associated with the donor/patient prep icon 716 may only be performed after the step(s) associated with the load icon 704 and the information icon 708 have been completed.

The collection icon set 712 also includes a donate icon 720 with a laterally extending arrow which collectively pictorially conveys to the operator that the actual collection procedure may be initiated and that the step(s) to initiate this action should now be performed. The word "DONATE" is also positioned below the donate icon 720 to provide a short textual instruction to the operator of the required action(s). The donate prep icon 720 is also positioned to the right of the donor/patient prep icon 716 to indicate to the operator that the step(s) associated with the donate icon 720 must be performed after the step(s) associated with the donor/patient prep icon 716 have been completed.

The status bar 676 also includes an unload icon 724 (representing the shape of the blood component separation device 6) and a generally upwardly extending arrow which collectively pictorially convey to the operator that the disposable set must now be removed from the blood component separation device 6. The word "UNLOAD" is also positioned below the unload icon 724 to provide a short textual instruction to the operator of the required action(s). The unload icon 724 is also positioned to the right of the donate icon 720 to indicate to the operator that the step(s) associated with the unload icon 724 must be performed after the step(s) associated with the donate icon 720 have been completed.

The system preparation icon set 700, collection icon set 712, and unload icon 724 in the status bar 676 sequentially set forth certain basic steps for the apheresis procedure. That is, the left to right positioning of the various icons conveys to the operator the desired/required order in which the step(s) associated with the icons should/must be performed. Moreover, the individual icons 704, 708, 716, 720, and 724 are also utilized to convey the status of the apheresis procedure to the operator via three-way color differentiation (i.e., one status per color) and/or by three-way shade differentiation. "Shades" includes variations of a given color and also encompasses using variations based upon being "lighter" and/or "darker" (e.g., using light gray, medium gray, and dark gray). That is, a "gray-scale" technique may also be utilized and is encompassed by use of color and/or shade differentiation.

The first status conveyed to the operator by the icons in the status bar 676 is that the step(s) associated with respective icon are not ready to be performed. That is, the performance of this step(s) would be premature. This first status is conveyed to the operator by displaying the associated icon in a first color, such as white. The corresponding textual description may also be presented in this first color as well. As noted, a first "shade" may also be utilized to convey this first status as well.

The second status conveyed to the operator by the icons in the status bar 676 is that the step(s) associated with the respective icon is either ready for execution or is in fact currently being executed. That is, an indication is provided to the operator that performance of this step(s) of the apheresis procedure is now timely. This second status is conveyed to the operator by displaying the associated icon in a second color, such as yellow. The corresponding textual description may also be presented in this second color as well. As noted, second "shade" may also be utilized to convey this second status as well.

The third status conveyed to the operator by the icons in the status bar 676 is that the step(s) associated with the respective icon has been executed. That is, an indication is provided to the operator that performance of this step(s) of the apheresis procedure has been completed.

This third status is conveyed to the operator by displaying the associated icon in a third color, such as gray. The corresponding textual description may also be presented in this third color as well. As noted, third "shade" may also be utilized to convey this third status as well.

Based upon the foregoing, it will be appreciated that significant information is conveyed to the operator by merely viewing the status bar 676. For instance, the operator is provided with a pictorial graphic indicative of the fundamental steps of an apheresis procedure. Moreover, the operator is provided with a textual graphic indicative of the fundamental steps of an apheresis procedure. Furthermore, the operator is provided with a desired/required order in which these steps should/must be performed. Finally, the operator is provided with the status of the apheresis procedure via the noted three-way color/shade differentiation.

The master screen 696, as well all other screens displayed to the operator by the interface 660 during an apheresis procedure, also include a work area 688. The work area 688 provides multiple functions. Initially, the work area 688 displays additional information (pictorially and textually in some instances) on performing the apheresis procedure to the operator (e.g., certain additional substeps of the apheresis procedure, addressing certain "conditions" encountered during the apheresis procedure). Moreover, the work area 688 also displays additional information on the status of the apheresis procedure to the operator. Furthermore, the work area 688 also provides for operator interaction with the computer interface 660, such as by allowing/requiring the operator to input certain information.

Continuing to refer to FIG. 26, the work area 688 of the master screen 696 displays a load system button 728 and a donor/patient info button 780. The operator may touch either of these buttons 728, 780 (i.e., since the display 696 has "touch screen" capabilities) to generate further screens for providing information to the operator and/or to facilitate the inputting of information to the computer interface 660. The operator may initially touch either the load system button 728 or the donor/patient info button 780 at the start of an apheresis procedure. That is, the order in which the step(s) associated with the load system button 728 are performed in relation to the apheresis step(s) associated with the donor/ patient info button 780 are performed is not generally important (i.e., the steps associated with the load system button 728 may be performed before or after the steps associated with the donor/patient info button 780). The apheresis procedure will be described with regard to the operator electing to initially activate the load system button 728 via the touch screen feature.

However, as described below, it has become more preferable to perform the donor/patient information step(s) before loading the disposable assembly because alternative disposable assemblies are now available (see e.g., the alternative forms of cassette and vessel assemblies in FIGS. 2A, 2B relative to those of FIGS. 2C, 2D). Thus, by performing the donor information step (FIGS. 32–46, below) first, a selection of which cassette and/or vessel assembly (e.g., vessel 325 or 325*a* of respective FIGS. 2A, 2B or 2C, 2D) might be preferred for a given donor. This option will be described further below.

Figure 27:
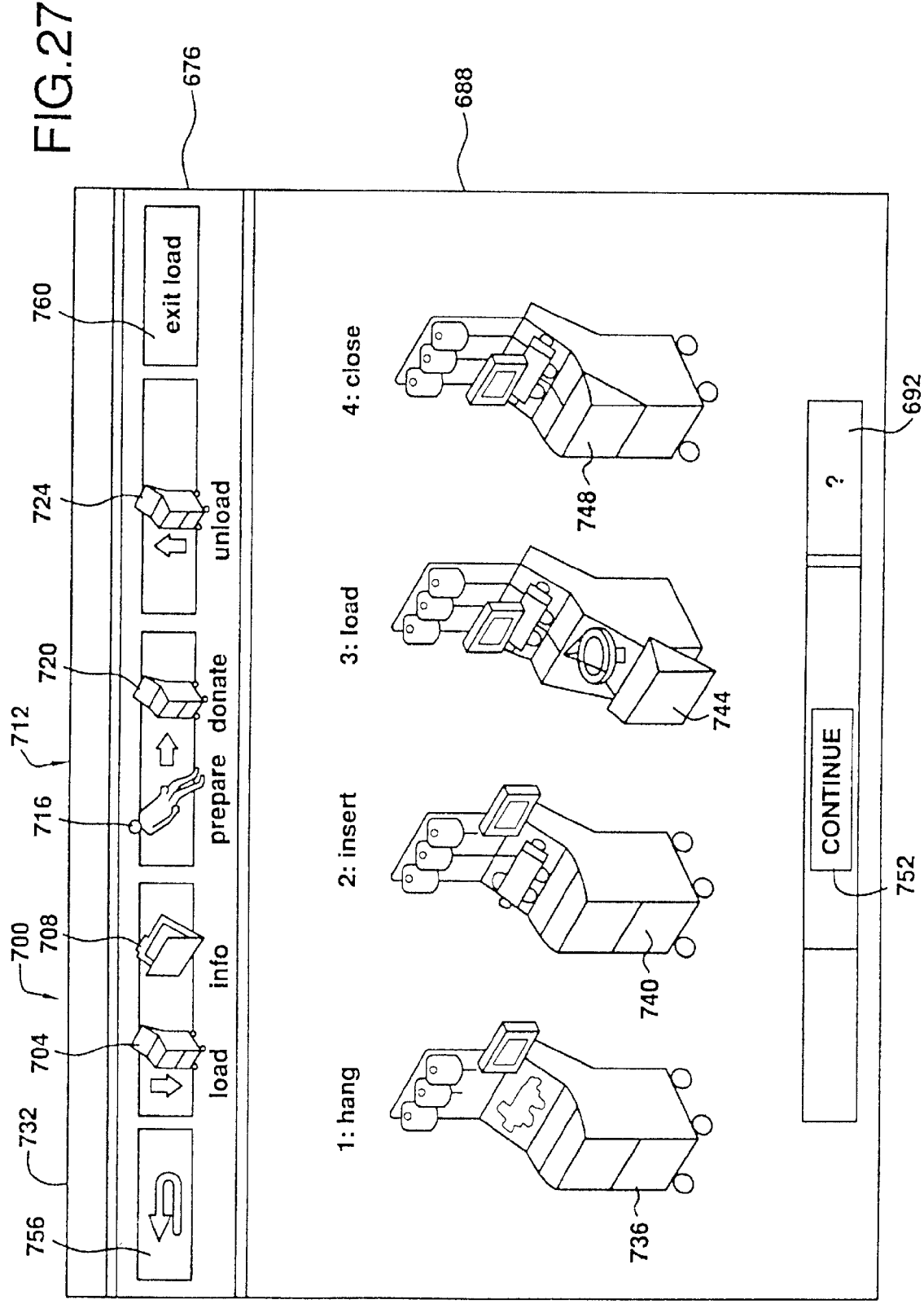
FIG. 27 is a "loading procedures screen" for the computer graphics interface of the apheresis system of FIG. 1.

Whether before or after donor information has been entered (see description of FIGS. 32–46, below), activation of the load system button 728 generates a loading procedure screen 732 on the computer display 664 which is illustrated in FIG. 27. The loading procedure screen 732 displays multiple pictorials to the operator in the work area 688 which relate to the steps which need to be performed to prepare the blood component separation device 6 for an apheresis procedure. Initially, a hang pictorial 736 is displayed which pictorially conveys to the operator that the various bags (e.g., an AC bag(s) (not shown), plasma collect bag(s) 94 platelet collect bag(s) 84) need to be hung on the blood component separation device 6 and generally how this step may be affected by the operator. The word "HANG" is also positioned above the hang pictorial 736 to provide a short textual instruction to the operator of the required action(s). Consequently, there are two different types of graphical representations provided to the operator relating to a specific operator action which is required to prepare the blood component separation device 6 for the apheresis procedure. Moreover, the hang pictorial 736 is disposed on the left side of the loading procedure screen 732 which indicates that this is the first step or substep associated with the load icon 704. In order to provide further indications of the desired order to the operator, the number "1" is also disposed adjacent to the word "HANG."

A focus color (e.g., yellow) or shade may be used to direct the operator's attention to specific areas of the machine or screen. The loading procedure screen 732 also displays an insert pictorial 740 to the operator in the work area 688. The insert pictorial 740 pictorially conveys to the operator that the cassette assembly 110 needs to be mounted on the pump/valve/sensor assembly 1000 of the blood component separation device 6 and generally how this step may be affected by the operator. The word "INSERT" is also positioned above the insert pictorial 740 to provide a short textual instruction to the operator of the required action(s). The insert pictorial 740 is also positioned to the right of the hang pictorial 736 to indicate to the operator that it is preferred, although not required, to perform the step(s) associated with the insert pictorial 740 after the step(s) associated with the hang pictorial 736 have been completed. In order to provide further indications of the desired order to the operator, the number "2" is also disposed adjacent to the word "INSERT." The loading procedure screen 732 also displays a load pictorial 744 to the operator in the work area 688. The load pictorial 744 pictorially conveys to the operator that the blood processing vessel 352 needs to be loaded into the channel 208 of the channel housing 204 on the centrifuge rotor assembly 568 and generally how this step may be affected by the operator. The word "LOAD" is also positioned above the load pictorial 744 to provide a short textual instruction to the operator of the required action(s). The load pictorial 744 is also positioned to the right of the insert pictorial 740 to indicate to the operator that it is preferred, although not required, to perform the step(s) associated with the load pictorial 744 after the step(s) associated with the insert pictorial 740 have been completed. In order to provide further indications of the desired order to the operator, the number "3" is also disposed adjacent to the word "LOAD."

Finally, the loading procedure screen 732 displays a close pictorial 748. The close pictorial 748 pictorially conveys to the operator that the door of the blood component collection device housing the centrifuge rotor assembly 568 needs to be closed and generally how this step may be affected by the operator. The word "CLOSE" is also positioned above the close pictorial 748 to provide a short textual instruction to the operator of the required action(s). The close pictorial 748 is also positioned to the right of the load pictorial 744 to indicate to the operator that it is required to perform the step(s) associated with the close pictorial 748 after the step(s) associated with the load pictorial 744 have been completed. In order to provide further indications of the desired order to the operator, the number "4" is also disposed adjacent to the word "CLOSE."

In summary, the work area 688 of the loading procedure screen 732 not only conveys to the operator what type of steps must be performed for this aspect of the apheresis procedure and generally how to perform these steps, the work area 688 of the loading procedure screen 732 also specifies the order in which these steps should be performed by two "methods." Initially, the pictorial graphics 736, 740, 744 and 748 are sequentially displayed in left-to-right fashion to specify the desired/required order of performance. Moreover, the four steps are also numerically identified next to their associated one-word textual description.

Figure 28:
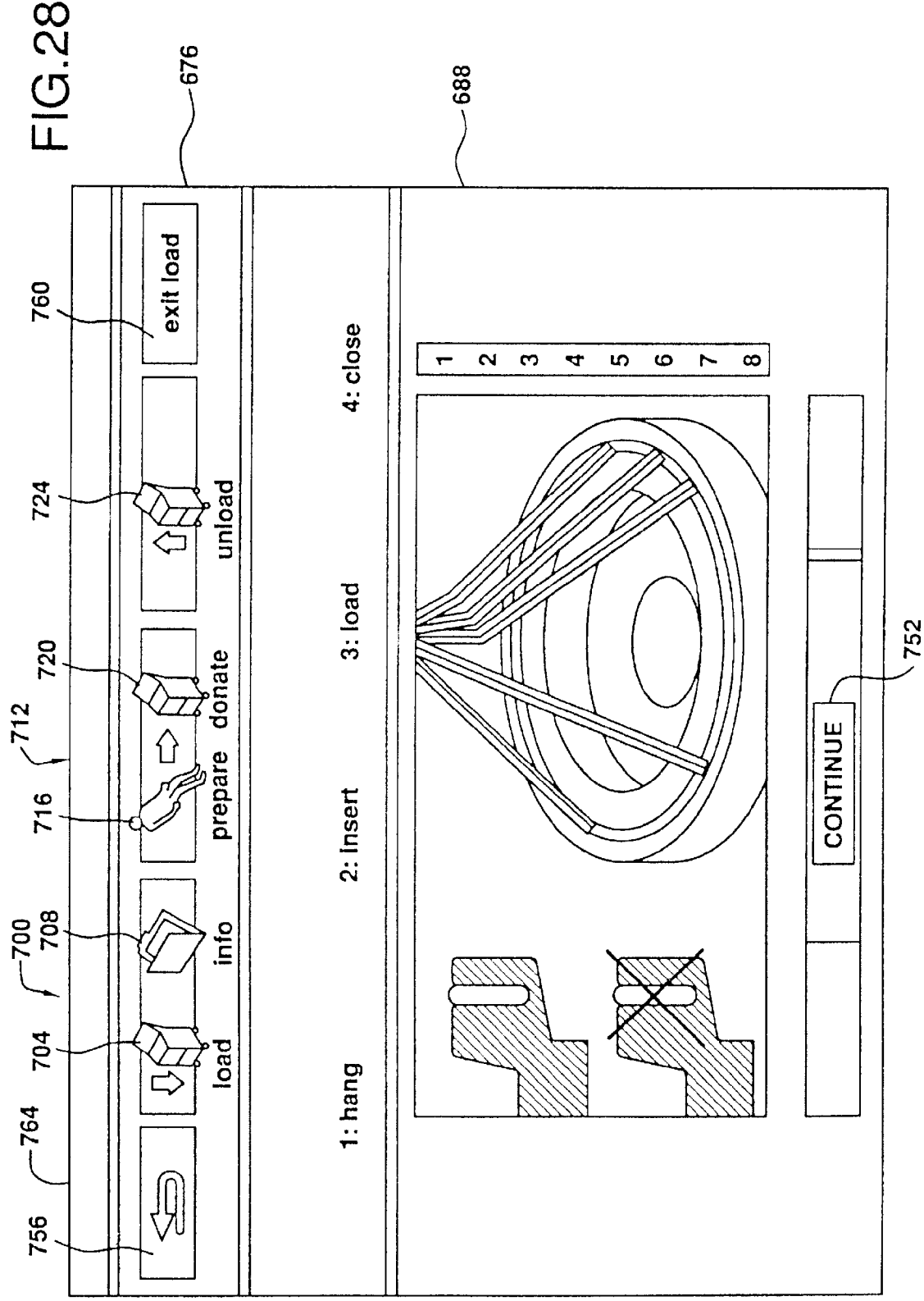
FIG. 28 is one embodiment of a "help screen" for the loading procedures screen of FIG.

In the event that the operator requires additional guidance with regard to any of the steps presented on the loading procedure screen 732, the operator may touch the help button 692 provided on the loading procedure screen 732. This may display a menu of screens which the operator may view and/or may sequentially present a number of help screens associated with the loading procedure screen 732. FIG. 28 illustrates a help screen 764 which relates to the loading of the blood processing vessel 352 into the channel 208 on the channel housing 204. Note that in the case of the help screen 764 the upper portion of the work area 688 of the loading procedure screen 732 is retained (i.e., the one word textual descriptions of the four basic steps and the associated numerical ordering identifier). Moreover, the help screen 764 provides the operator with more detail, in the nature of additional pictorials, regarding one or more aspects of the particular step(s) or substep or in this case on the loading of the blood processing vessel 352 in the channel 208. Once the operator exits the help screen 764 via touching the continue button 752 on the help screen 764, the operator is returned to the loading procedure screen 732 of FIG. 27. Various other screens in the graphics interface 660 may include a help button 692 to provide this type of feature.

When the operator has completed each of the four steps or substeps presented on the loading procedure screen 732, the operator touches the continue button 752 on the bottom of the loading procedure screen 732. In the event that during the time in which the operator is performing the steps or substeps associated with the loading procedure screen 732 the operator wants to return to the begin operations screen 696, the operator may touch the display screen 664 in the area of the return button 756. The return button 756 may be provided on various of the screens to return the operator to the previous screen when acceptable. Moreover, in the event that during the time in which the operator is performing the steps or substeps associated with the loading procedure screen 732 the operator wants to terminate the loading procedure, the operator may touch the display screen 664 in the area of the exit load or cancel button 760. The exit load or cancel button 760 may be provided on various of the other screens to provide the operator with the option to exit the loading procedure where appropriate.

Figure 29:
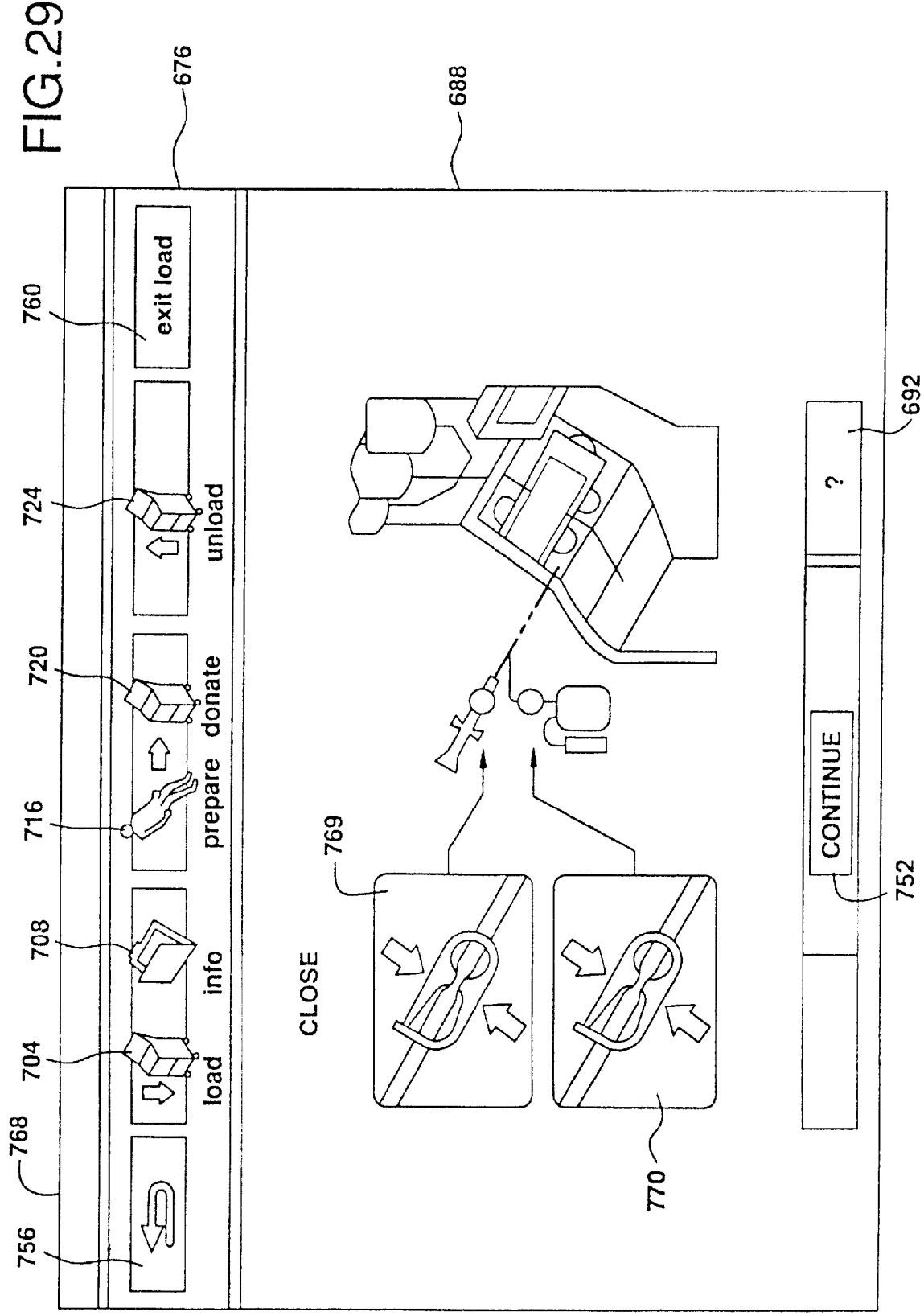
FIG. 29 is a "disposable pressure test screen" for the computer graphics interface of the apheresis system of FIG. 1.
Figure 30:
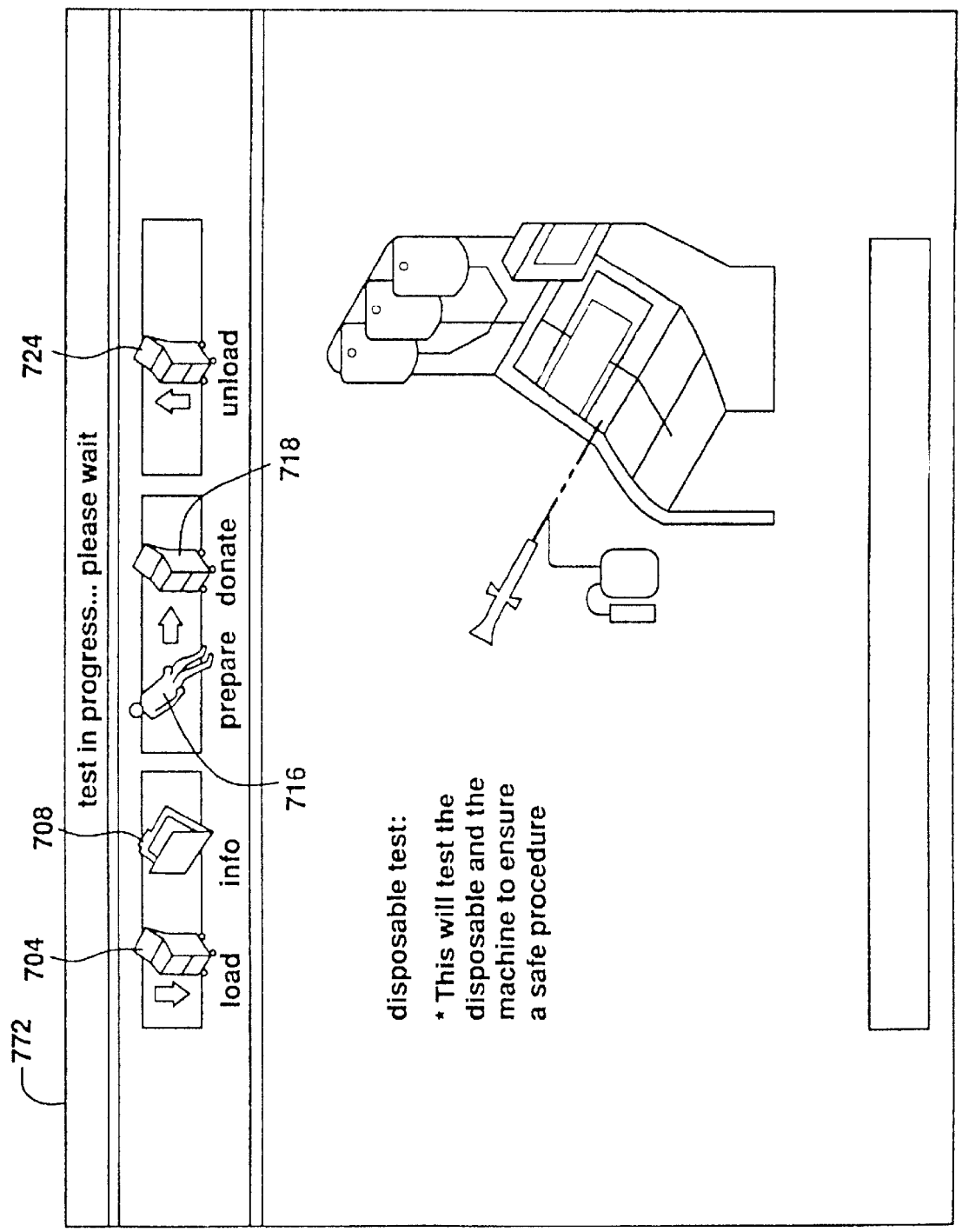
FIG. 30 is a "pressure test in progress screen" for the computer graphics interface of the apheresis system of FIG. 1.

When the operator touches the continue button 752 on the loading procedure screen 732, a disposable pressure test screen 768 is produced on the display 664, one embodiment of which is illustrated in FIG. 29. Generally, the disposable pressure test screen 768 pictorially conveys to the operator that certain steps must be undertaken to allow for pressure testing of the disposable set 8 and how this may be affected by the operator. In this regard, a donor/patient access line clamp pictorial 769 pictorially conveys to the operator that the blood removal/return tubing assembly 20, specifically the interconnect tubing 38, to the donor/patient 4 must be sealed off. A donor/patient sample line clamp pictorial 770 pictorially conveys to the operator that the sample line of the sample subassembly 46 must also be sealed off as well. When the operator has completed these steps, the operator touches the continue button 752 and a test in progress screen 772 is displayed to the operator to pictorially and textually convey to the operator that the testing procedure is underway and such is illustrated in FIG. 30.

Figure 31:
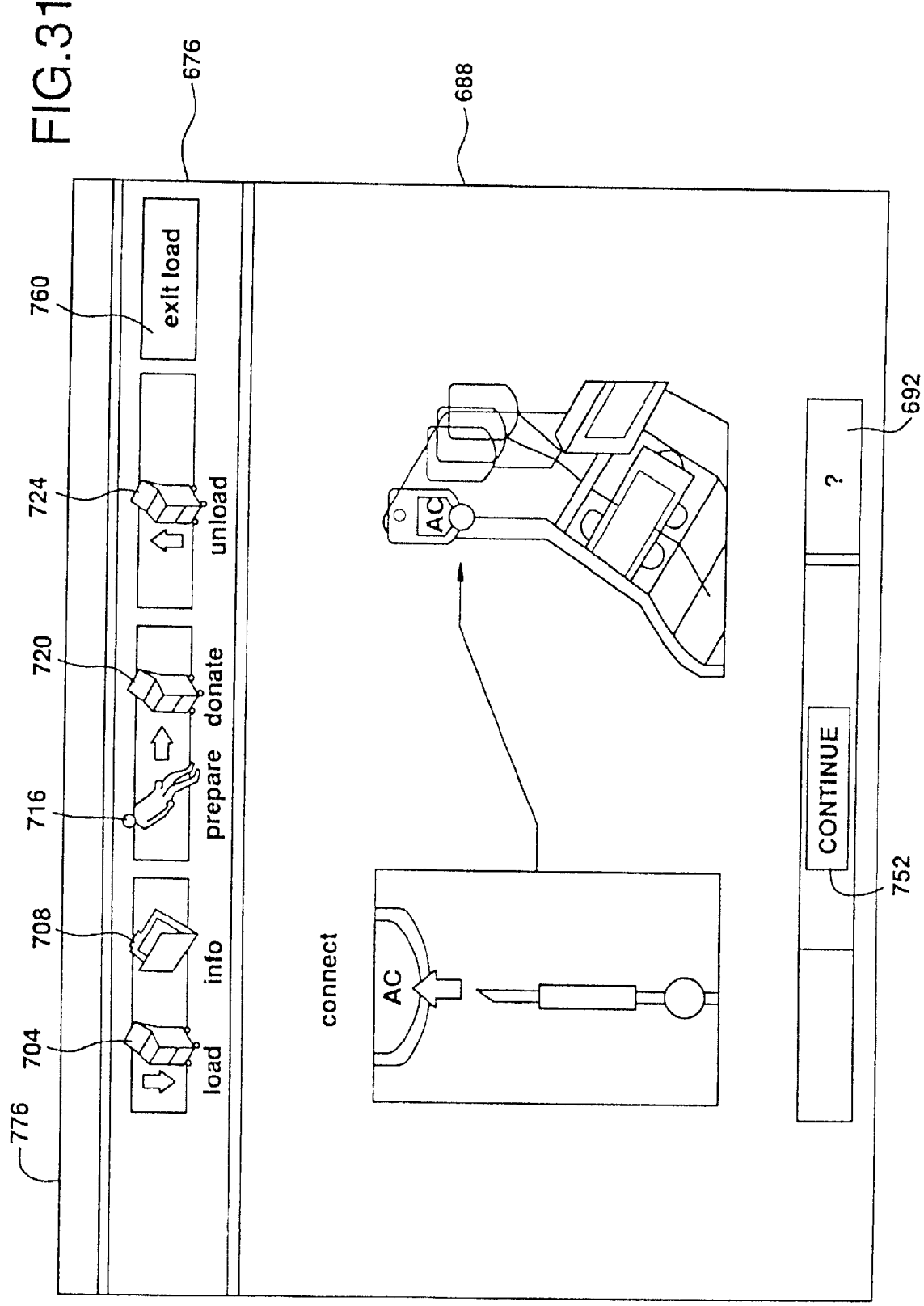
FIG. 31 is a "AC interconnect screen" for the computer graphics interface of the apheresis system of FIG. 1.

After the pressure test of the disposable set 8 is complete, an AC interconnect screen 776 is produced on the display 664 and one embodiment of which is illustrated in FIG. 31. The AC interconnect screen 776 pictorially conveys to the operator that the anticoagulant tubing assembly 50, specifically the spike drip member 52, of the extracorporeal tubing circuit 10 needs to be fluidly interconnected with the AC bag (not shown), as well as generally how this step may be affected by the operator. When this step has been completed by the operator, the operator touches the continue button 752 on the display 664.

Figure 32:
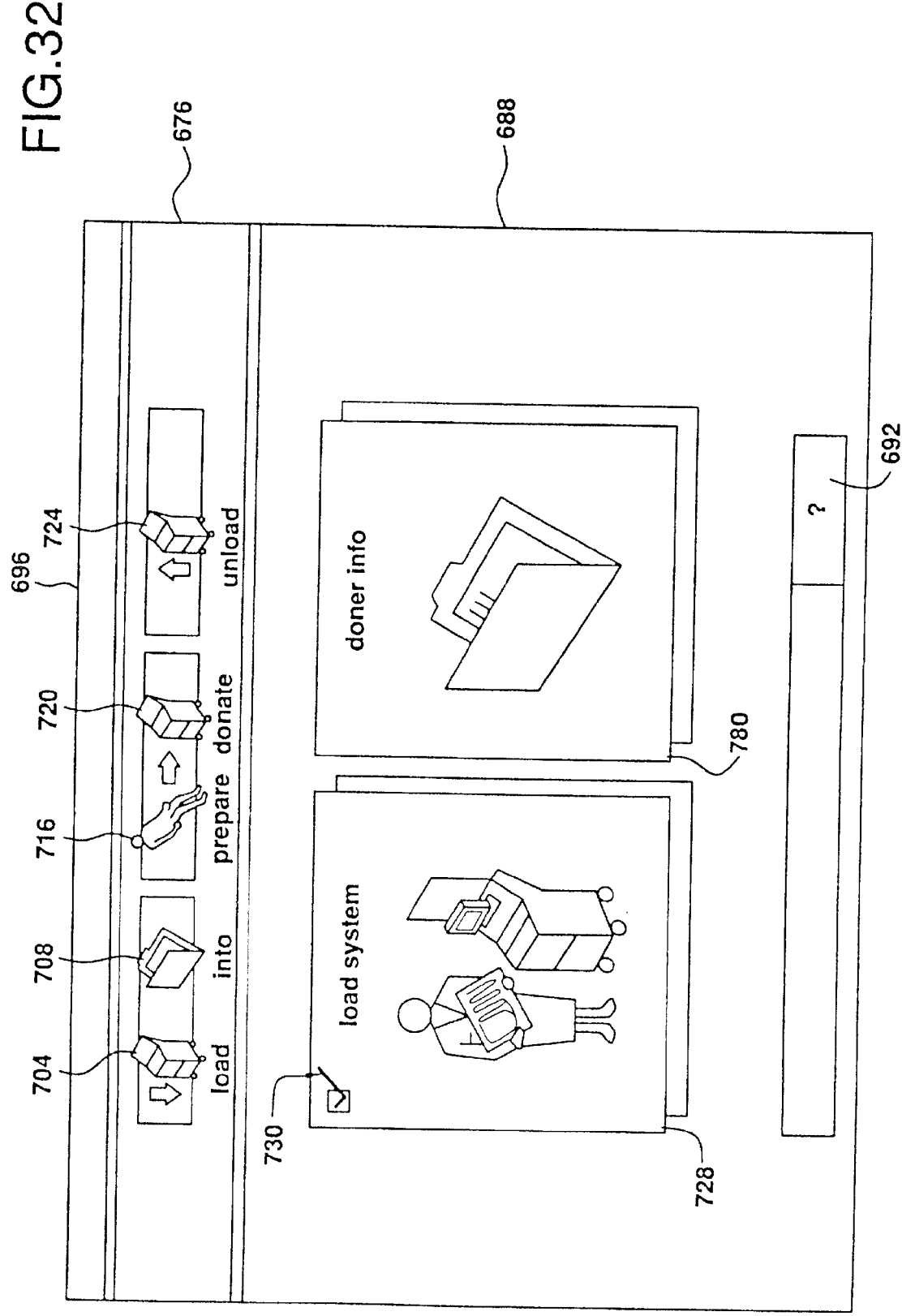
FIG. 32 is the "master screen" of FIG. 26 which has been updated to reflect completion of the loading of the disposables.

The AC interconnect is the last of the steps associated with the load icon 704 such that the operator is returned to the master screen 696. The master screen 696 now reflects the current status of the apheresis procedure and is illustrated in FIG. 32. That is, the color or shade of the load icon 704 is changed from the second color/shade to the third color/shade to that which indicates that all steps associated with the load icon 704 have been completed by the operator. Moreover, a status check 730 appears on the load system button 728 in the work area 688 as well. The load system button 728 is grayed out for the duration of the procedure and thus indicates that the system setup may not be repeated. Consequently, two different types of indications are provided to the operator of the current status regarding the loading procedure. The change in status of the donor/patient data entry portion of the apheresis procedure is also updated by presenting the information icon 708 in the status bar 676 in the second color/shade which indicates to the operator that it is now appropriate to begin this aspect of the apheresis procedure.

Figure 33:
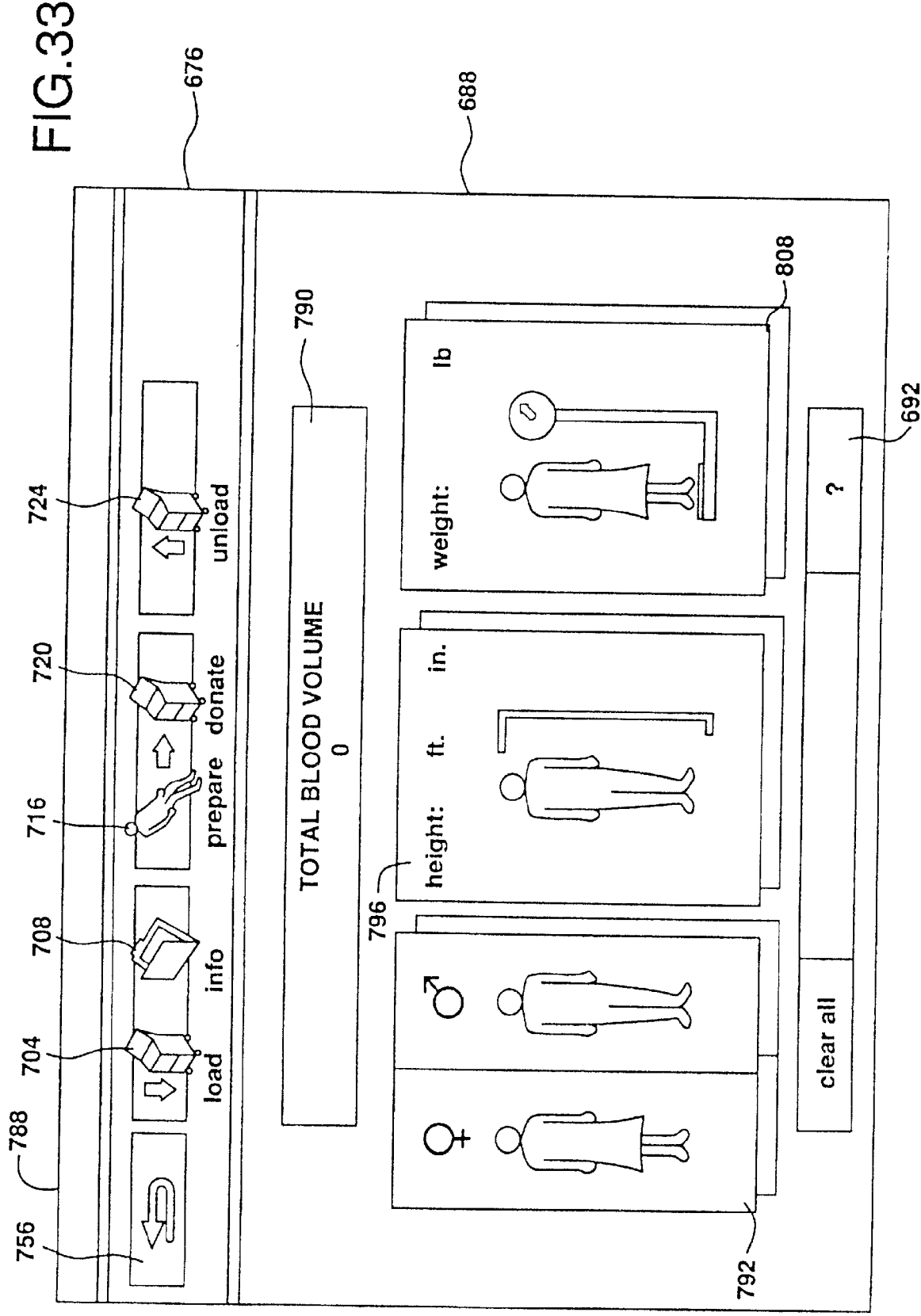
FIG. 33 is a "donor/patient data screen" for the computer graphics interface of the apheresis system of FIG. 1.
Figure 34:
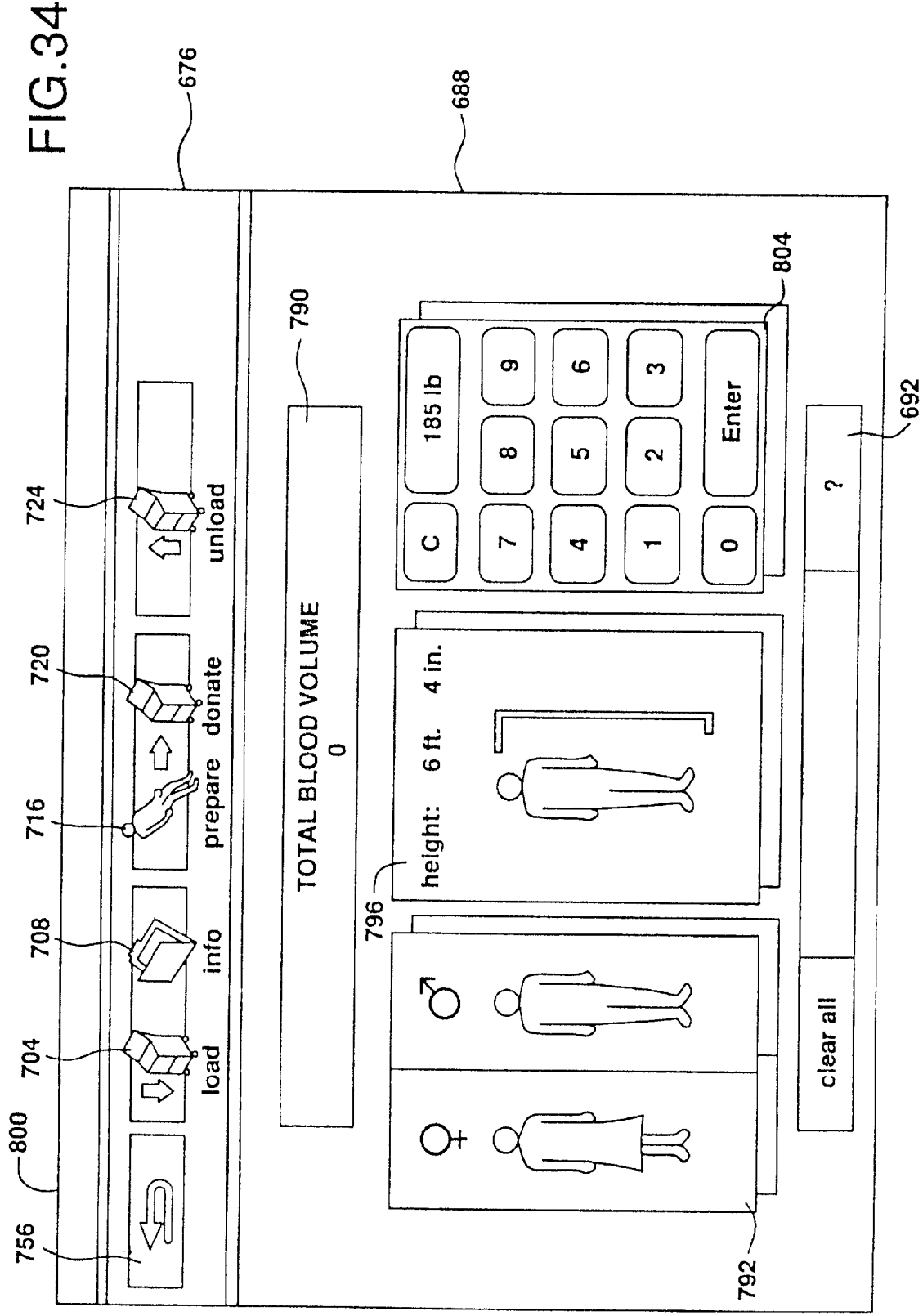
FIG. 34 is a "weight input screen" for the computer graphics interface of the apheresis system of FIG. 1.

Whether after loading the disposable assembly as just described, or prior thereto, as mentioned above as preferred herein, the operator may then enter donor information to assist in determining which products will be the subject of this donation. The operator enters the information entry portion of the apheresis procedure by touching the info button 780 on the display 664 of the master screen 696. This produces a donor/patient data screen 788 on the display 664, one embodiment of which is illustrated in FIG. 33. The donor/patient data screen 788 which includes a sex-type button 792, a height button 796, and a weight button 808. The operator may indicate the sex of the donor/patient 4 by touching the relevant portion of the split sex-type button 792 and the selected sex may be displayed to the operator (e.g., via color differentiation). Moreover, the operator may enter the height and weight of the donor/patient 4 by touching the height button 796 and the weight button 808, respectively. When the height button 796 and weight button 808 are engaged by the operator, a keypad 804 is superimposed over the button whose information is to be entered as illustrated in FIG. 34. The keypad 804 may be used to enter the height and weight of the donor/patient 4 and this information may also be displayed to the operator.

The information entered by the operator on the donor/patient data screen 788 is used to calculate, for instance, the total blood volume of the donor/patient 4 which is presented in a total blood volume display 790 on the donor/patient data screen 788. The total blood volume of the donor/patient 4 may be utilized in the determination of various parameters associated with the apheresis procedure and/or in the estimation of the number and types of blood components which are anticipated to be collected in the procedure. When the operator has completed these data entry procedures, the operator touches the continue button 752 which will be displayed on the bottom of the donor/patient data screen 788 after all requested information has been input.

Figure 35:
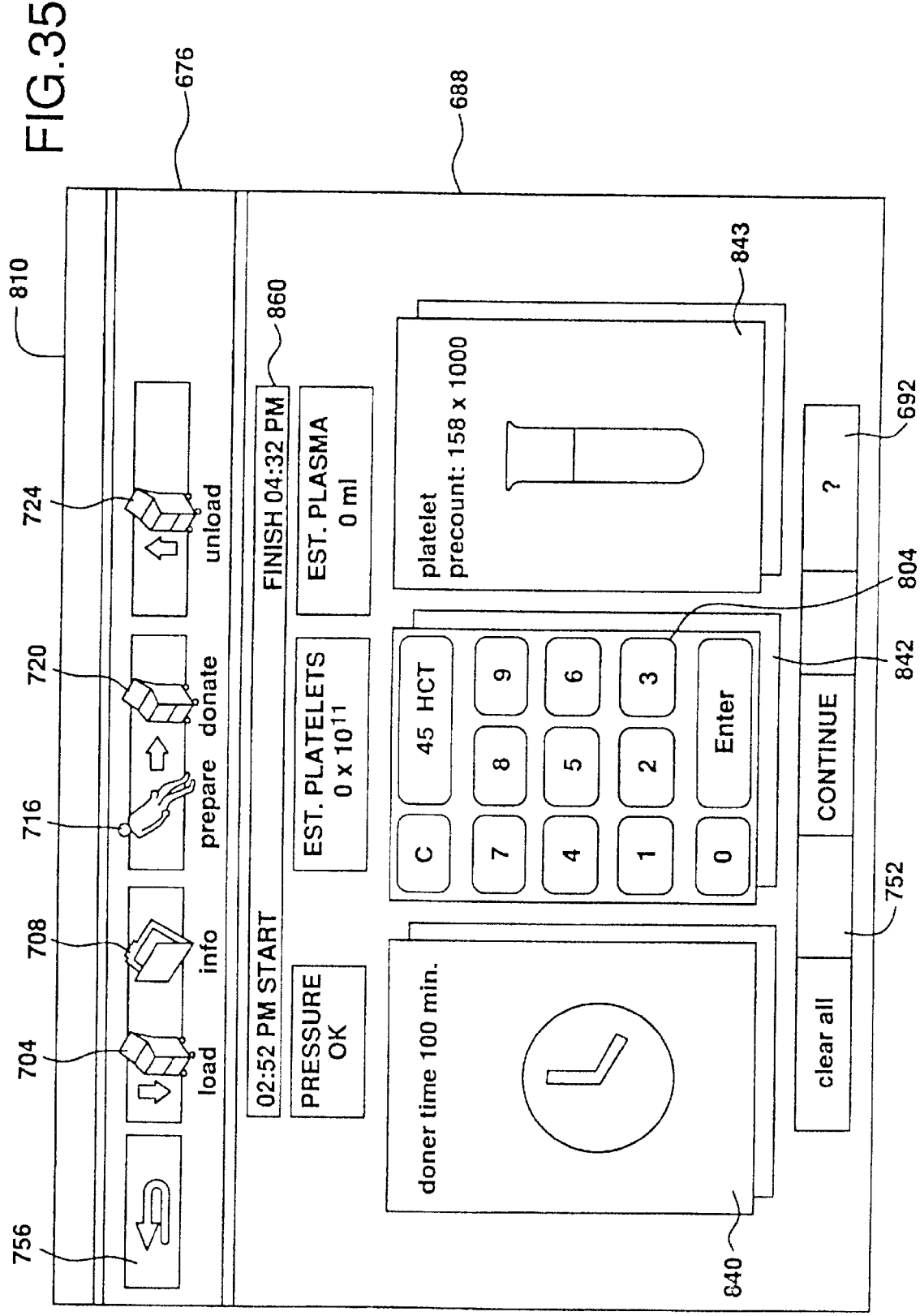
FIG. 35 is a "lab data screen" for the computer graphics interface of the apheresis system of FIG. 1.
Figure 36:
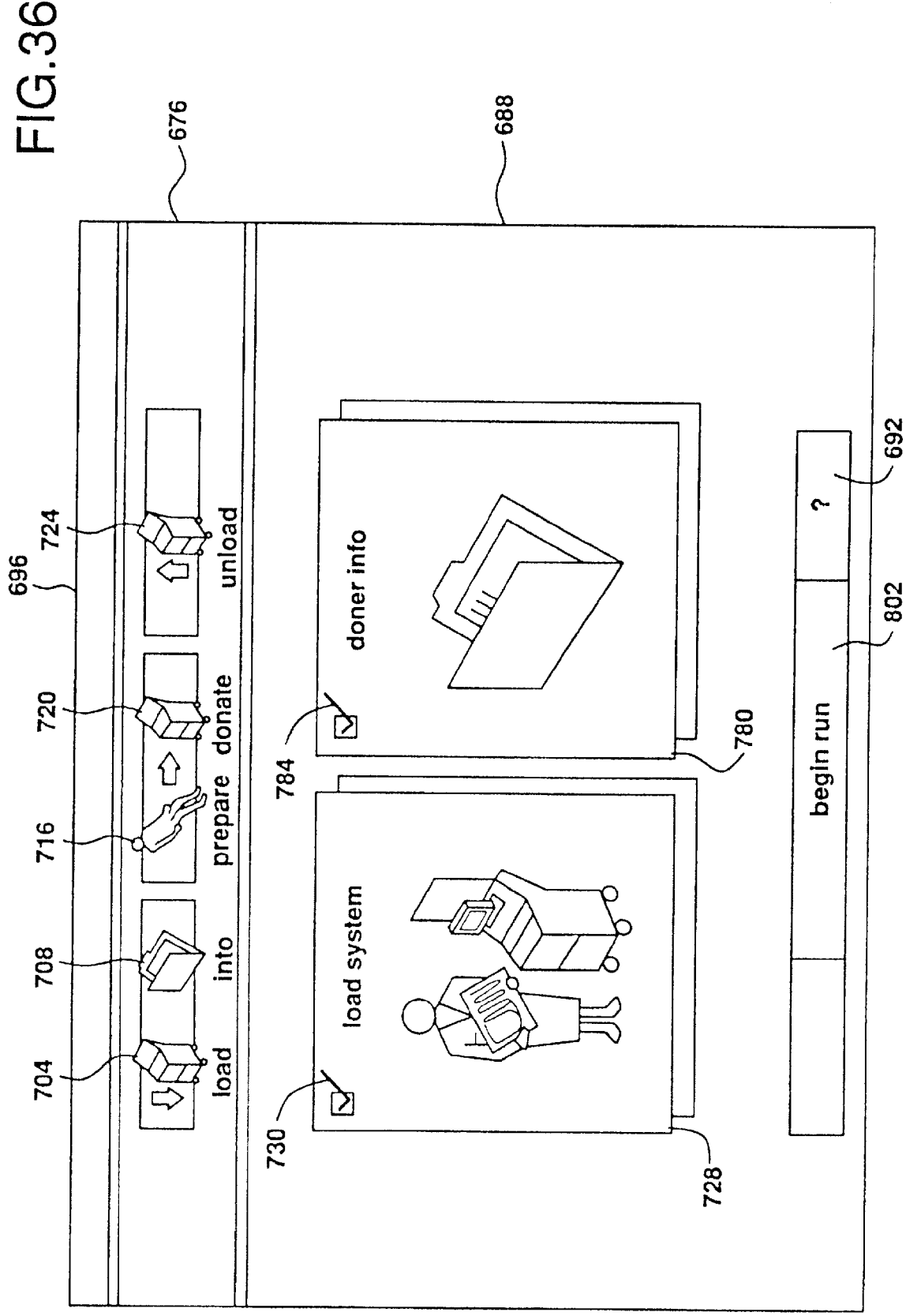
FIG. 36 is the "master screen" of FIG. 26 which as been updated to reflect completion of the donor/patient preps.

A lab data entry screen 810 may also be generated on the computer display 664 after the steps associated with the donor/patient data screen 788 have been completed and as indicated by the operator, one embodiment of which is illustrated in FIG. 35. The lab data entry screen 810 requests the operator to enter the time for the collection procedure by touching a donation time button 840 which results in the keypad 804 being superimposed over the donation time button 832 (not shown). The donation time entered by the operator will be displayed on a time display 860, which specifies the duration for the procedure. Moreover, the donation time entered by the operator may also be displayed on the donation time button 840. The donation time is used, for instance, in the prediction of the number of the blood component(s) (e.g., red blood cells, platelets, and/or plasma) which are anticipated to be collected during the procedure.

The lab data screen 810 also prompts the operator to enter the hematocrit of the donor/patient 4 by touching a hematocrit button 842. This results in the keypad 804 being superimposed over the hematocrit button 842. The operator may then enter the hematocrit of the donor/patient 4 (e.g., as determined via laboratory analysis of a blood sample from the donor/patient 4) and such may be displayed on the hematocrit button 842. The hematocrit of the donor/patient 4 is also utilized by one or more aspects of the apheresis procedure.

The lab data screen 810 also prompts the operator to enter the platelet precount of the donor/patient 4 by touching a platelet precount button 843. This results in the keypad 804 being superimposed over the platelet precount button 843. The operator may then enter the platelet precount of the donor/patient 4 (e.g., as determined via laboratory analysis of a blood sample from the donor/patient 4) and such may be displayed on the platelet precount button 843. The platelet precount of the donor/patient 4 is also utilized by one or more aspects of the apheresis procedure.

Once the operator has entered all of the requested information, the operator touches the continue button 752 which then displays a procedure listing (not shown) depicting which donation procedures this donor is qualified to undergo, and hence which blood component product or products this donor may donate. Preferably, such a listing will present preferred donation options (configurable by the blood center), such as blood center preferences and/or prioritizations for particular products (e.g., platelet products first, RBCs second; or vice versa), including whether double products may be favored. Then, if a particular donor is qualified to give certain products (as determined by the machine 6 based upon the donor information entered as just described), then this listing will so indicate with the preferences also presented. Moreover, other procedures may also be listed with information such as whether such procedures may not be qualified for this particular donor no matter the circumstances, or perhaps certain other procedures may be listed with indications that certain further products might be qualified if certain variable information were changeable (e.g., if more time were allowed for a procedure). Thus, such procedures may then indicate to the operator to return to screen 810 and change the variable information (e.g., allot more time) to then qualify that particular procedure. Also alternatively, certain procedures may be indicated as available if a certain amount of replacement fluid would be used with a tubing set according to the embodiment of FIGS. 2C–2D, for example. Thus, a selection of which tubing set to be used will also be alternatively available at this point in the overall procedure. Then, when all such selections (procedure (including priority and/or variable changes, if any) and tubing set, e.g.) are made, the operator can then continue to the next step; preferably loading the chosen tubing set on the machine 6 in the fashion described above (see description relative to FIGS. 26–41).

Then, a further continue button touch (not shown) may then return the operator to the master screen 696 which now reflects the current status of the apheresis procedure and as illustrated in FIG. Since all of the steps associated with the information icon 708 have now been completed, the color/shade of the information icon 708 is changed from the second color/shade to the third color/shade to convey to the operator that all associated steps have been completed. Moreover, a status check 784 appears on the donor/patient info button 780 in the work area 688 as well. Consequently, two different types of indications are provided to the operator of the current status of this aspect of the apheresis procedure. Moreover, the change in status of the collection icon set 712 of the apheresis procedure is updated by changing the color/shade of the donor/patient prep icon 716 in the status bar 676 from the first color/shade to the second color/shade. A run button 802 is also now presented on the master screen 696 such that the steps associated with the collection icon set 712 may now be undertaken and further such that pictorial representations of the same may be provided to the operator.

Figure 37:
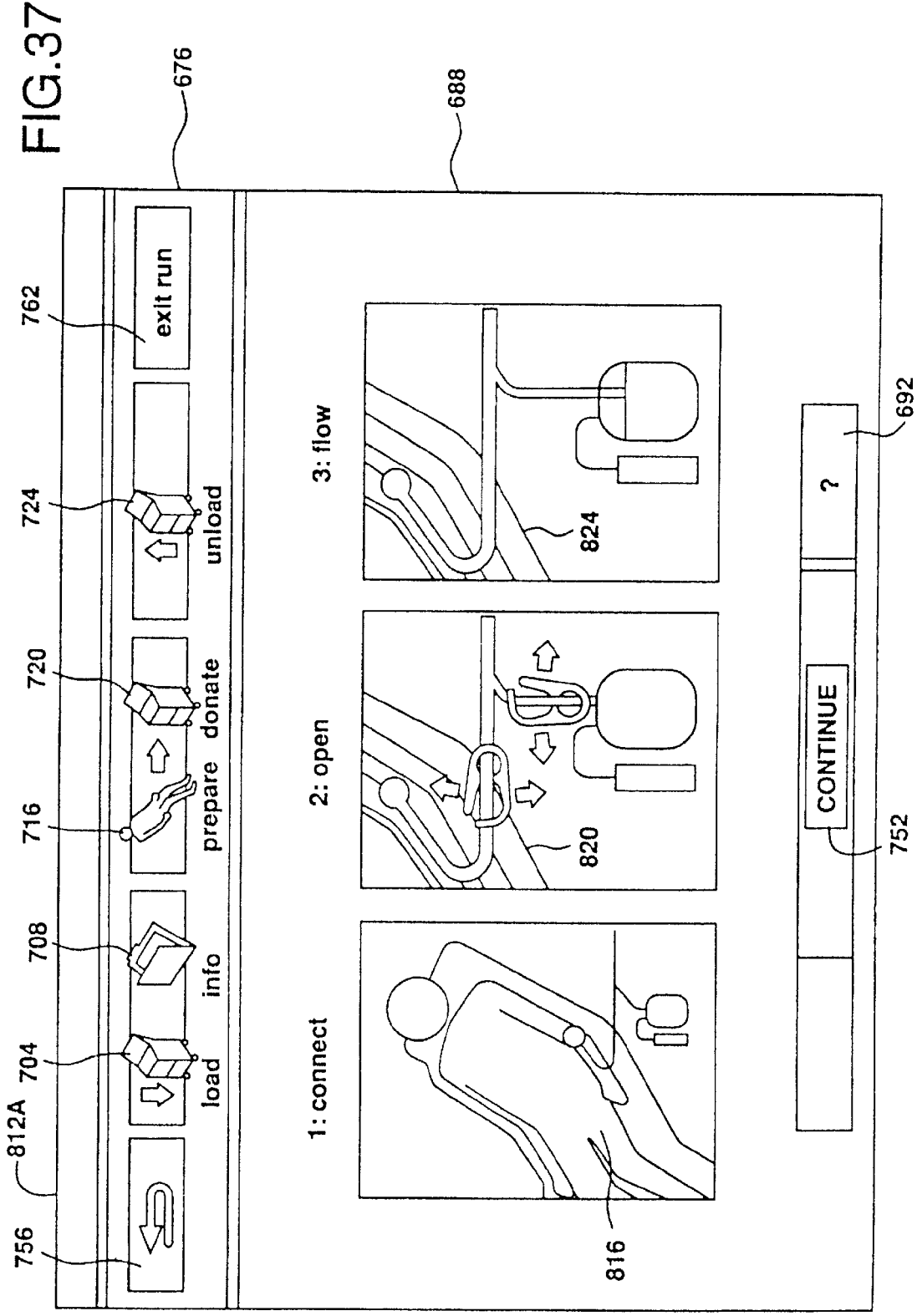
FIG. 37 is a first "donor/patient preps screen" for the computer graphics interface of the apheresis system of FIG. 1.

The initial screen for steps associated with the collection icon set 712 is a donor/patient prep screen 812A which is illustrated in FIG. 37. The donor/patient prep screen 812A pictorially conveys to the operator the steps which must be undertaken in relation to the donor/patient 4 being fluidly interconnected with the blood component separation device. Initially, a donor/patient connect pictorial 816 is displayed which pictorially conveys to the operator that an access needle 32 must be installed on the donor/patient 4, as well as generally how this step may be affected by the operator. The word "CONNECT" is also positioned above the donor/ patient connect pictorial 816 to provide a short textual instruction to the operator of the required action(s). The donor/patient connect pictorial 816 is disposed on the left side of the donor/patient prep screen 812A which indicates that this is the first step or substep associated with the donor/patient prep icon 716. In order to provide further indications of the desired order to the operator, the number "1" is also disposed adjacent the word "CONNECT."

The donor/patient prep screen 812A also displays an open pictorial 820 on the display 664. The open pictorial 820 pictorially conveys to the operator that the clamps 42 in the interconnect tubing 38 and the clamp in the tubing of the sample subassembly 46 must be removed, as well as generally how these steps may be affected by the operator. The word "OPEN" is also positioned above the open flow pictorial 820 to provide a short textual instruction to the operator of the required action(s). The open pictorial 820 is disposed to the right of the donor/patient connect pictorial 816 which indicates that the step(s) associated with the open pictorial 820 should be performed only after the step(s) associated with the donor/patient connect pictorial 816 have been completed. In order to provide further indications of the desired order to the operator, the number "2" is also disposed adjacent the word "OPEN."

The donor/patient prep screen 812A also displays a flow pictorial 824 on the display 664. The flow pictorial 824 pictorially conveys to the operator that there should now be a flow of blood from the donor/patient 4 into the blood removal/return tubing assembly 20, specifically the blood removal tubing 22, and in the sample tubing of the sample subassembly 46. The word "FLOW" is also positioned above the flow pictorial 824 to provide a short textual description to the operator of what should be occurring at this time. The flow pictorial 824 is disposed to the right of the open pictorial which indicates that the conditions associated with the flow pictorial 824 should occur only after the step(s) associated with the open pictorial 820 have been completed. In order to provide further indications of the desired order to the operator, the number "3" is also disposed adjacent the word "FLOW."

In summary, the work area 688 of the donor/patient prep screen 812A not only conveys to the operator what type of steps must be performed for this aspect of the apheresis procedure and how to generally perform these steps, but also specifies the order in which these steps should be performed by two methods. Initially, the pictorial graphics 816, 820, and 824 are sequentially displayed in left-to-right fashion. Moreover, the three steps are also numerically identified next to their associated one-word textual description.

Figure 38:
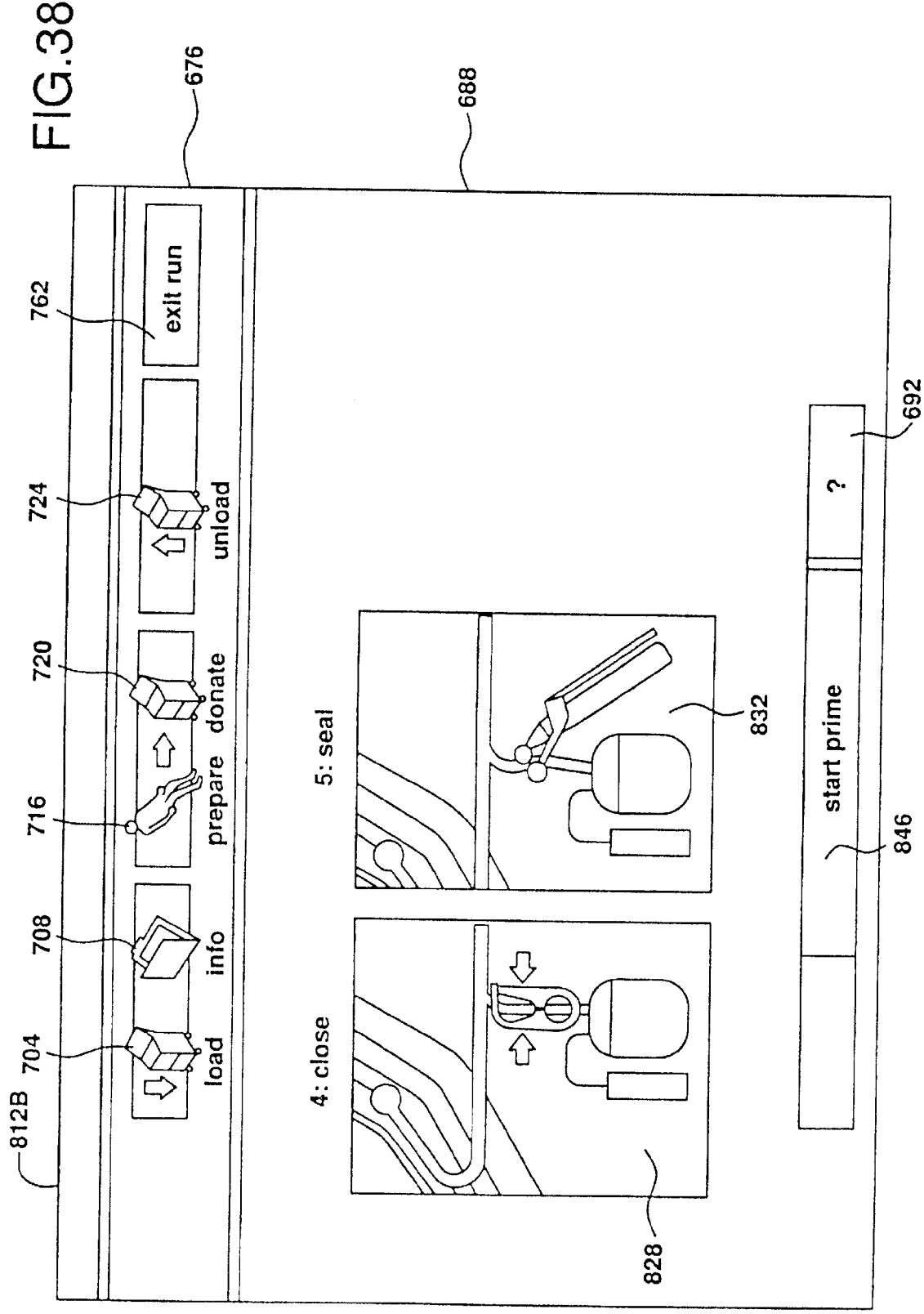
FIG. 38 is a second "donor/patient preps screen" for the computer graphics interface of the apheresis system of FIG. 1.

Once the operator completes all of the steps associated with the donor/patient prep screen 812A, the operator touches the continue button 752 which results in the display of a second donor/patient prep screen 812B as illustrated in FIG. 38. The donor/patient prep screen 812B includes a close pictorial 828 which pictorially conveys to the operator to terminate the flow of blood from the donor/patient 4 to the sample bag of the sample subassembly 46 by clamping the sample line and generally how this step may be affected by the operator. The word "CLOSE" is also positioned above the close pictorial 828 to provide a short textual instruction to the operator of the required action(s). The close pictorial 828 is disposed on the left side of the donor/patient prep screen 812B which indicates that this is the first step or substep associated with the donor/patient prep screen In order to provide an indication that this is in fact, however, the fourth step associated with the donor/patient preps, the number "4" is also disposed adjacent the word "CLOSE."

The donor/patient prep screen 812B also displays a seal pictorial 832 on the display 664. The seal flow pictorial 832 pictorially conveys to the operator that the sample line of the sample subassembly 46 should now be sealed off and generally how this step may be affected by the operator. The word "SEAL" is also positioned above the seal pictorial 832 to provide a short textual instruction to the operator of the required action(s). The seal pictorial 832 is disposed to the right of the close pictorial 828 which indicates that the step(s) associated with the seal pictorial 832 should be performed only after the step(s) associated with the close pictorial 828 have been completed. In order to provide further indications of the desired order to the operator, the number "5" is also disposed adjacent the word "SEAL" to indicate that this is actually the fifth step associated with the donor/patient preps.

In summary, the work area 688 of the donor/patient prep screen 812B not only conveys to the operator what type of steps must be performed for this aspect of the apheresis procedure and how to generally perform these steps, the work area 688 of the donor/patient prep screen 812B also specifies the order in which these steps should be performed by two methods. Initially, the pictorials 828, 832, and 836 are sequentially displayed in left-to-right fashion. Moreover, the four steps are also numerically identified next to their associated one-word textual description.

Figure 39:
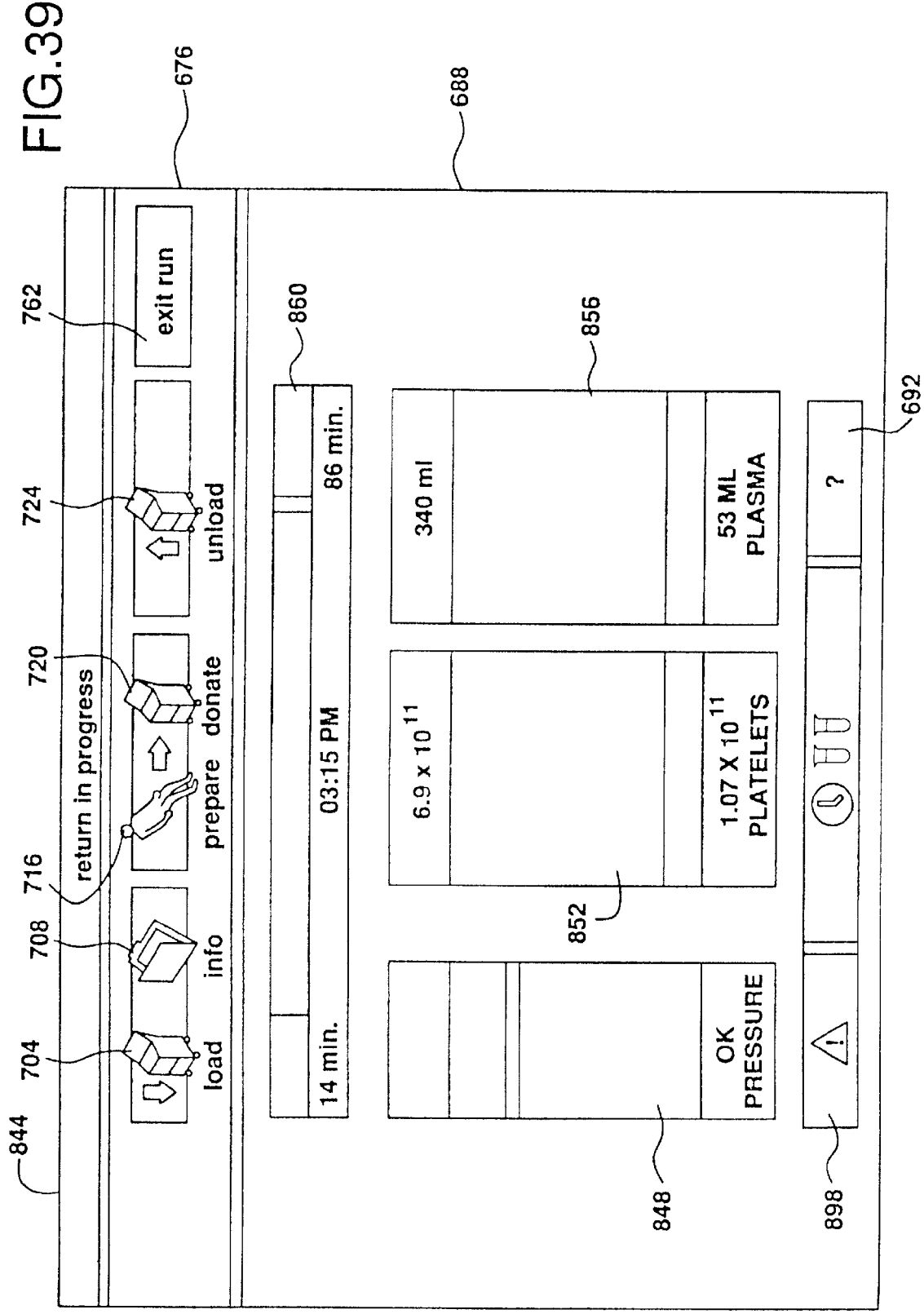
FIG. 39 is a "run screen" for the computer graphics interface of the apheresis system of FIG. 1.

Once the operator completes all of the donor/patient preps, the operator may touch the start prime button 846 on the donor/patient prep screen 812B which initiates the above-described blood prime of the extracorporeal tubing circuit 10 and blood processing vessel 352 and which results in the display of the run screen 844 illustrated in FIG. 39. The run screen 844 primarily displays information to the operator regarding the apheresis procedure. For instance, the run screen 844 includes a blood pressure display 848 (i.e., to convey to the operator the donor/patient's extracorporeal blood pressure), a platelet collect display 852 (i.e., to convey to the operator an estimate of the number of platelets which have been currently collected), a plasma collect display 856 (i.e., to convey to the operator the amount of plasma which has been currently collected), and a time display 860 (e.g., both the amount of time which has lapsed since the start of the collection procedure (the left bar graph and noted time), as well as the amount of time remaining in the collection procedure (the right bar graph and noted time). A control button (not shown) may be provided to toggle between the time remaining display and the start and stop time display.

The run screen 844 may also display, in the case of a single needle procedure (i.e., where only one needle is utilized to fluidly interconnect the donor/patient 4 with the blood component separation device 6), whether blood is being withdrawn from the donor/patient 4 (e.g., by displaying "draw in progress") or is being returned to the donor/patient 4 (e.g., by displaying "return in progress"). This information may be useful to the donor/patient 4 in that if the donor/patient 4 is attempting to maintain a certain blood pressure by squeezing an article to assist in removal of blood from the donor/patient 4, the donor/patient 4 will be provided with an indication to suspend these actions while blood is being returned to the donor/patient 4.

Figure 40:
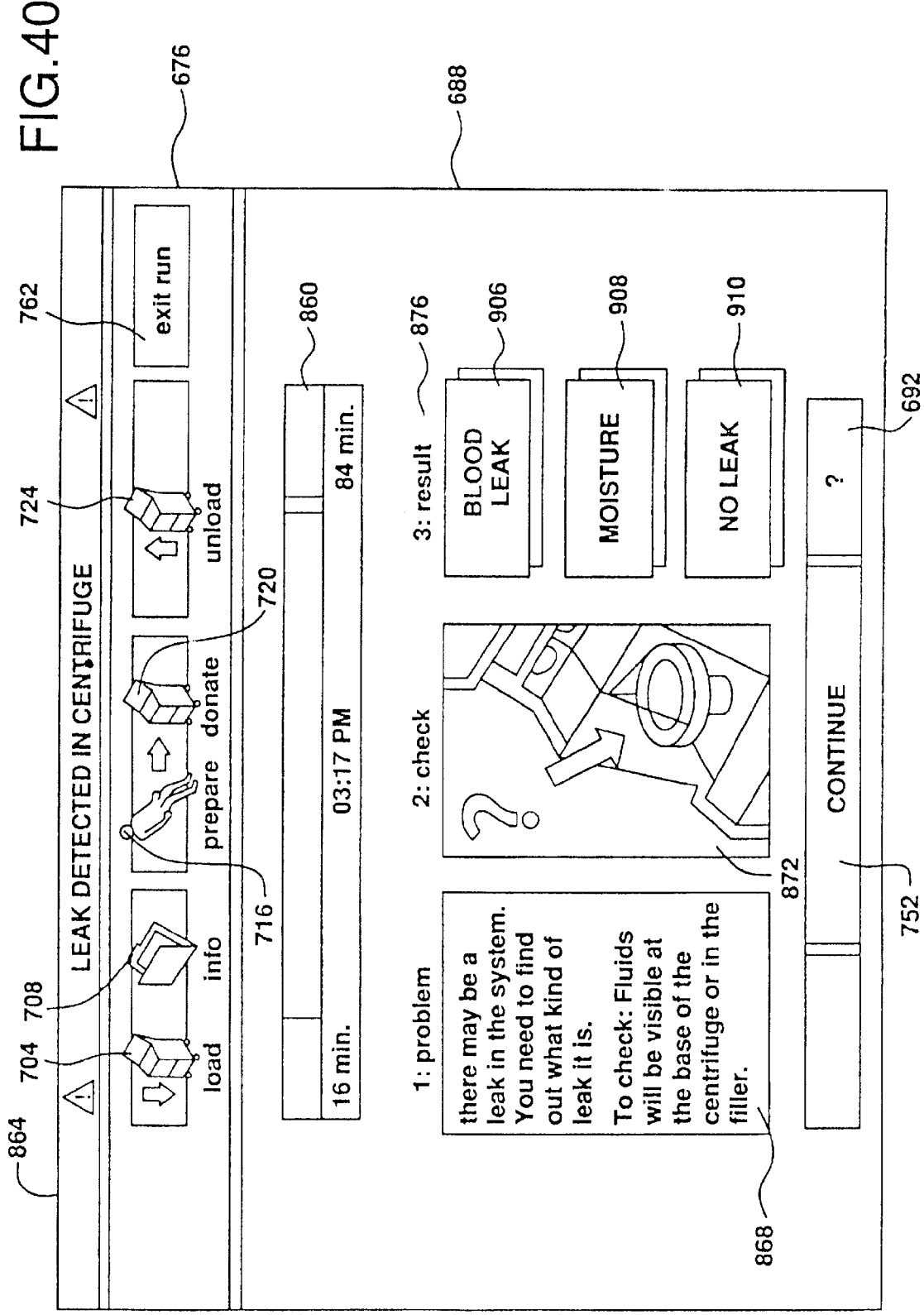
FIG. 40 is one embodiment of an "alarm screen" for the computer graphics interface of the apheresis system of FIG. 1.
Figure 41:
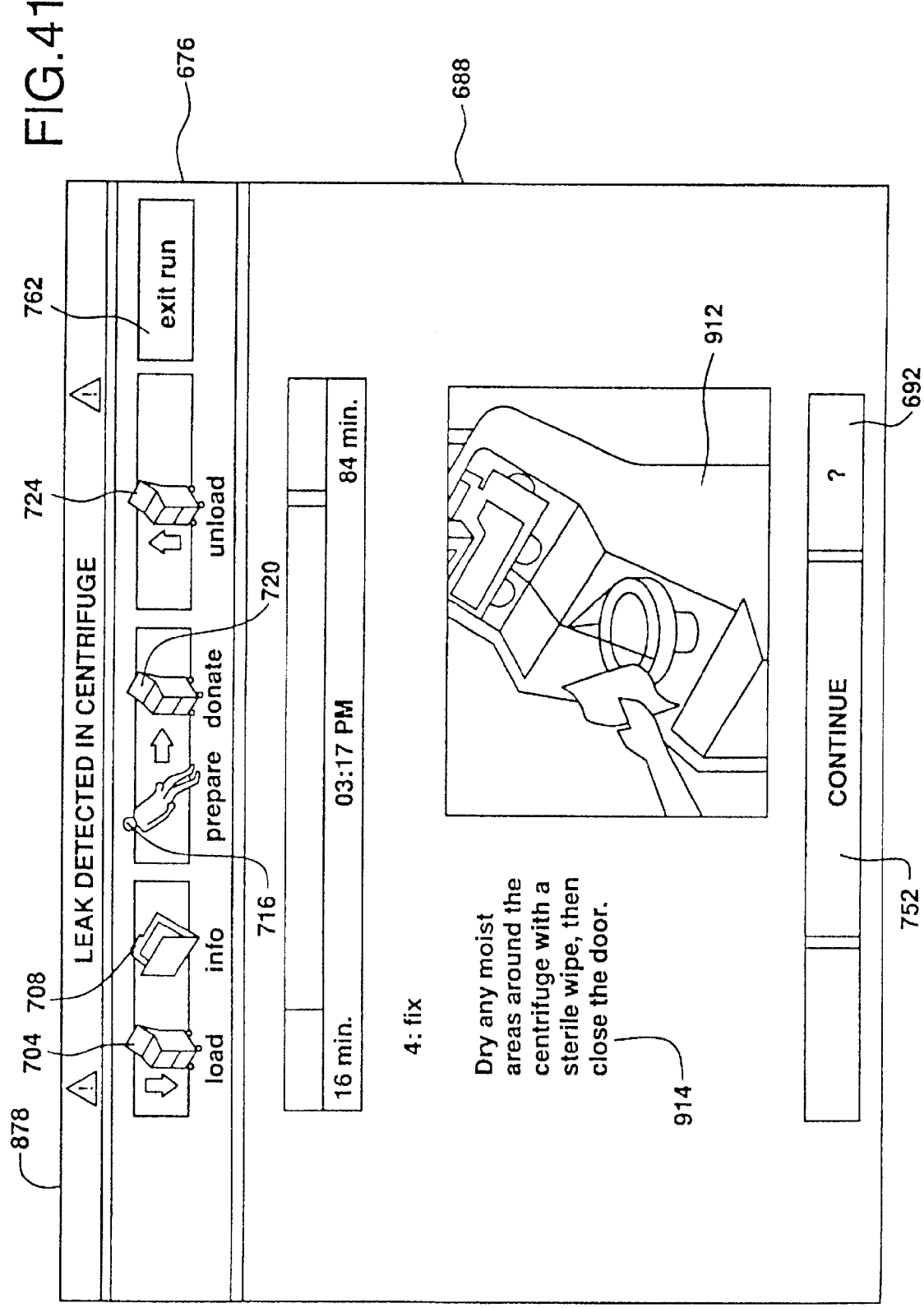
FIG. 41 is a "supplemental alarm screen" for the alarm screen of FIG. 40.

During the apheresis procedure, certain conditions may be detected by the apheresis system 2 which would benefit from an investigation by the operator. If one of these types of conditions is detected, an appropriate alarm screen is displayed to the operator. One embodiment of an alarm screen 864 is illustrated in FIG. 40. Initially, the alarm screen 864 textually conveys a potential problem with the system 2 via a problem graphic 868. The text may be useful in ensuring that the operator understands the problem. The alarm screen 864 also includes an action pictorial 872 which graphically conveys to the operator the action which should be taken in relation to the problem. These are actions which may be difficult or impossible for the system 2 to take itself. Finally, the alarm screen includes an inspection results array 876 which allows the operator to indicate the results of the inspection. In the illustrated embodiment, the array 876 includes a blood leak button 906, a moisture button 908, and a no leak button 910.

Depending upon the selection made by the operator on the inspection results array additional questions may be posed to the operator in further screens which require further investigation and/or which specify the desired remedial action. For instance, the supplemental alarm screen 878 of FIG. 41 may be generated by the operator touching the moisture button 908 on the alarm screen 864. The supplemental alarm screen 878 includes a remedial action pictorial 912 and remedial action text 914 to convey to the operator how to correct the identified problem.

The computer interface 660 may also allow the operator to initiate some type of corrective action based upon observations made by and/or conveyed to the operator. For instance, various screens of the interface 660 may include a trouble shooting button 898 which will generate one or more trouble shooting screens. These trouble shooting screens may include menus or the like to allow the operator to indicate what type of potential problem exists.

Figure 42:
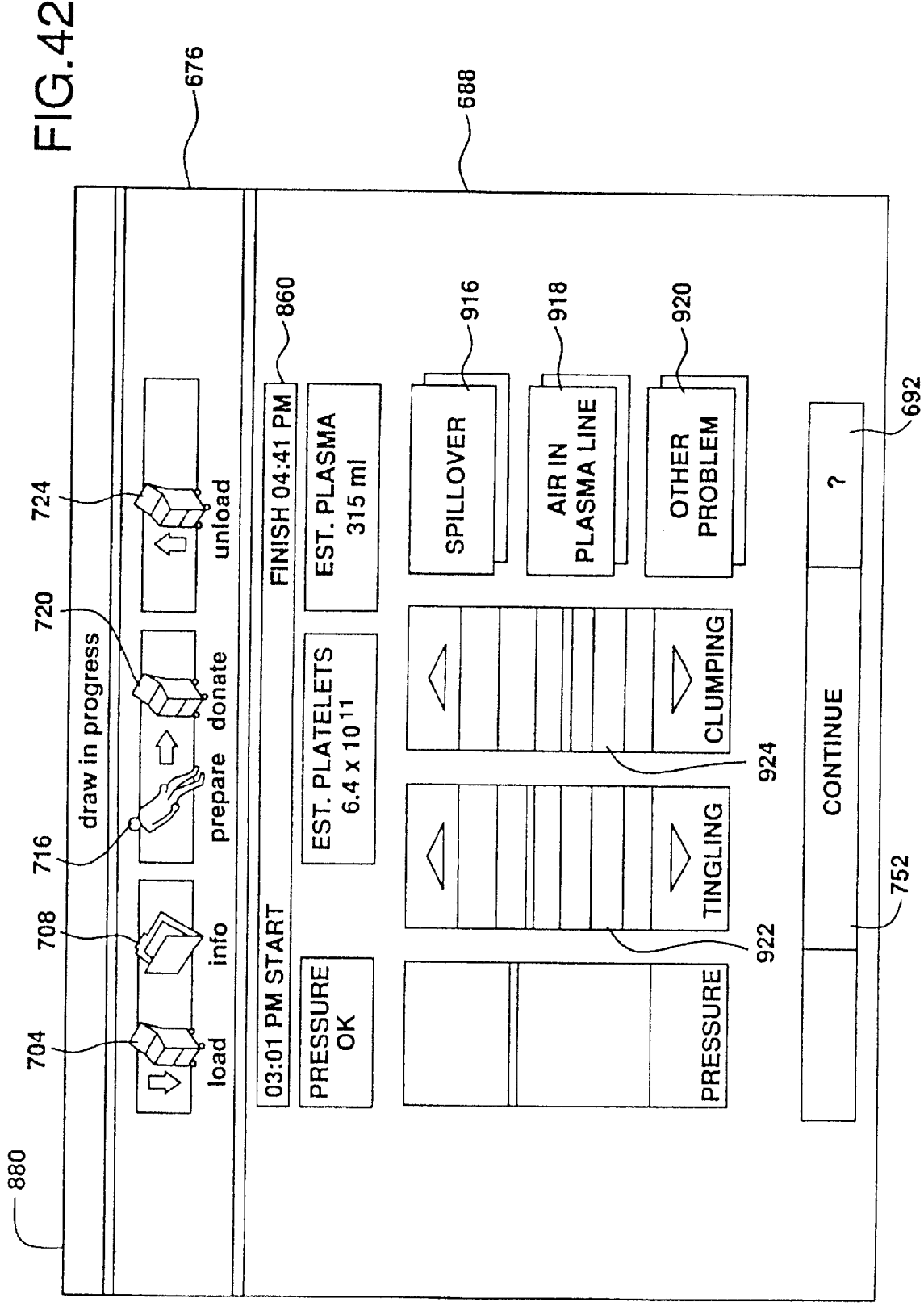
FIG. 42 is one embodiment of a "trouble shooting screen" for the computer graphics interface of the apheresis system of FIG. 1.

One embodiment of a trouble shooting screen 880 is presented in FIG. 42. The trouble shooting screen 880 includes a donor/patient tingling button 922. This button 922 would be utilized by the operator to attempt to remedy the effects of AC on the donor/patient 4 in response to the donor/patient indicating a "tingling sensation" or, alternatively "AC reaction." When the operator hits the "down arrow" of the donor/patient tingling button 922, the system 2 attempts to correct the condition in a predetermined manner (i.e., a predetermined protocol is employed preferably this protocol does not require operator actions or decisions). Once the tingling sensation no longer exists, the operator may use the "up arrow" button to return the bar on the donor/patient tingling button 922 to its original position.

The trouble shooting screen 880 also includes a clumping button 924. This button 924 would be utilized by the operator if any undesired clumping of the collected product (e.g., platelets) was observed. When the operator hits the "down arrow" of the clumping button 924, the system 2 attempts to correct the condition in a predetermined manner (i.e., a predetermined protocol is employed and preferably this protocol does not require operator actions or decisions). Once the clumping is no longer observed by the operator, the operator may use the "up arrow" button to return the bar on the clumping button 924 to its original position.

The trouble shooting screen 880 may also include a spillover button 916 and an "air in plasma line" button 918. The spillover button 916 would be engaged by the operator if red blood cells were observed in the platelet outlet tubing 66, in the platelet collect bag 84, and/or flowing beyond the RBC dam 232. Activation of the spillover button 916 via the touch screen capabilities would result in the system 2 using a predetermined and preferably automatic protocol is performed by the system 2 to correct this condition. Similarly, if the operator observes air in the plasma line 918 and engages the button 918, the system 2 again will preferably automatically employ a predetermined protocol to correct this condition.

The "other problem button" 920 may be utilized to generate further trouble shooting screens to list further problems which may occur in the apheresis procedure. Again, preferably upon the operator touching the associated button indicative of a particular problem, a predetermined protocol will be preferably automatically employed to attempt to correct the same.

Figure 44:
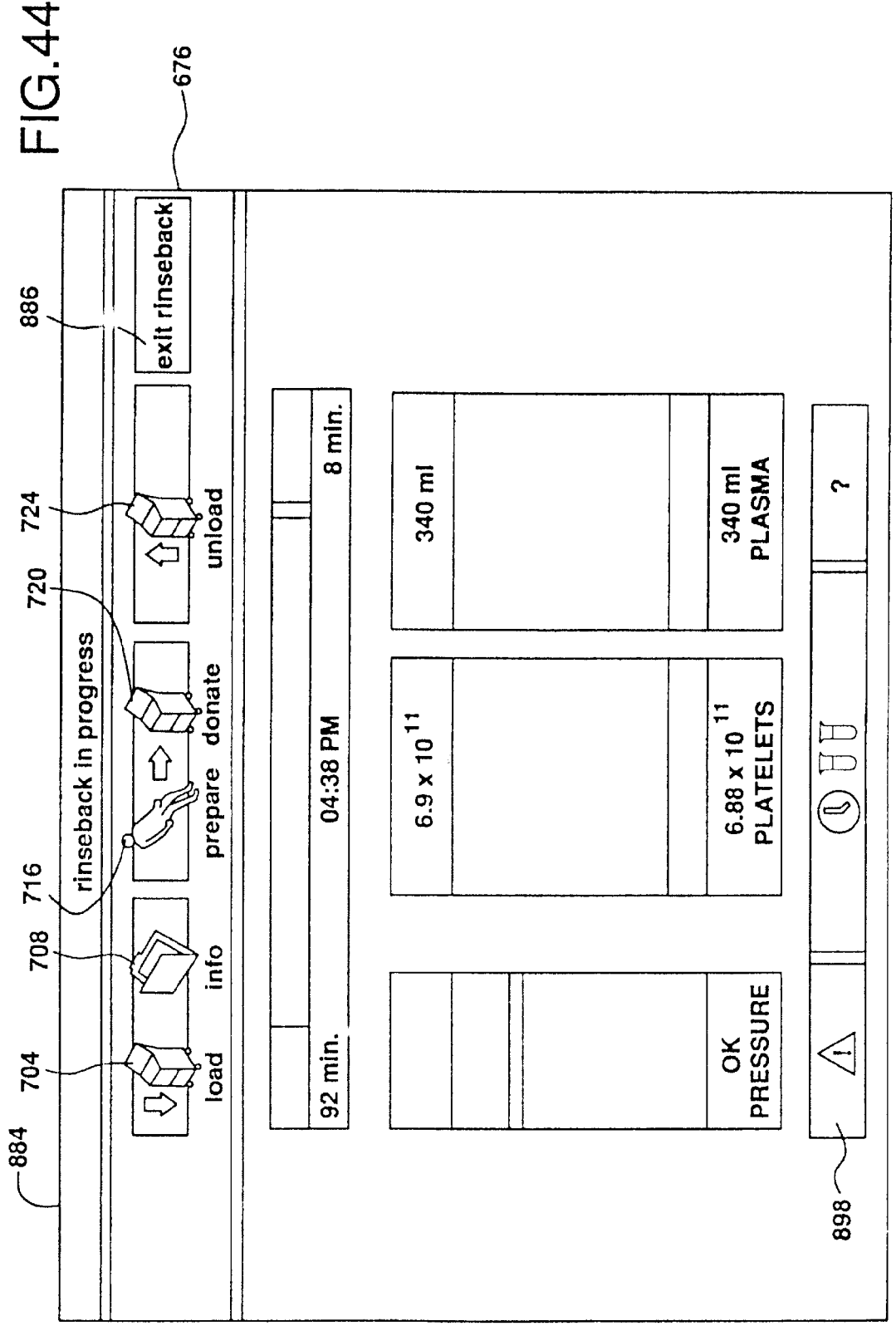
FIG. 44 is a "rinseback screen" for the computer graphics interface of the apheresis system of FIG. 1.

Upon completion of the collection portion of the apheresis procedure, the rinseback screen 884 is produced on the display 664 which indicates that the rinseback procedure will now be performed and which is illustrated in FIG. 44. Once the rinseback is completed, the color/shade of the donate icon 720 changes from the second color to the third color/shade to indicate that all steps associated with this aspect of the apheresis procedure have been completed. Moreover, the color/shade of the unload icon 724 will also change from the first color/shade to the second color/shade to indicate to the operator that the step(s) associated therewith may now be performed.

Figure 43:
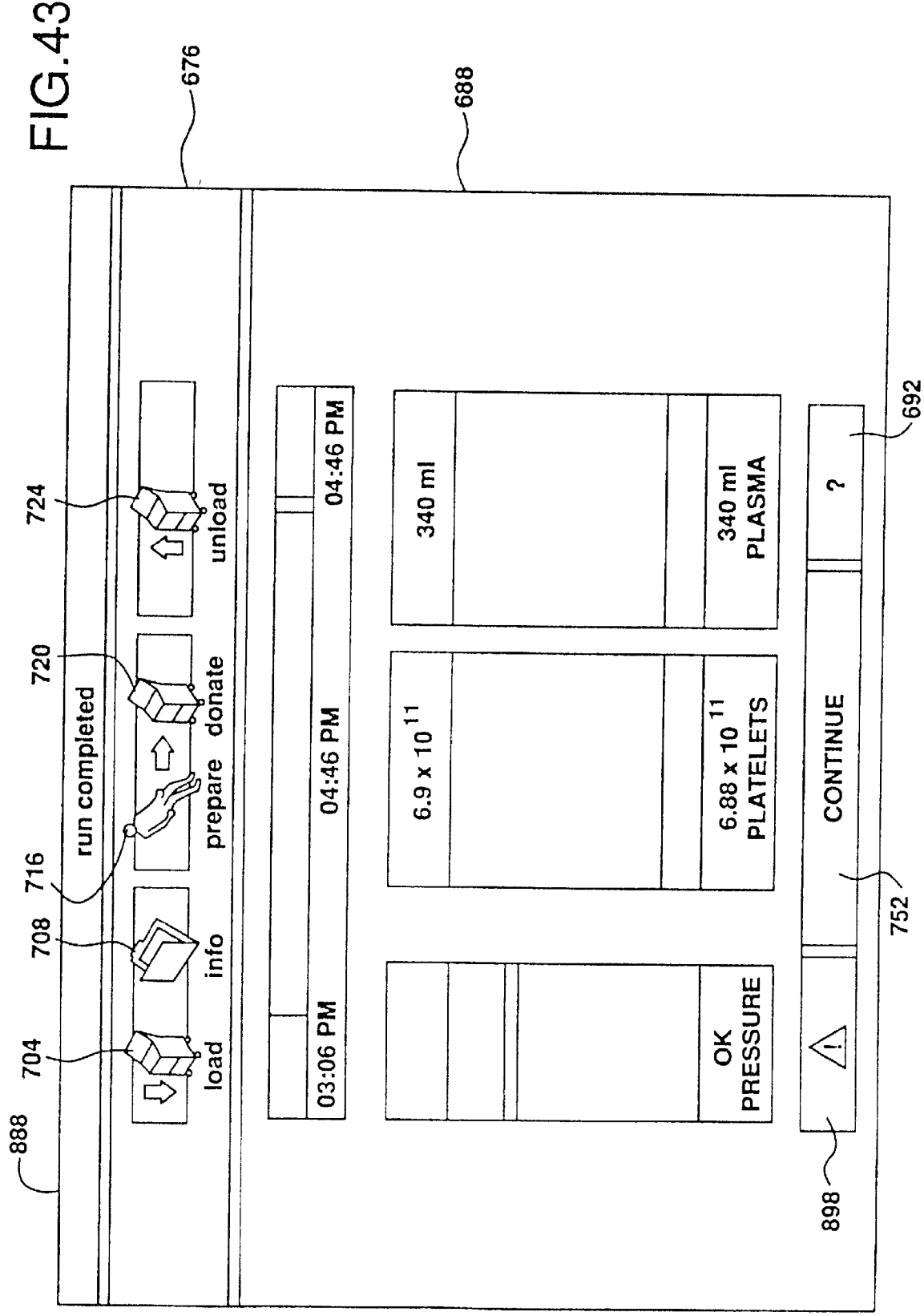
FIG. 43 is a "final run data display screen" for the computer graphics interface of the apheresis system of FIG. 1.

Upon completion of the rinseback, a run finish screen may be produced on the display 664 to provide the final collection data as illustrated in FIG. 43 (e.g., the associated yields of platelets and plasma collected during the procedure) as well as the fact that the procedure is over (e.g., by displaying "run completed"). The operator may then touch the continue button 752.

Figure 45:
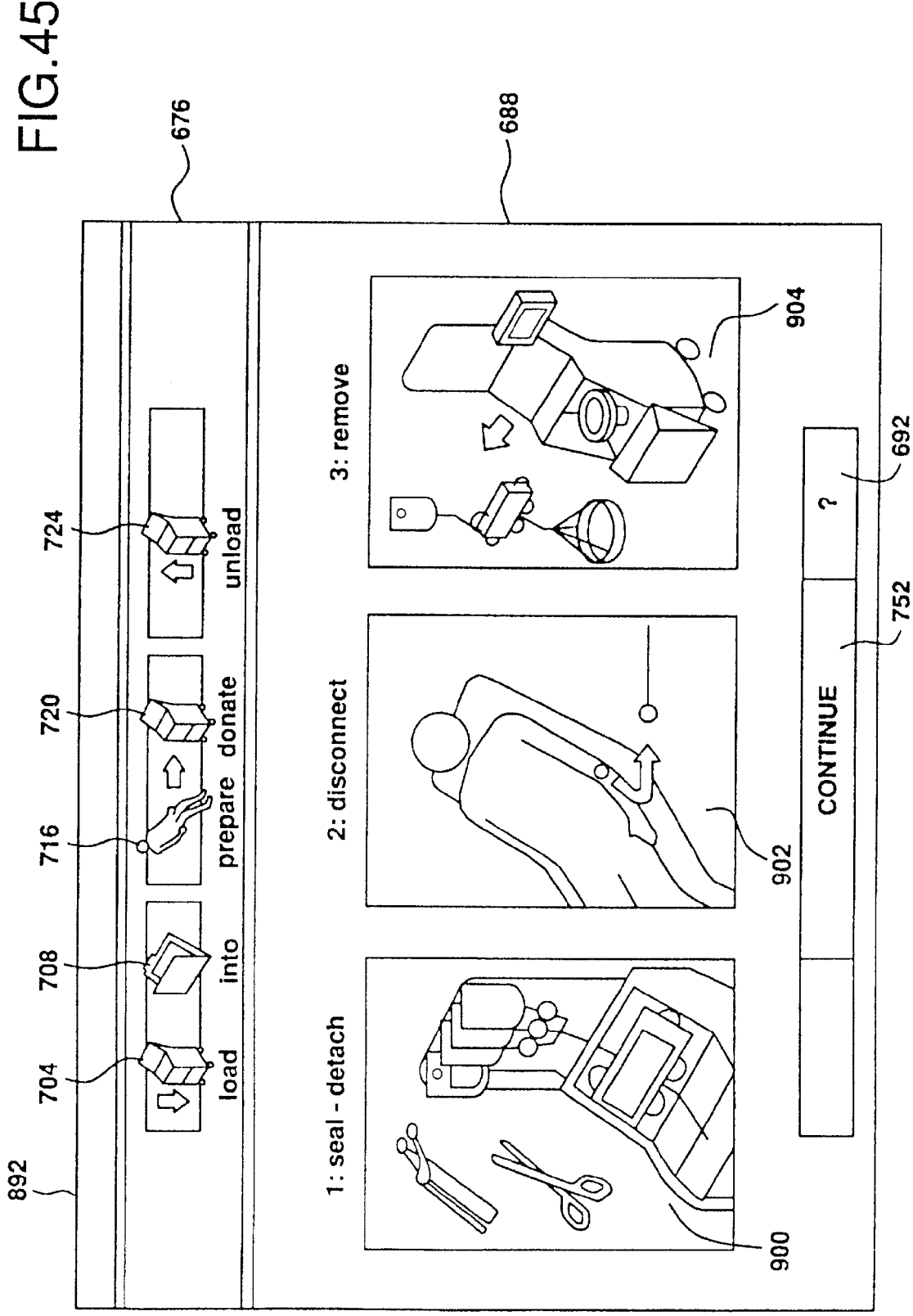
FIG. 45 is an "unload screen" for the computer graphics interface of the apheresis system of FIG. 1.

Once the rinseback procedure is completed, an unload screen 892 will be presented on the display 664 and is illustrated in FIG. 45. The unload screen 892 may sequentially display a number of pictorials to the operator to convey the steps which should be completed to terminate the procedure. For instance, a seal/detach pictorial 900 may be initially displayed on the unload screen 892 to pictorially convey to the operator that the tubes leading to the platelet, plasma and/or RBC collect bag(s) 84, 94 and 954 should each be sealed such that the platelet, plasma and/or RBC collect bag(s) 84, 94 and 954 respectively, may be removed. Once the operator touches the continue button 752, a disconnect pictorial 902 may be presented on the unload screen 892 to pictorially convey to the operator that the access needle 32 should be removed from the donor/patient 4. Once the operator touches the continue button 752, a remove pictorial 904 is presented on the unload screen 892 to pictorially convey to the operator that the disposable set 8 should be removed from the blood component separation device 6 and disposed of properly.

The computer interface 660 provides a number of advantages. For instance, the computer interface 660 utilizes a three-way color/shade differentiation to conveniently convey the status of the apheresis procedure to the operator. An icon is presented in one color/shade if the step(s) associated with the icon are not yet ready to be performed, while the icon is presented in another color/shade if the step(s) associated with the icon are ready to be performed or are being performed, while the icon is presented in yet another color/shade if the step(s) associated with the icon have been completed. Moreover, the computer interface 660 provides pictorials to the operator of at least certain of the steps of the apheresis procedure. Furthermore, the desired/required ordering of at least the fundamental steps of the apheresis procedure is conveyed to the operator. Finally, the interface 660 allows for correction of certain conditions, which after appropriate operator input, are remedied by the system 2 in accordance with a predetermined protocol.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method for extracorporeal collection of blood components from a donor/patient comprising:
    removing blood from a donor/patient through a single needle;
    flowing said blood into a dual stage blood processing vessel;
    separating plasma from said blood within said blood processing vessel;
    collecting at least a portion of said plasma in a plasma collection reservoir separate from said blood processing vessel;
    separating red blood cells from said blood within said dual stage blood processing vessel;
    collecting at least a portion of Mid separated red blood cells in a red blood cell collection reservoir separate from said blood processing vessel, wherein said plasma separation and collection steps are completed at least partially contemporaneously with said red blood cell separation and collection steps;
    returning uncollected blood components of said blood to said donor/patient through said single needle; and
    replacing fluid volume in said donor/patient by flowing a replacement fluid to said donor/patient through said single needle.

2. A method as recited in claim 1, whereby the red blood cell collecting step provides for obtaining a double volume of collected red blood cells.

3. A method as recited in claim 2 in which said double volume of collected red blood cells totals substantially about 400 milliliters contained in two substantially separate reservoirs.

4. A method as recited in claim 1, wherein said plasma collection step is completed at least partially separately from said red blood cell collection step.

5. A method as recited in claim 1, wherein prior to said red blood cell collection step, and separate from said plasma collection step, said method further comprises a red blood cell collection set-up phase including:
    establishing a hematocrit of at least about 80 within said separated red blood cells within said blood processing vessel and an AC ratio within said blood at about 8.

6. A method as recited in claim 5, further comprising maintaining said hematocrit and AC ratio during said red blood cell separation and collection steps.

7. A method as recited in claim 1 in which said step of delivering a replacement fluid includes flowing replacement fluid at a rate equal to the total flow rate of collected blood components multiplied by the desired fluid balance percentage resulting within the donor/patient.

8. A method as recited in claim 7 in which said step of delivering a replacement fluid includes pumping replacement fluid at a rate equal to the total flow rate of collected fluids minus the inlet flow rate of anticoagulant multiplied by the desired fluid balance percentage resulting within the donor/patient.

9. A method as recited in claim 7 in which a replacement fluid is pumped from a source first to an intermediate reservoir prior to ultimate delivery to the donor/patient.

10. A method as recited in claim 7 in which a replacement fluid is delivered to the donor/patient in a bolus.

11. A method as recited in claim 7 in which a replacement fluid is delivered to the donor/patient in a substantially continuous fashion.

12. A method as recited in claim 1 further comprising:
    retaining the separated red blood cells in a first stage of the processing vessel;
    establishing a pre-determined packing factor for the separated red blood cells within said blood processing vessel;
    and flowing the red blood cells to red blood cell outlet.

13. A method as recited in claim 12 in which said collecting step further includes a step for collecting at least a portion of the separated plasma in a plasma collection reservoir separate from said blood processing vessel to establish collected plasma; and wherein said plasma collection step is performed at least partially contemporaneously with said red blood cell collection step.

14. A method as recited in claim 13, wherein said plasma collection step is performed prior to said red blood cell collection step.

15. A method as recited in claim 13, wherein said plasma collection step is performed at least partially alter said red blood cell collection step.

16. A method as recited in claim 13, wherein said red blood cell collection step is performed at least partially after said plasma collection step.

17. A method as recited in claim 11 further comprising
    establishing a packing factor of at least about 13 for the separated red blood cells within said blood processing vessel.

18. A method as recited in claim 17 wherein said packing factor is between 11 and 21.

19. A method as recited in claim 18 wherein said packing factor is at least about 13.

20. A method as recited in claim 19 in which the packing factor is about 16.

21. A method as recited in claim 17 which further includes establishing an AC ratio in tho blood processing vessel of between about 6 and about 16.

22. A method as recited in claim 17 in which the packing factor is about 16 during the contemporaneous collection of separated plasma and separated red blood cell and the packing factor is then reduced to about 13 during the at least partial step of collecting separated red blood cells after the performance of the collection of separated plasma.

23. A method as recited in claim 1, further comprising a set up step prior to said collecting steps; said set up step comprising:
    flowing the separated blood components Out of said blood processing vessel, wherein substantially all of said separated blood components flowing out of the blood processing vessel are accumulated for re-infusion to a donor/patient during the set-up step.

24. A method as recited in claim 23, wherein said blood is flowed into said blood processing vessel at an inlet flow rate, and said set-up step comprises:
    reducing said inlet flow rate.

25. A method as recited in claim 23, wherein said blood processing vessel is rotated at an rpm rate, and wherein said set-up step comprises:
    increasing said rpm rate.

26. A method as recited in claim 1, wherein said processing vessel includes a first stage and a second stage, the second stage being separated from said first stage by a dam, a blood inlet for communicating blood into the first stage, a plasma outlet disposed in the second stage and a red blood cell outlet disposed in the first stage; and wherein during said plasma collection step, said method further comprises:

separating plasma from said blood within said centrifugal dual stage blood processing vessel to establish separated plasma, whereby a portion of the separated plasma flows over the dam in the processing vessel to the plasma outlet in the second stage of the processing vessel;

separating red blood cells from said blood within said centrifugal dual stage blood processing vessel to establish separated red blood cells whereby the separated red blood cells remain in the first stage of the processing vessel and flow to the red blood cell outlet; and recirculating a portion of the uncollected separated blood components into said blood processing vessel.

27. A device for extracorporeal separation and collection of blood components front a donor/patient, comprising:

a centrifugal blood processing channel into which blood from a donor/patient is adapted to be flowed, and in which said blood is separated into at least separated plasma and separated red blood cells; said centrifugal dual stage blood processing channel including a first stage and a second stage, the second stare being separated from said first stage by a dam, a blood inlet for communicating blood into the first stage, a plasma outlet disposed in the second stage and a red blood cell outlet disposed in the first stage; said centrifugal blood processing channel being adapted to be used with:

a removable plasma collection reservoir operably connected to said centrifugal blood processing channel, whereby into which at least a portion of said separated plasma is collected;

a removable red blood cell collection reservoir operably connected to said blood processing channel whereby a portion of said separated red blood cells are collected in said red blood cell collection reservoir, and a replacement fluid assembly which is operably connectable to the donor/patient; wherein said replacement fluid assembly is adapted to deliver replacement fluid to the donor/patient.

28. A disposable blood tubing set adapted to be used with a device for extracorporeal separation and collection of blood components from a donor/patient, said disposable blood tubing set comprising:

a disposable centrifugal dual stage blood processing vessel into which blood from a donor/patient is adapted to be flowed, and in which said blood is separated into at least separated plasma and separated red blood cells; said centrifugal dual stage blood processing vessel including a firs: stage and a second stage, the second stage being separated from said first stage by a dam, a blood inlet for communicating blood into the first stage, a plasma outlet disposed in the second stage and a red blood cell outlet disposed in the first stage;

a plasma collection reservoir operably connected to said centrifugal blood processing vessel, whereby into which said plasma collection reservoir at least a portion of said separated plasma is collected;

a red blood cell collection reservoir operably connected to said blood processing vessel whereby a portion of said separated red blood cells are collected in said red blood cell collection reservoir; and a disposable fluid flow cassette assembly operably interconnected to said centrifugal blood processing vessel, said cassette assembly having an intermediate reservoir disposed therein, said intermediate reservoir being adapted to receive separated uncollected blood components from said centrifugal blood processing vessel; and a replacement fluid assembly which is operably connected to said fluid flow cassette and said intermediate reservoir; wherein said replacement fluid assembly is adapted to deliver replacement fluid to said intermediate reservoir for subsequent infusion of the replacement fluid into a donor/patient.

* * * * *